(12) United States Patent
Hayashi et al.

(10) Patent No.: US 9,905,775 B2
(45) Date of Patent: Feb. 27, 2018

(54) ORGANIC ELECTROLUMINESCENT DEVICE

(71) Applicants: HODOGAYA CHEMICAL CO., LTD., Tokyo (JP); SFC CO., LTD, Chungcheongbuk-do (KR)

(72) Inventors: Shuichi Hayashi, Tokyo (JP); Naoaki Kabasawa, Tokyo (JP); Shunji Mochiduki, Tokyo (JP); Se-Jin Lee, Chungcheongbuk-do (KR); Oun-gyu Lee, Chungcheongbuk-do (KR); Bong-Ki Shin, Chungcheongbuk-do (KR)

(73) Assignees: HODOGAYA CHEMICAL CO., LTD., Tokyo (JP); SFC CO., LTD, Chungcheongbuk-Do (KR)

( * ) Notice: Subject to any disclaimer, the term of this patent is extended or adjusted under 35 U.S.C. 154(b) by 0 days.

(21) Appl. No.: 15/541,429

(22) PCT Filed: Jan. 5, 2016

(86) PCT No.: PCT/JP2016/050064
§ 371 (c)(1),
(2) Date: Jul. 3, 2017

(87) PCT Pub. No.: WO2016/111270
PCT Pub. Date: Jul. 14, 2016

(65) Prior Publication Data
US 2017/0358753 A1 Dec. 14, 2017

(30) Foreign Application Priority Data
Jan. 7, 2015 (JP) .................................. 2015-001298

(51) Int. Cl.
*H01L 35/24* (2006.01)
*H01L 51/00* (2006.01)
(Continued)

(52) U.S. Cl.
CPC ........ *H01L 51/0059* (2013.01); *C07C 211/54* (2013.01); *C07D 403/04* (2013.01);
(Continued)

(58) Field of Classification Search
CPC ..... H01L 51/0059; C23C 14/14; C23C 14/34; C07C 211/54; C07D 403/04
(Continued)

(56) References Cited

U.S. PATENT DOCUMENTS 5,639,914 A 6/1997 Tomiyama et al.
5,707,747 A 1/1998 Tomiyama et al.
(Continued)

FOREIGN PATENT DOCUMENTS

JP 7-126615 5/1995
JP 8-48656 2/1996
(Continued)

OTHER PUBLICATIONS

International Search Report issued in WIPO Patent Application No. PCT/JP2016/050064, dated Mar. 29, 2016.

*Primary Examiner* — David S Blum
(74) *Attorney, Agent, or Firm* — Greenblum & Bernstein, P.L.C.

(57) ABSTRACT

The present invention provides an organic electroluminescent device having at least an anode, a hole transport layer, a luminous layer, an electron transport layer, and a cathode in this order, wherein the hole transport layer contains an arylamine compound having a specific structure, and the luminous layer contains an indenoindole derivative or a carbazole derivative having a specific structure. The organic EL device of the present invention is an organic EL device improved in luminous efficiency, driving voltage and durability.

9 Claims, 64 Drawing Sheets

9  CATHODE
8  ELECTRON INJECTION LAYER
7  ELECTRON TRANSPORT LAYER
6  LUMINOUS LAYER
5  HOLE TRANSPORT LAYER
5a FIRST HOLE TRANSPORT LAYER
5b SECOND HOLE TRANSPORT LAYER
3  HOLE INJECTION LAYER
2  TRANSPARENT ANODE
1  GLASS SUBSTRATE

(51) Int. Cl.

| | |
|---|---|
| *C07C 211/54* | (2006.01) |
| *C07D 495/04* | (2006.01) |
| *C07D 403/04* | (2006.01) |
| *C07D 491/048* | (2006.01) |
| *C07D 495/14* | (2006.01) |
| *C09K 11/06* | (2006.01) |
| *H01L 51/52* | (2006.01) |
| *H01L 51/50* | (2006.01) |

(52) U.S. Cl.
CPC ....... *C07D 491/048* (2013.01); *C07D 495/04* (2013.01); *C07D 495/14* (2013.01); *C09K 11/06* (2013.01); *H01L 51/006* (2013.01); *H01L 51/0067* (2013.01); *H01L 51/0072* (2013.01); *H01L 51/0085* (2013.01); *C09K 2211/1029* (2013.01); *C09K 2211/185* (2013.01); *H01L 51/5016* (2013.01); *H01L 51/5064* (2013.01); *H01L 51/5072* (2013.01); *H01L 51/5206* (2013.01); *H01L 51/5221* (2013.01)

(58) Field of Classification Search
USPC .......................................................... 257/40
See application file for complete search history.

(56) References Cited

U.S. PATENT DOCUMENTS

| | | | |
|---|---|---|---|
| 5,792,557 A | 8/1998 | Nakaya et al. | |
| 7,357,992 B2 | 4/2008 | Kato et al. | |
| 7,402,701 B2 | 7/2008 | Kato et al. | |
| 7,759,030 B2 | 7/2010 | Abe et al. | |
| 7,799,492 B2 | 9/2010 | Abe et al. | |
| 8,021,764 B2 | 9/2011 | Hwang et al. | |
| 8,021,765 B2 | 9/2011 | Hwang et al. | |
| 8,188,315 B2 | 5/2012 | Hwang et al. | |
| 8,394,510 B2 | 3/2013 | Mizuki et al. | |
| 8,895,159 B2 | 11/2014 | Mizuki et al. | |
| 8,974,922 B2 | 3/2015 | Hwang et al. | |
| 9,478,754 B2 | 10/2016 | Hwang et al. | |
| 2012/0203010 A1 | 8/2012 | Matsumoto et al. | |
| 2014/0217393 A1 | 8/2014 | Kato et al. | |
| 2015/0380657 A1 | 12/2015 | Yokoyama et al. | |
| 2017/0005273 A1 | 1/2017 | Hwang et al. | |
| 2017/0256716 A1* | 9/2017 | Wang | H01L 51/0035 |

FOREIGN PATENT DOCUMENTS

| | | |
|---|---|---|
| JP | 3194657 | 6/2001 |
| JP | 2005-108804 | 4/2005 |
| JP | 2006-151979 | 6/2006 |
| JP | 2006-219393 | 8/2006 |
| JP | 2008-16827 | 1/2008 |
| JP | 2010-40829 | 2/2010 |
| JP | 4943840 | 3/2012 |
| JP | 2014-513064 | 5/2014 |
| KR | 10-2013-0060157 | 6/2013 |
| WO | 2008/062636 | 5/2008 |
| WO | 2011/049123 | 4/2011 |
| WO | 2012/121561 | 9/2012 |
| WO | 2013/035329 | 3/2013 |
| WO | 2014/058183 | 4/2014 |
| WO | 2014/129201 | 8/2014 |
| WO | 2016/017594 | 2/2016 |

\* cited by examiner

9   CATHODE
8   ELECTRON INJECTION LAYER
7   ELECTRON TRANSPORT LAYER
6   LUMINOUS LAYER
5   HOLE TRANSPORT LAYER
5a  FIRST HOLE TRANSPORT LAYER
5b  SECOND HOLE TRANSPORT LAYER
3   HOLE INJECTION LAYER
2   TRANSPARENT ANODE
1   GLASS SUBSTRATE (1-1)

(1-2)

(1-3)

(1-4)

(1-5)

(1-6)

(1-7)

(1-8)

(1-9)

(1-10)

(1-11)

(1-12)

(1-13)

(1-14)

(1-15)

(1-16)

(1-17)

(1-18)

(1-19)

(1-20)

(1-21)

(1-22)

(1-23)

(1-24)

(1-25)

(1-26)

(1-27)

(1-40)

(1-41)

(1-42)

(1-43)

(1-44)

(1-45)

(1-46)

(1-47)

(1-48)

(1-49)

(1-50)

(1-51)

(1-52)

(1-53)

(1-54)

(1-55)

(1-56)

(1-57)

(1-58)

(1-59)

(1-60)

(1-61)

(1-62)

(1-63)

(1-64)

(1-65)

(1-66)

(1-67)

(1-68)

(1-69)

(1-70)

(1-77)

(1-78)

(1-79)

(1-80)

(1-81)

(1-82)

(1-83)

(1-84)

(1-85)

(1-86)

(1-87)

(1-88)

(1-89)

(1-90)

(1-91)

(1-92)

(1-93)

(2-1)

(2-2)

(2-3)

(2-4)

(2-5)

(2-11)

(2-12)

(2-13)

(2-14)

(2-15)

(3-7)

(3-8)

(3-9)

(3-10)

(3-11)

(3-12)

(3-13)

(3-14)

(3-15)

(3-16)

(3-17)

(3-18)

(3-19)

(3-20)

(3-21)

(3-22)

(3-23)

(4-1)
(4-2)
(4-3)
(4-4)
(4-5)
(4-6)

(4-7)

(4-8)

(4-9)

(4-10)

(4-11)

(4-12)

(4-13)

(4-14)

(4-15)

(4-16)

(4-17)

(4-18)

(4-19)

(4-20)

(4-21)

(4-22)

(4-23)

(4-24)

(4-25)

(4-26)

(4-27)

(4-28)

(4-29)

(4-30)

(4-31)

(4-32)

(4-33)

(4-34)

(4-35)

(4-36)

(4-37)

(4-38)

(4-39)

(4-40)

(4-41)

(4-42)

(4-43)

(4-44)

(4-45)

(4-46)

(4-47)

(4-48)

(4-49)

(4-50)

(4-51)

(4-57)

(4-58)

(4-59)

(4-60)

(4-61)

(4-62)

(4-63)

(4-64)

(4-65)

(4-66)

(4-77)

(4-78)

(4-79)

(4-80)

(4-81)

(4-82)

(4-83)

(4-84)

(4-85)

(4-86)

(4-87)

(4-88)

(4-89)

(4-90)

(4-91)

(4-92)

(4-93)

(4-94)

(4-95)

(4-96)

(4-97)

(4-98)

(4-99)

(4-100)

(4-101)

(4-102)

(4-103)

(4-104)

(4-105)

(4-106)

(4-107)

(4-108)

(4-109)

(4-110)

(4-111)

(4-112)

(4-113)

(4-114)

(4-115)

(4-116)

(4-117)

(4-118)

(4-119)

(4-120)

(4-121)

(4-122)

(4-123)

(4-124)

(4-125)

(4-126)

(6-1)

(6-2)

(6-3)

(6-4)

(6-5)

(6-6)

(6-7)

(6-8)

(6-9)

(6-10)

(6-11)

(6-12)

(6-13)

(6-14)

(6-15)

(6-16)

(6-17)

(6-18)

(6-19)

(6-20)

(6-21)

(6-22)

(6-23)

(6'-1)

(6'-2)

(7-1)

(7-2)

(7-3)

(7-4)

(7-5)

(7-6)

(7-7)

(7-8)

(7-9)

(7-10)

(7-11)

(7-12)

(7-13)

(7-14)

(7-15)

(7-16)

(7-17)

ORGANIC ELECTROLUMINESCENT DEVICE

TECHNICAL FIELD

This invention relates to an organic electroluminescent device and, in detail, relates to an organic electroluminescent device (will hereinafter be referred to simply as an organic EL device) using a specific arylamine compound and a heterocyclic compound having a specific condensed ring structure (and a specific pyrimidine derivative).

BACKGROUND ART

Since an organic EL device is a self light-emitting device, it is brighter, better in visibility, and capable of clearer display, than a liquid crystal device. Hence, energetic researches have been conducted on organic EL devices.

In 1987, C. W. Tang et al. of Eastman Kodak Company developed a laminated structure device sharing various roles among different materials, thereby imparting practical applicability to organic EL devices using organic materials. Such an organic EL device is formed by laminating a layer of a fluorescent body capable of transporting electrons, and a layer of an organic substance capable of transporting holes. Because of this configuration, the organic EL device is adapted to inject positive charges and negative charges into the layer of the fluorescent body to perform light emission, thereby obtaining a high luminance of 1,000 cd/m$^2$ or more at a voltage of 10V or less (see Patent Document 1 and Patent Document 2)

Many improvements have been made to date for commercialization of organic EL devices. For example, high efficiency and high durability have been achieved by an electroluminescent device having a laminated structure, in which the roles of the respective layers are shared among more types of materials, and having an anode, a hole injection layer, a hole transport layer, a luminous layer, an electron transport layer, an electron injection layer, and a cathode provided on a substrate.

For a further increase in the luminous efficiency, it has been attempted to utilize triplet excitons, and the utilization of phosphorescent luminous compounds has been considered. Furthermore, devices utilizing light emission by thermally activated delayed fluorescence (TADF) have been developed. Adachi et al. from Kyushu University realized in 2011 an external quantum efficiency of 5.3% by a device using a thermally activated delayed fluorescence material.

The luminous layer can also be prepared by doping a charge transporting compound, generally called a host material, with a fluorescent compound, a phosphorescent luminous compound, or a material radiating delayed fluorescence. The selection of the organic material in the organic EL device greatly affects the characteristics of the device, such as efficiency and durability.

With the organic EL device, the charges injected from both electrodes recombine in the luminous layer to obtain light emission. For this purpose, how efficiently the charges of the holes and the electrons are passed on to the luminous layer is of importance, and the device needs to be excellent in carrier balance. Moreover, the hole injecting properties are enhanced, and the electron blocking properties of blocking electrons injected from the cathode are enhanced, whereby the probability of the holes and the electrons recombining is increased. Besides, excitons generated within the luminous layer are confined. By so doing, a high luminous efficiency can be obtained. Thus, the role of the hole transport material is so important that there has been a desire for a hole transport material having high hole injection properties, allowing marked hole mobility, possessing high electron blocking properties, and having high durability to electrons.

From the viewpoint of device life, heat resistance and amorphousness of the material are also important. A material with low heat resistance is thermally decomposed even at a low temperature by heat produced during device driving, and the material deteriorates. With a material having low amorphousness, crystallization of a thin film occurs even in a short time, and the device deteriorates. Thus, high resistance to heat and satisfactory amorphousness are required of the material to be used.

As hole transport materials so far used for organic EL devices, N,N'-diphenyl-N,N'-di(α-naphthyl)benzidine (NPD) and various aromatic amine derivatives have been known (see Patent Document 1 and Patent Document 2). NPD has satisfactory hole transport capability, but its glass transition temperature (Tg) serving as an index of heat resistance is as low as 96° C. Under high temperature conditions, therefore, device characteristics decline because of crystallization.

Among the aromatic amine derivatives described in Patent Documents 1 and 2 are compounds having excellent hole mobility of 10$^{-3}$ cm$^2$/Vs or more. Since the electron blocking properties of such aromatic amine derivatives are insufficient, however, some of electrons pass through the luminous layer, and an increase in the luminous efficiency cannot be expected. Thus, there has been a desire for a material having higher electron blocking properties, more stable in the form of a thin film, and possessing higher resistance to heat, in order to achieve an even higher efficiency.

In addition, highly durable aromatic amine derivatives have been reported in Patent Document 3. However, the aromatic amine derivatives of Patent Document 3 have been used as charge transport materials in electrophotographic photoreceptors, and examples of using them as organic EL devices have not been studied at all.

As compounds improved in characteristics such as heat resistance and hole injection properties, arylamine compounds having substituted carbazole structures have been proposed (see Patent Document 4 and Patent Document 5). In devices using these compounds as hole injection layers or hole transport layers, heat resistance and luminous efficiency have been improved. However, the improved characteristics have been still insufficient, and an even lower driving voltage and an even higher luminous efficiency are desired.

In the field of organic EL devices, as discussed above, it has been attempted to increase the yield of device preparation and improve the device characteristics, by combining materials excellent in the hole injection/transport performance, the electron injection/transport performance, thin film stability, and durability. Through these efforts, it is desired to realize a device, which is satisfactory in carrier balance, enables holes and electrons to recombine with high efficiency, has a high luminous efficiency, works at a low driving voltage, and has a long life.

PRIOR ART DOCUMENTS

Patent Documents

Patent Document 1: JP-A-H8-048656
Patent Document 2: Japanese Patent No. 3194657
Patent Document 3: Japanese Patent No. 4943840
Patent Document 4: JP-A-2006-151979

Patent Document 5: WO2008/62636
Patent Document 6: JP-T-2014-513064
Patent Document 7: Korean Unexamined Patent Publication No. 2013-060157
Patent Document 8: JP-A-H7-126615
Patent Document 9: JP-A-2005-108804

SUMMARY OF THE INVENTION

Problems to be Solved by the Invention

It is an object of the present invention to provide an organic EL device (1) high in luminous efficiency and power efficiency, (2) low in light emission start voltage, (3) low in practical driving voltage, and (4) having a long life, by combining various materials for an organic EL device, which excel in hole injection/transport performance, electron injection/transport performance, electron blocking capability, stability in a thin film state, and durability, as materials for an organic EL device with a high luminous efficiency and high durability, so that the characteristics possessed by the respective materials can be exhibited effectively.

Means for Solving the Problems

In an attempt to attain the above object, the present inventors paid attention to the facts that an arylamine-based material excelled in hole injection and transport capabilities, thin film stability, and durability, and that the luminous efficiency of a heterocyclic compound having a specific condensed ring structure was excellent. They variously combined arylamine compounds and heterocyclic compounds having condensed ring structures containing specific structures (i.e., indenoindole derivatives and carbazole derivatives) as hole transport materials and materials for the luminous layer to prepare organic EL devices, and evaluated their device characteristics. Based on the evaluations, they investigated combinations of materials which could inject and transport holes efficiently into the luminous layer and which would ensure a carrier balance suited to the characteristics of the material for the luminous layer.

The present inventors also noted that a pyrimidine derivative excelled in electron injection and transport capabilities, thin film stability, and durability. They selected a variety of pyrimidine derivatives as electron transport materials, and combined them with hole transport materials and materials for the luminous layer to prepare various organic EL devices. They diligently made evaluations of their device characteristics and, based on the evaluations, investigated combinations of materials which could increase the efficiencies of electron injection and transport into the luminous layer and which would ensure a carrier balance more suited to the characteristics of the material for the luminous layer.

Furthermore, the present inventors configured the hole transport layer to have a two-layer structure composed of a first hole transport layer and a second hole transport layer, selected the material for the first hole transport layer so that holes could be efficiently injected and transported into the luminous layer, and selected a material with excellent electron blocking properties as the material for the second hole transport layer. Through these acts, they worked out elaborate combinations, which would ensure a carrier balance, to prepare various organic EL devices, and earnestly conducted evaluations of their device characteristics.

Based on the above varieties of studies, the present inventors have accomplished the present invention.

That is, according to the present invention, there is provided an organic EL device having at least an anode, a hole transport layer, a luminous layer, an electron transport layer, and a cathode in this order, wherein the hole transport layer contains an arylamine compound represented by the following general formula (1), and the luminous layer contains an indenoindole derivative represented by the following general formula (2) or a carbazole derivative represented by the following general formula (3):

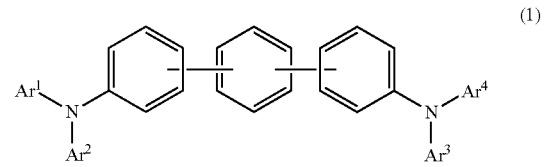

where $Ar^1$ to $Ar^4$ each represent an aromatic hydrocarbon group, an aromatic heterocyclic group, or a condensed polycyclic aromatic group,

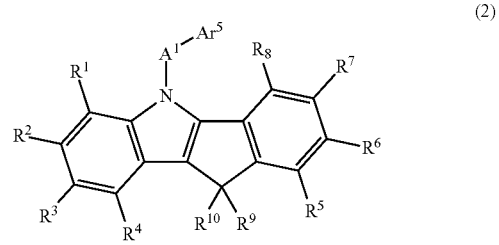

where $A^1$ represents a divalent group of an aromatic hydrocarbon, a divalent group of an aromatic heterocycle, a divalent group of a condensed polycyclic aromatic ring, or a single bond, $Ar^5$ represents an aromatic hydrocarbon group, an aromatic heterocyclic group, or a condensed polycyclic aromatic group, $R^1$ to $R^8$ each represent a hydrogen atom; a deuterium atom; a fluorine atom; a chlorine atom; a cyano group; a nitro group; an alkyl group having 1 to 6 carbon atoms; a cycloalkyl group having 5 to 10 carbon atoms; an alkenyl group having 2 to 6 carbon atoms; an alkyloxy group having 1 to 6 carbon atoms; a cycloalkyloxy group having 5 to 10 carbon atoms; an aromatic hydrocarbon group; an aromatic heterocyclic group; a condensed polycyclic aromatic group; an aryloxyl group; or a di-substituted amino group having an aromatic hydrocarbon group, an aromatic heterocyclic group, or a condensed polycyclic aromatic group as a substituent, $R^1$ to $R^4$ may be bonded to each other via a single bond, a substituted or unsubstituted methylene group, an oxygen atom, or a sulfur atom to form a ring, $R^5$ to $R^8$ may be bonded to each other via a single bond, a substituted or unsubstituted methylene group, an oxygen atom, or a sulfur atom to form a ring, part of $R^1$ to $R^4$ may be detached, and remaining group of $R^1$ to $R^4$ may be bonded to a vacancy, which has been produced by the detachment, via a substituted or unsubstituted methylene group, an oxygen atom, a sulfur atom, or a monoarylamino group to form a ring, part of $R^5$ to $R^8$ may be detached, and remaining group of $R^5$ to $R^8$ may be bonded to a vacancy, which has been produced by the detachment, via a substituted or unsubstituted methylene group, an oxygen atom, a sulfur atom, or a monoarylamino group to form a ring, and $R^9$ and $R^{10}$ each represent an alkyl group having 1 to 6 carbon atoms, an aromatic hydrocarbon group, an aromatic heterocyclic group, or a condensed polycyclic aromatic group, and $R^9$ and $R^{10}$ may be bonded to each other via a single bond, a substituted or unsubstituted methylene group, an oxygen atom, or a sulfur atom to form a ring,

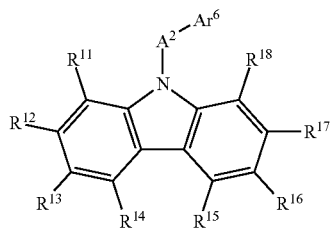

(3)

where $A^2$ represents a divalent group of an aromatic hydrocarbon, a divalent group of an aromatic heterocycle, a divalent group of a condensed polycyclic aromatic ring, or a single bond, $Ar^6$ represents an aromatic hydrocarbon group, an aromatic heterocyclic group, or a condensed polycyclic aromatic group, $R^{11}$ to $R^{18}$ each represent a hydrogen atom; a deuterium atom; a fluorine atom; a chlorine atom; a cyano group; a nitro group; an alkyl group having 1 to 6 carbon atoms; a cycloalkyl group having 5 to 10 carbon atoms; an alkenyl group having 2 to 6 carbon atoms; an alkyloxy group having 1 to 6 carbon atoms; a cycloalkyloxy group having 5 to 10 carbon atoms; an aromatic hydrocarbon group; an aromatic heterocyclic group; a condensed polycyclic aromatic group; an aryloxyl group; or a di-substituted amino group having an aromatic hydrocarbon group, an aromatic heterocyclic group, or a condensed polycyclic aromatic group as a substituent, $R^{11}$ to $R^{14}$ may be bonded to each other via a single bond, a substituted or unsubstituted methylene group, an oxygen atom, or a sulfur atom to form a ring, $R^{15}$ to $R^{18}$ may be bonded to each other via a single bond, a substituted or unsubstituted methylene group, an oxygen atom, or a sulfur atom to form a ring, part of $R^{11}$ to $R^{14}$ may be detached, and remaining group of $R^{11}$ to $R^{14}$ may be bonded to a vacancy, which has been produced by the detachment, via a substituted or unsubstituted methylene group, an oxygen atom, a sulfur atom, or a monoarylamino group to form a ring, and part of $R^{15}$ to $R^{18}$ may be detached, and remaining group of $R^{15}$ to $R^{18}$ may be bonded to a vacancy, which has been produced by the detachment, via a substituted or unsubstituted methylene group, an oxygen atom, a sulfur atom, or a monoarylamino group to form a ring.

In the organic EL device of the present invention, it is preferred that 2) the electron transport layer contains a pyrimidine derivative represented by the following general formula (4):

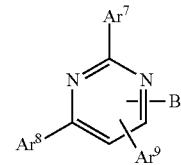

(4)

where $Ar^7$ represents an aromatic hydrocarbon group, an aromatic heterocyclic group, or a condensed polycyclic aromatic group, $Ar^8$ and $Ar^9$ each represent a hydrogen atom, an aromatic hydrocarbon group, an aromatic heterocyclic group, or a condensed polycyclic aromatic group, and $Ar^8$ and $Ar^9$ are each not a hydrogen atom at the same time, and B represents a monovalent group represented by the following structural formula (5):

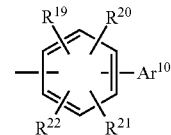

(5)

where $Ar^{10}$ represents an aromatic heterocyclic group, $R^{19}$ to $R^{22}$ each represent a hydrogen atom, a deuterium atom, a fluorine atom, a chlorine atom, a cyano group, a trifluoromethyl group, an alkyl group having 1 to 6 carbon atoms, an aromatic hydrocarbon group, an aromatic heterocyclic group, or a condensed polycyclic aromatic group, and $R^{19}$ to $R^{22}$ and $Ar^{10}$ may be bonded to each other via a single bond, a substituted or unsubstituted methylene group, an oxygen atom, or a sulfur atom to form a ring.

3) the above pyrimidine derivative is represented by the following general formula (4a):

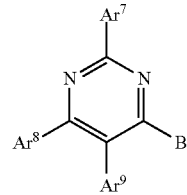

(4a)

where $Ar^7$ to $Ar^9$ and B are as defined in the general formula (4).

4) the above pyrimidine derivative is represented by the following general formula (4b):

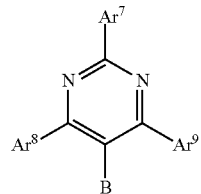

(4b)

where
Ar⁷ to Ar⁹ and B are as defined in the general formula (4).

5) in the general formula (4), B is a monovalent group represented by the following structural formula (5a):

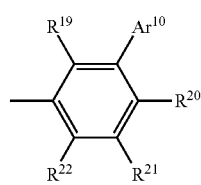

(5a)

where
Ar¹⁰ and R¹⁹ to R²² are as defined in the above structural formula (5).

6) the hole transport layer has a two-layer structure composed of a first hole transport layer and a second hole transport layer, and the second hole transport layer is located on a side of the luminous layer and contains the arylamine compound represented by the aforementioned general formula (1), 7) the luminous layer contains a red luminous material, 8) the luminous layer contains a phosphorescent luminous material, and 9) the above phosphorescent luminous material is a metal complex containing iridium or platinum.

Effects of the Invention

The present invention uses the arylamine compound having the specific structure that is excellent in the hole injection/transport performance, the thin film stability, and the durability and that can effectively exhibit the roles of injecting and transporting holes. This arylamine compound is combined with the luminous material having an excellent luminous efficiency, whereby holes can be efficiently injected and transported into the luminous layer, with the result that an organic EL device having a high efficiency, involving a low driving voltage, and having a long life can be realized. In consideration of the carrier balance, moreover, a combination of the arylamine compound having the specific structure and the material for the luminous layer having the specific structure is further combined with the specific electron transport material. By so doing, an organic EL device with a high efficiency, a low driving voltage, and especially a long life can be achieved. Furthermore, the hole transport layer is configured with the two-layer structure composed of the first hole transport layer and the second hole transport layer, and two types of arylamine compounds having specific structures are combined in view of the carrier balance and the characteristics of the materials, and used for the two layers. In this case, an organic EL device having an even longer life can be turned into reality. According to the present invention, as described above, the luminous efficiency, driving voltage, and durability in particular, of the conventional organic EL device can be improved.

MODE FOR CARRYING OUT THE INVENTION

Figure 1:
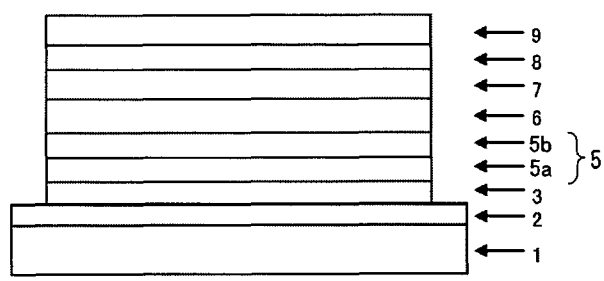
FIG. 1 is a view showing the configurations of organic EL devices of Examples 1 to 12 and Comparative Examples 1 to 3.
Figure 2:
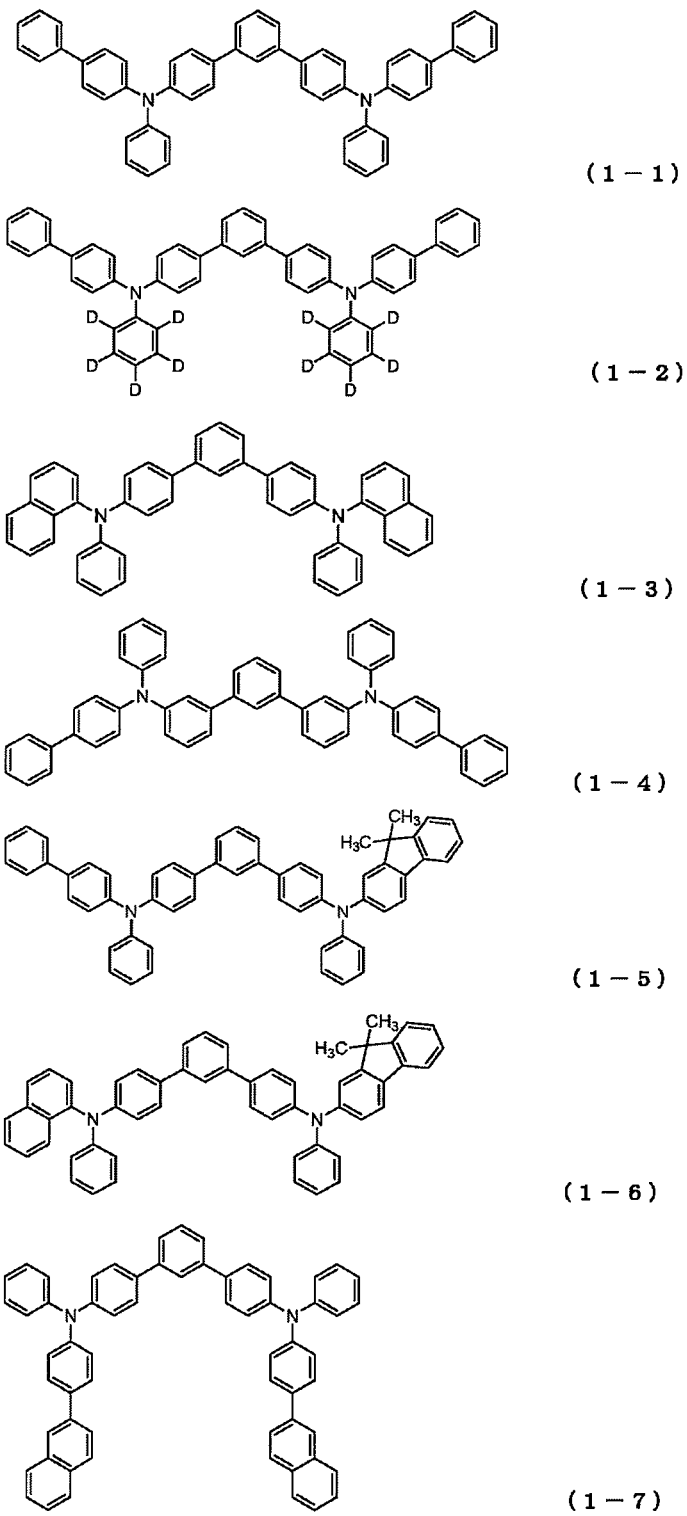
FIG. 2 is a view showing the structural formulas of Compounds (1-1) to (1-7) which are arylamine compounds of the general formula (1).
Figure 3:
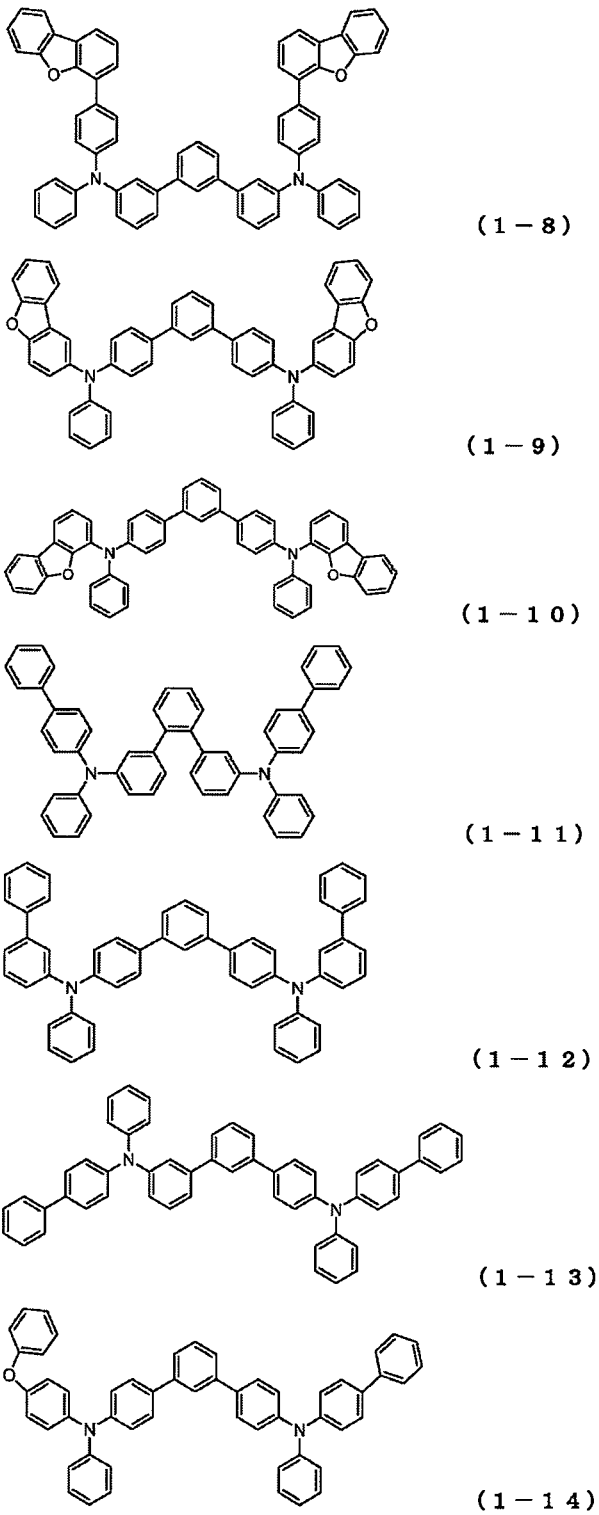
FIG. 3 is a view showing the structural formulas of Compounds (1-8) to (1-14) which are arylamine compounds of the general formula (1).
Figure 4:
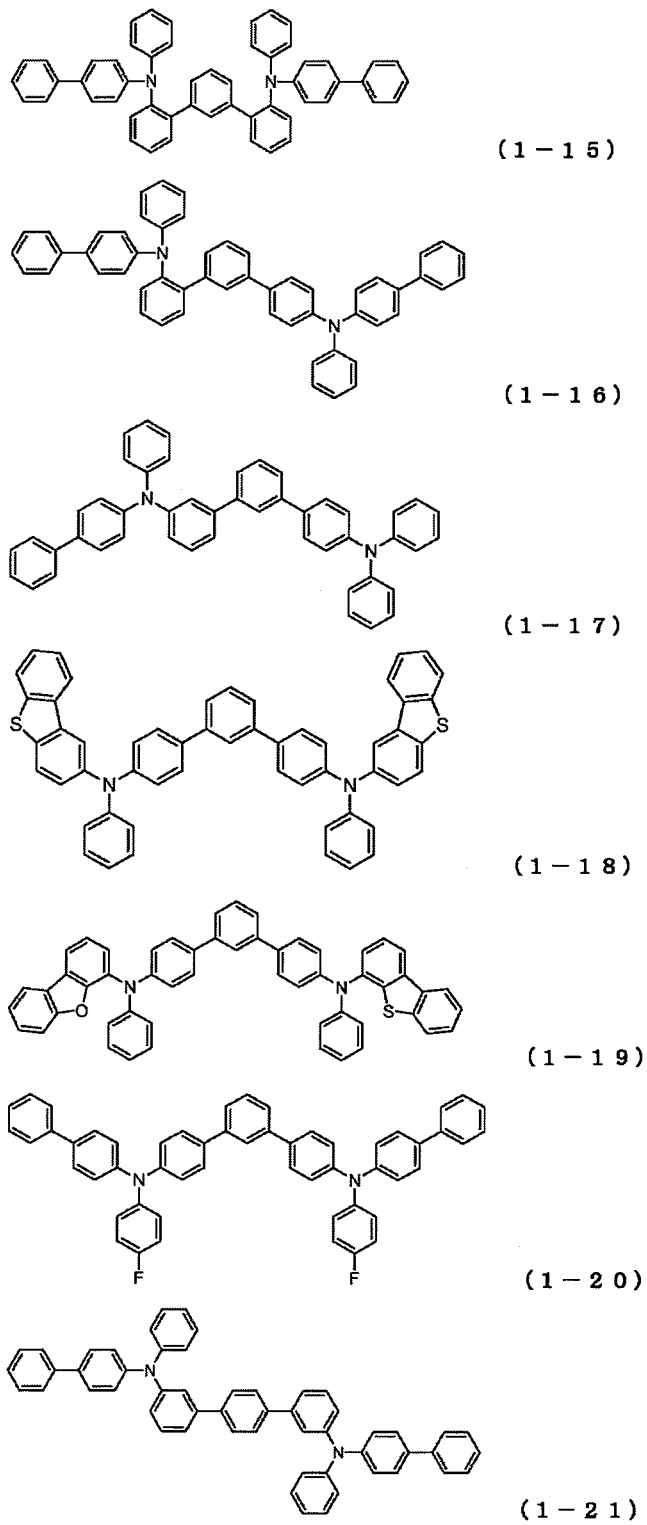
FIG. 4 is a view showing the structural formulas of Compounds (1-15) to (1-21) which are arylamine compounds of the general formula (1).
Figure 5:
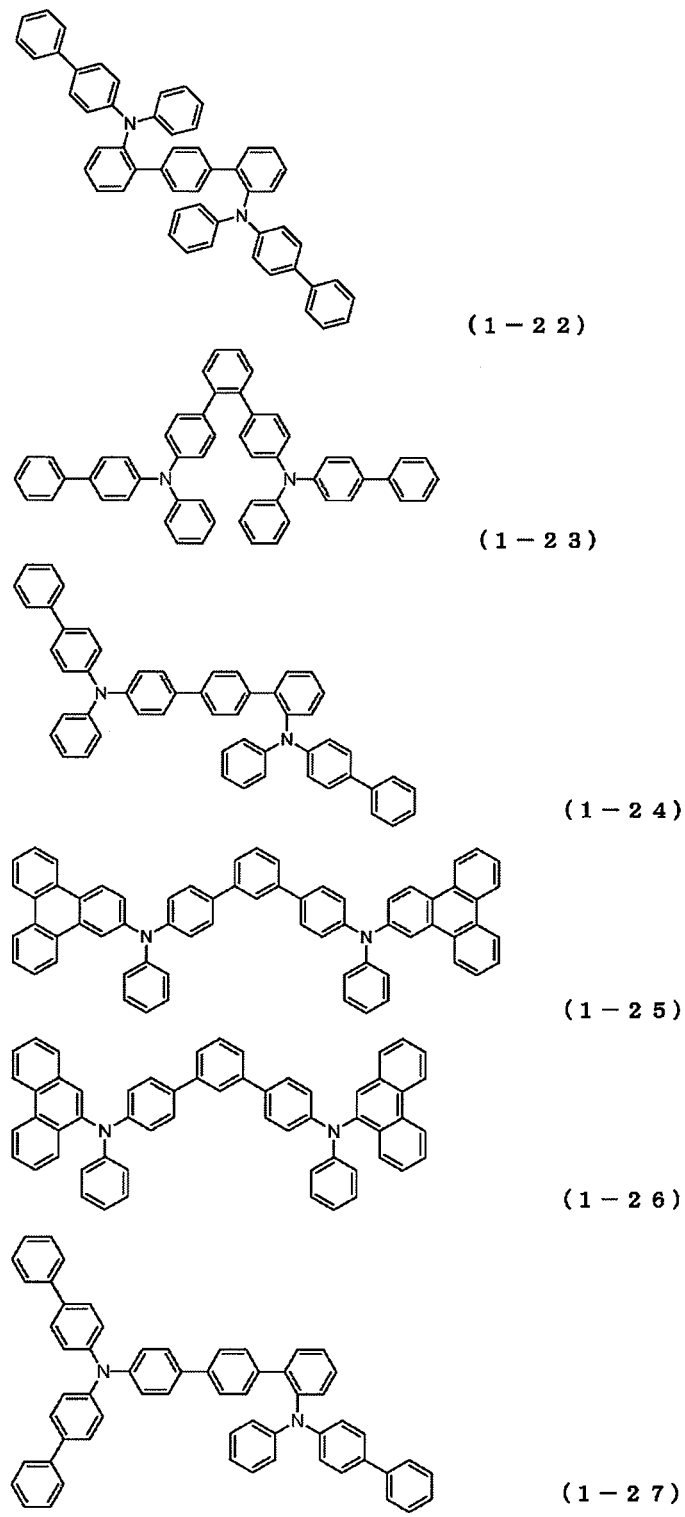
FIG. 5 is a view showing the structural formulas of Compounds (1-22) to (1-27) which are arylamine compounds of the general formula (1).
Figure 6:
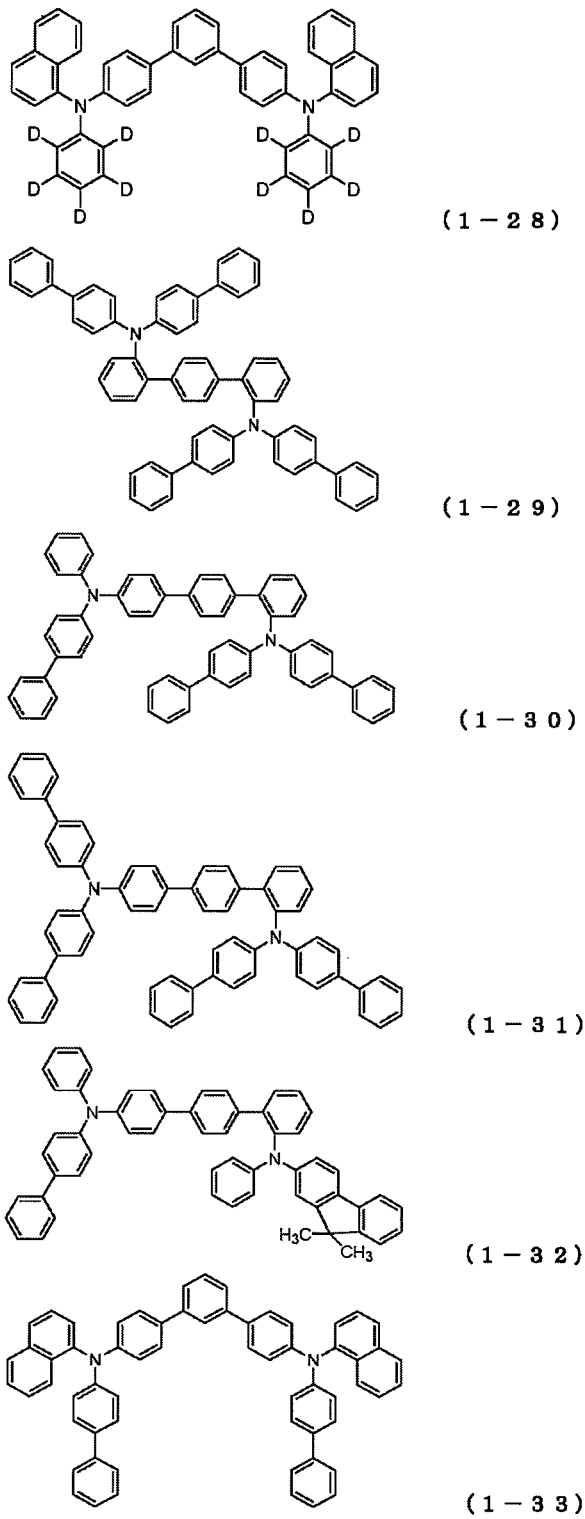
FIG. 6 is a view showing the structural formulas of Compounds (1-28) to (1-33) which are arylamine compounds of the general formula (1).
Figure 7:
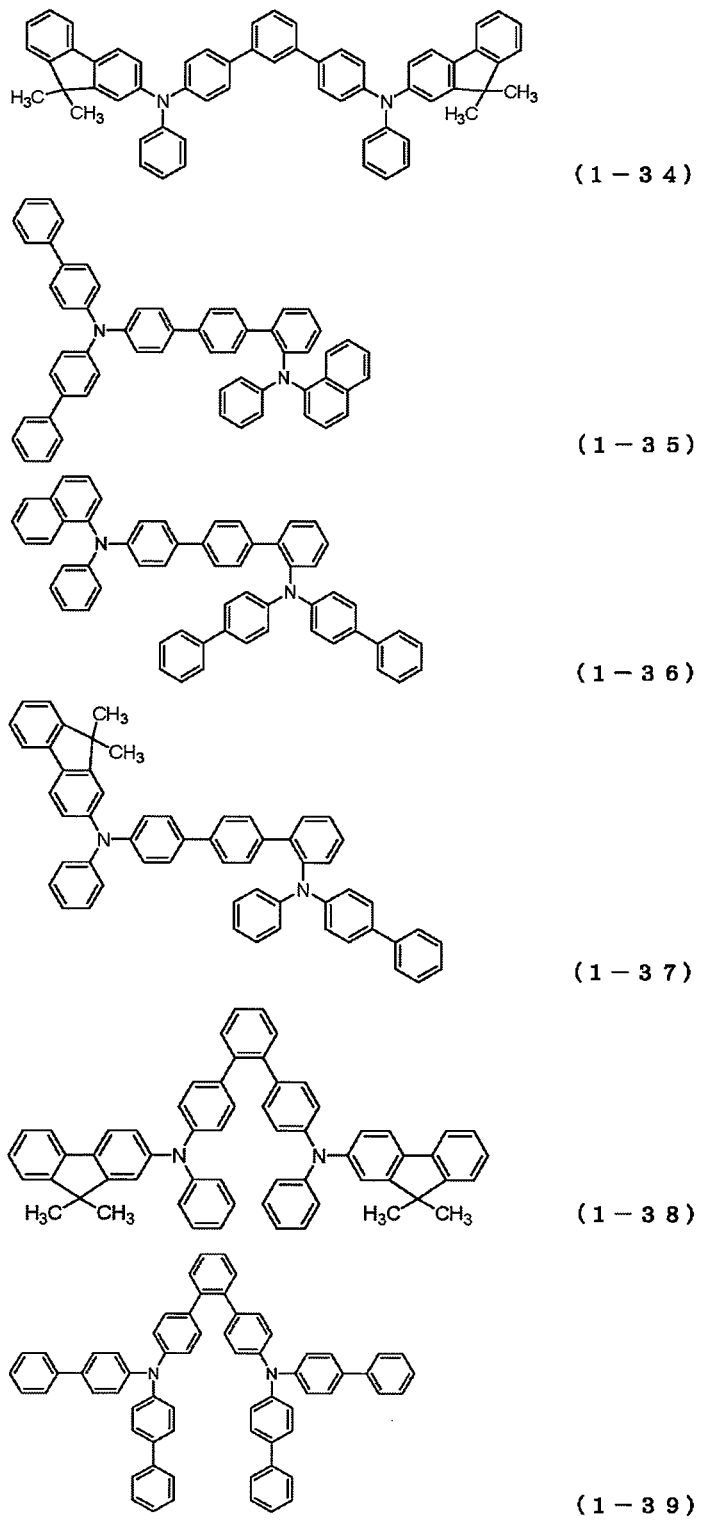
FIG. 7 is a view showing the structural formulas of Compounds (1-34) to (1-39) which are arylamine compounds of the general formula (1).
Figure 8:
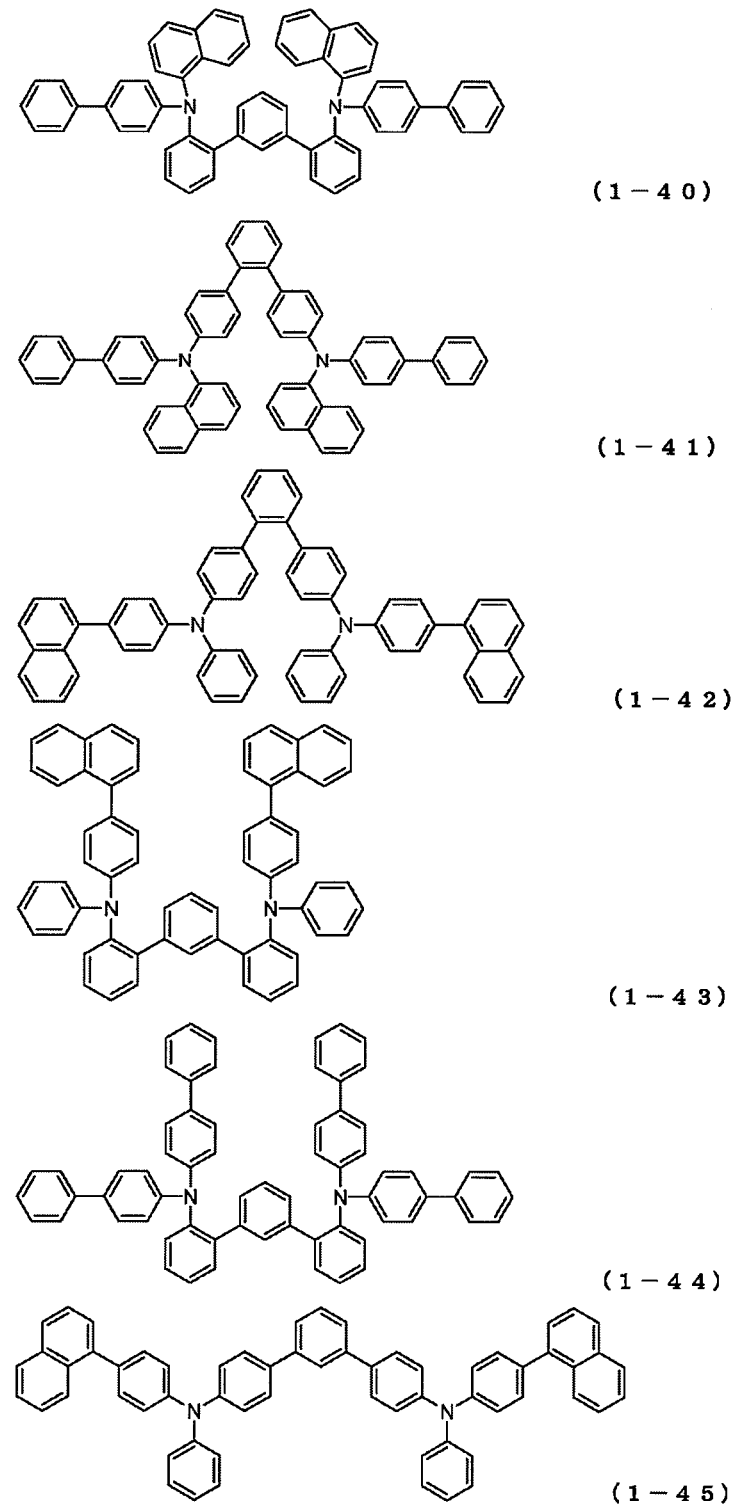
FIG. 8 is a view showing the structural formulas of Compounds (1-40) to (1-45) which are arylamine compounds of the general formula (1).
Figure 9:
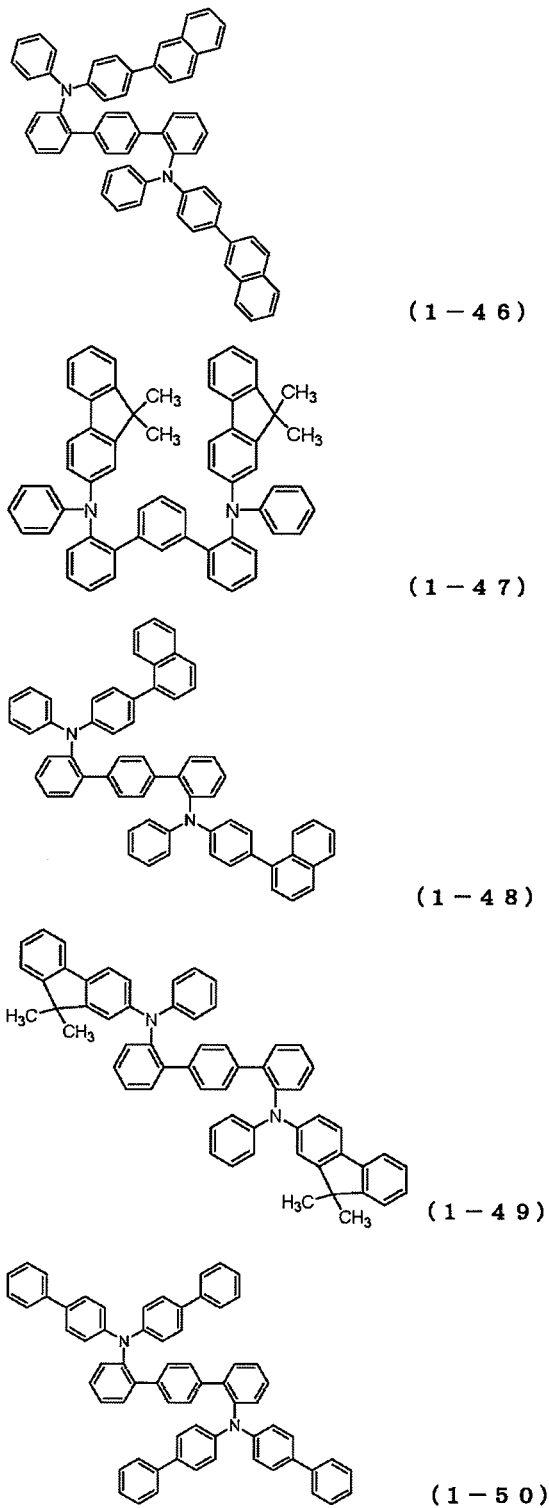
FIG. 9 is a view showing the structural formulas of Compounds (1-46) to (1-50) which are arylamine compounds of the general formula (1).
Figure 10:
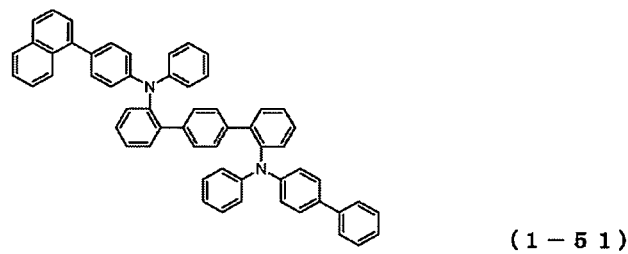
FIG. 10 is a view showing the structural formulas of Compounds (1-51) to (1-55) which are arylamine compounds of the general formula (1).
Figure 10:
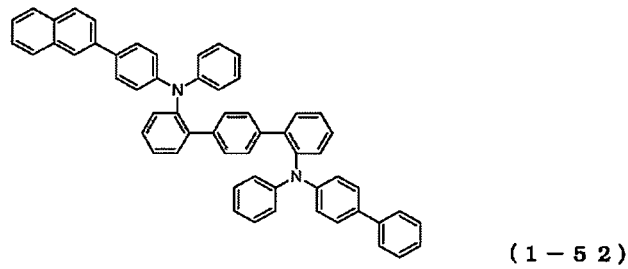
Figure 10:
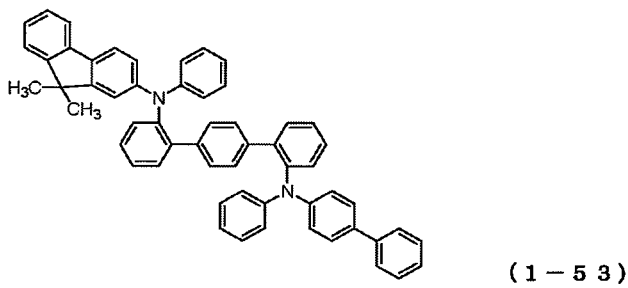
Figure 10:
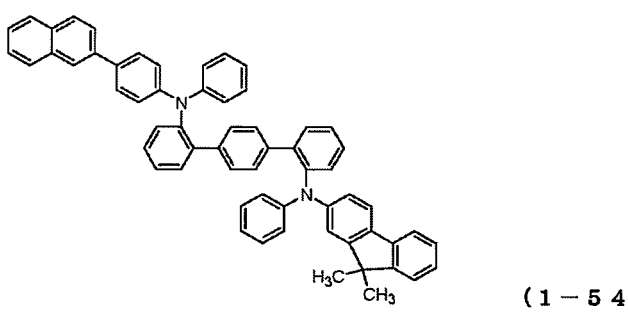
Figure 10:
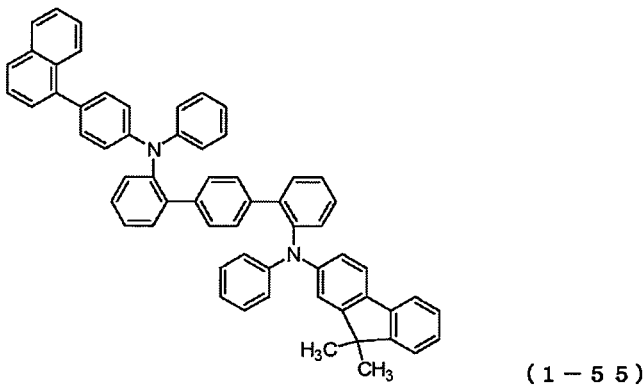
Figure 11:
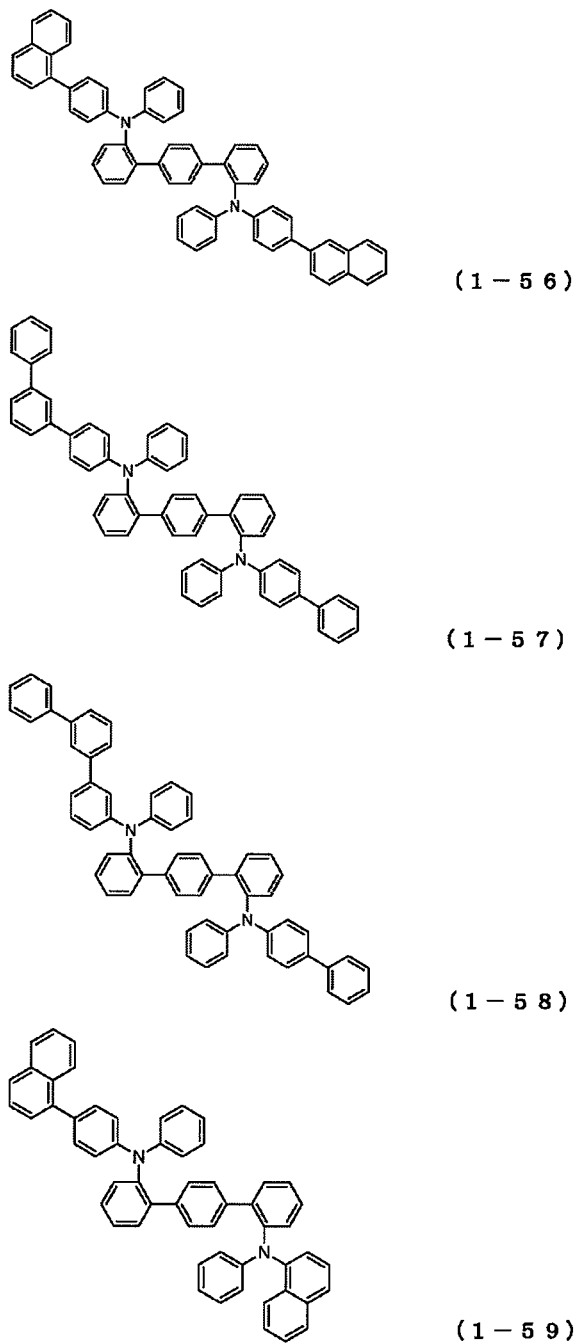
FIG. 11 is a view showing the structural formulas of Compounds (1-56) to (1-59) which are arylamine compounds of the general formula (1).
Figure 12:
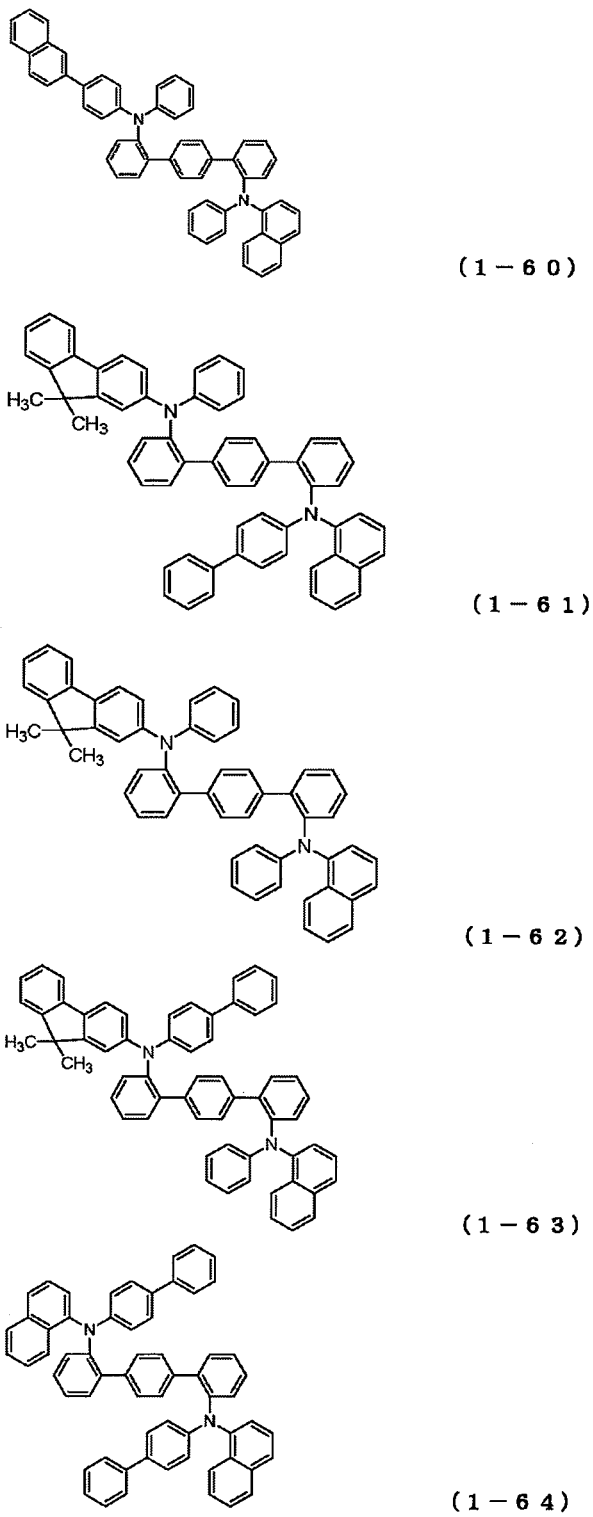
FIG. 12 is a view showing the structural formulas of Compounds (1-60) to (1-64) which are arylamine compounds of the general formula (1).
Figure 13:
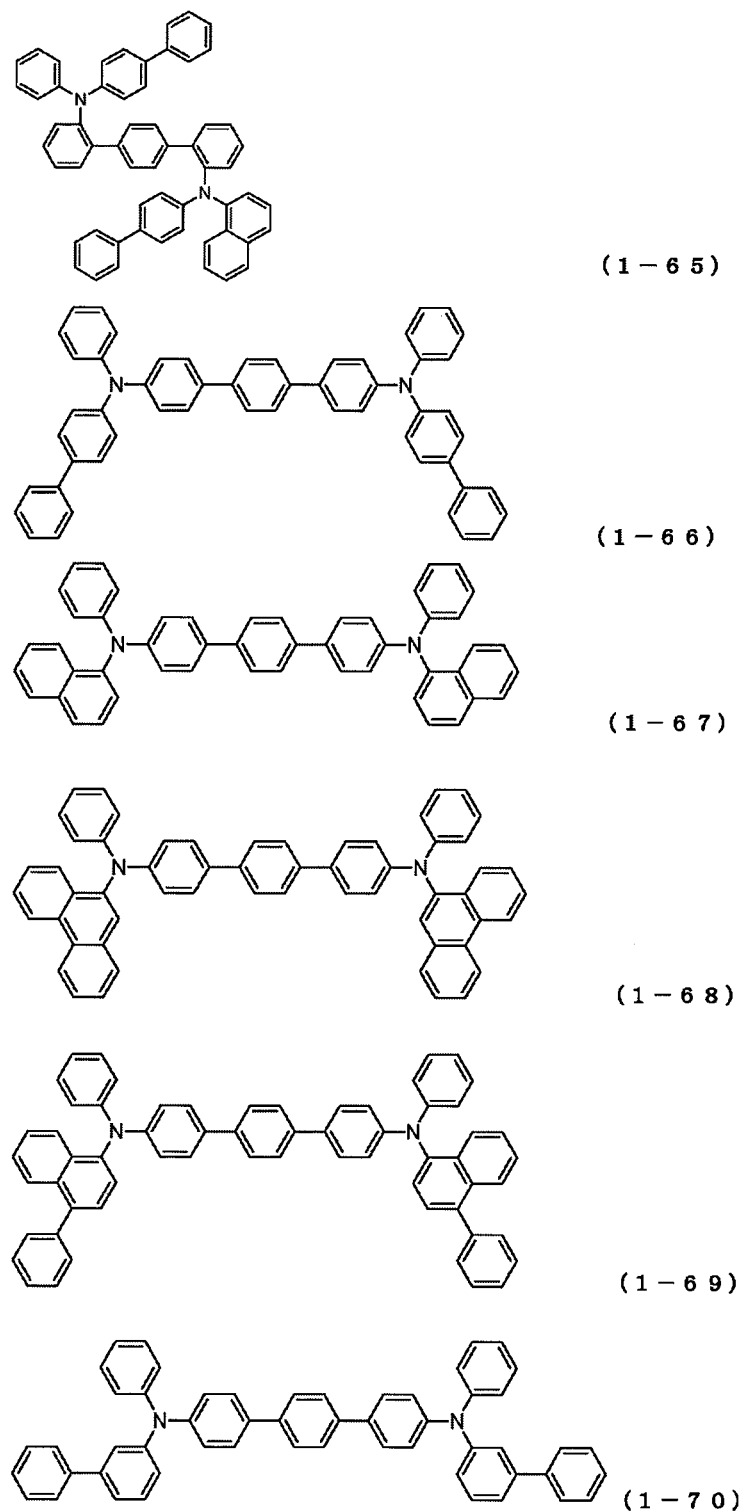
FIG. 13 is a view showing the structural formulas of Compounds (1-65) to (1-70) which are arylamine compounds of the general formula (1).
Figure 14:
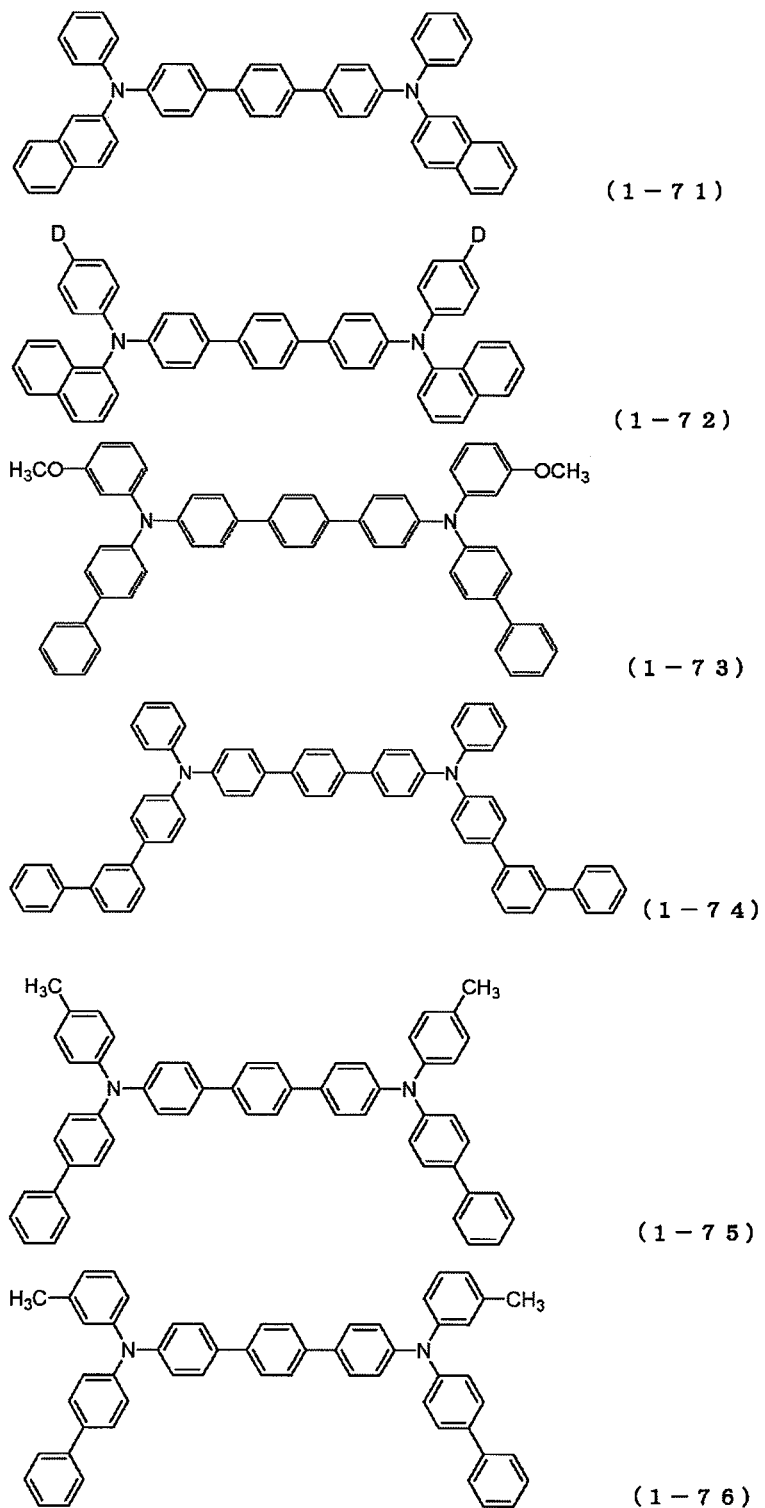
FIG. 14 is a view showing the structural formulas of Compounds (1-71) to (1-76) which are arylamine compounds of the general formula (1).
Figure 15:
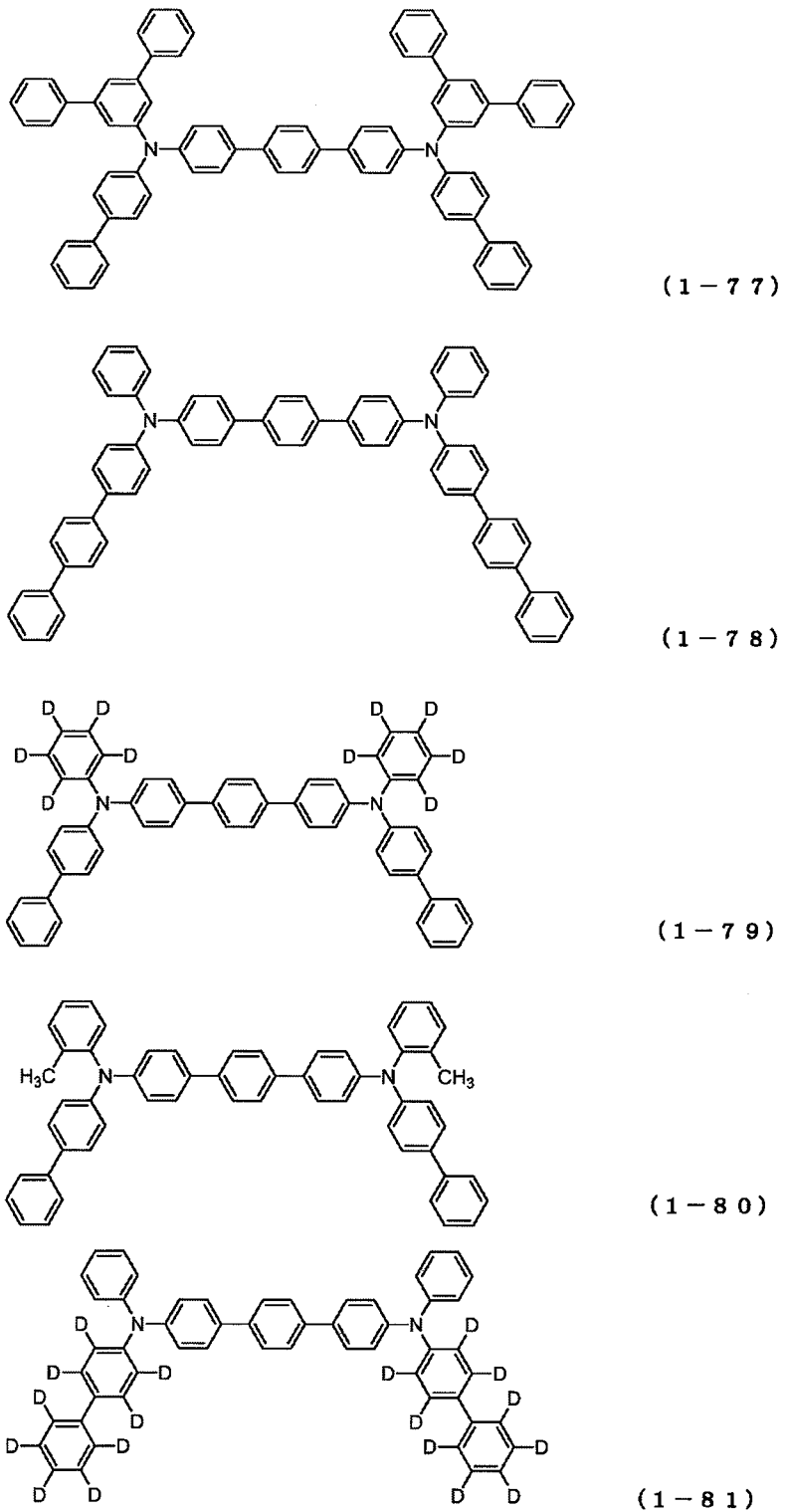
FIG. 15 is a view showing the structural formulas of Compounds (1-77) to (1-81) which are arylamine compounds of the general formula (1).
Figure 16:
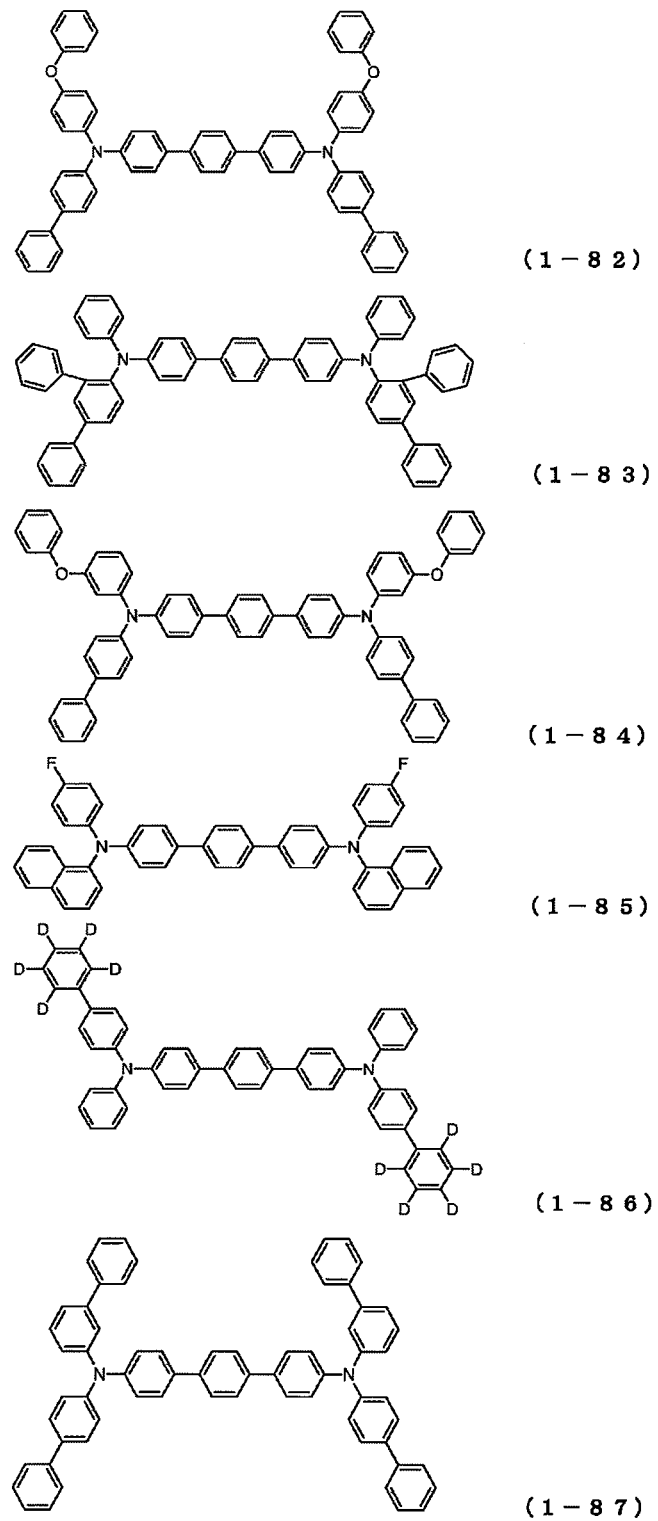
FIG. 16 is a view showing the structural formulas of Compounds (1-82) to (1-87) which are arylamine compounds of the general formula (1).
Figure 17:
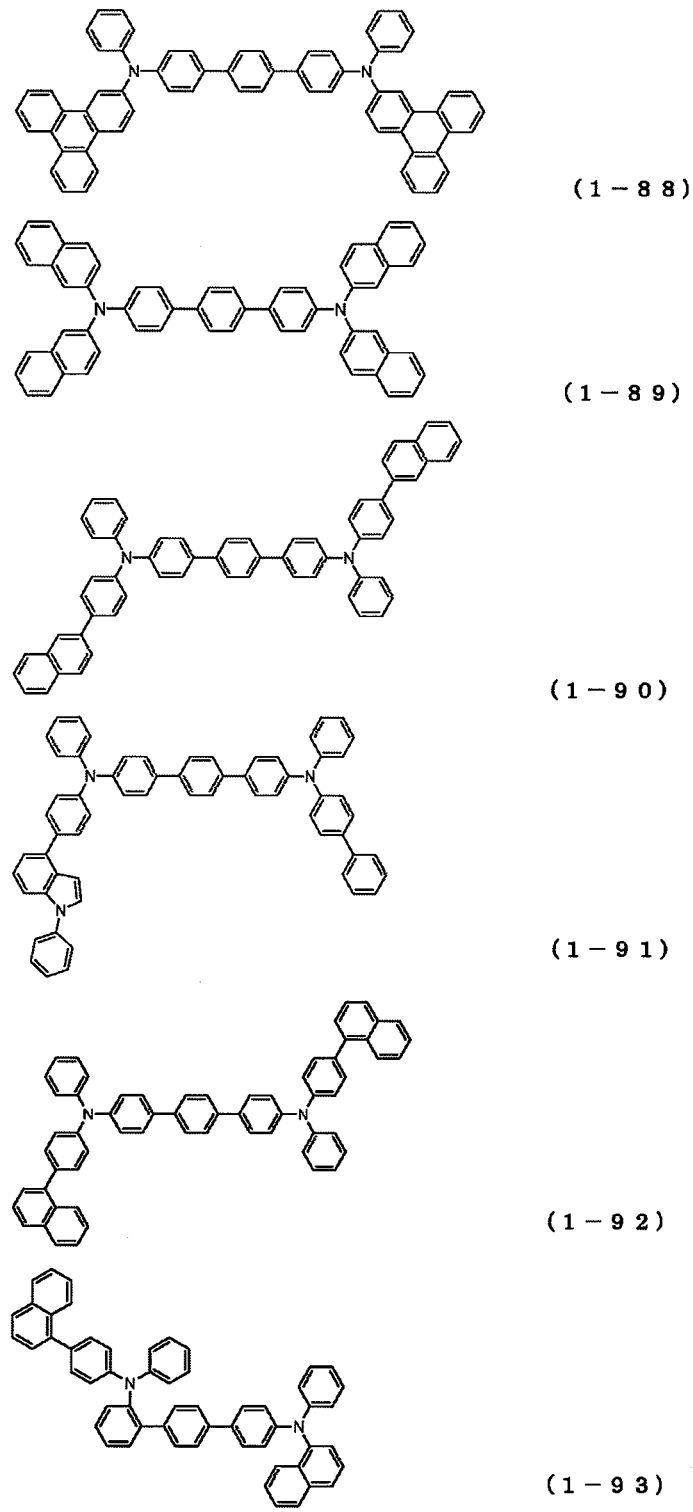
FIG. 17 is a view showing the structural formulas of Compounds (1-88) to (1-93) which are arylamine compounds of the general formula (1).
Figure 18:
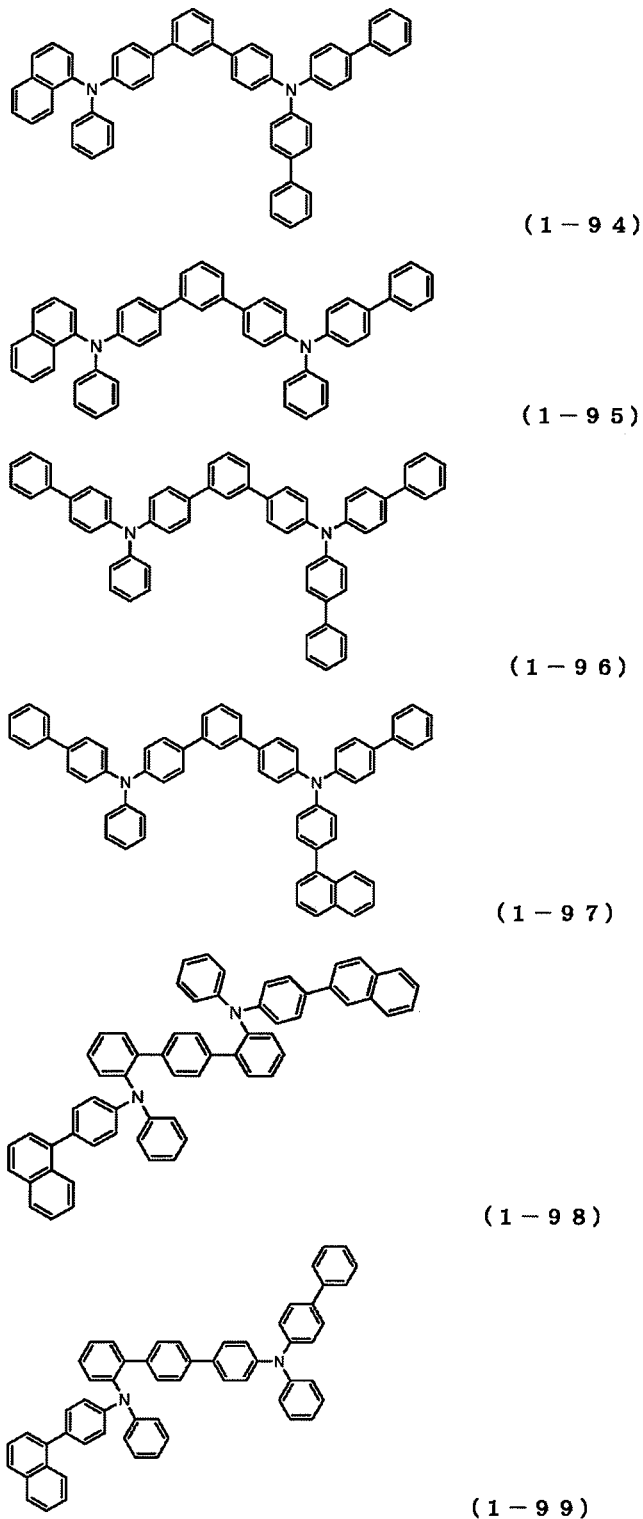
FIG. 18 is a view showing the structural formulas of Compounds (1-94) to (1-99) which are arylamine compounds of the general formula (1).
Figure 19:
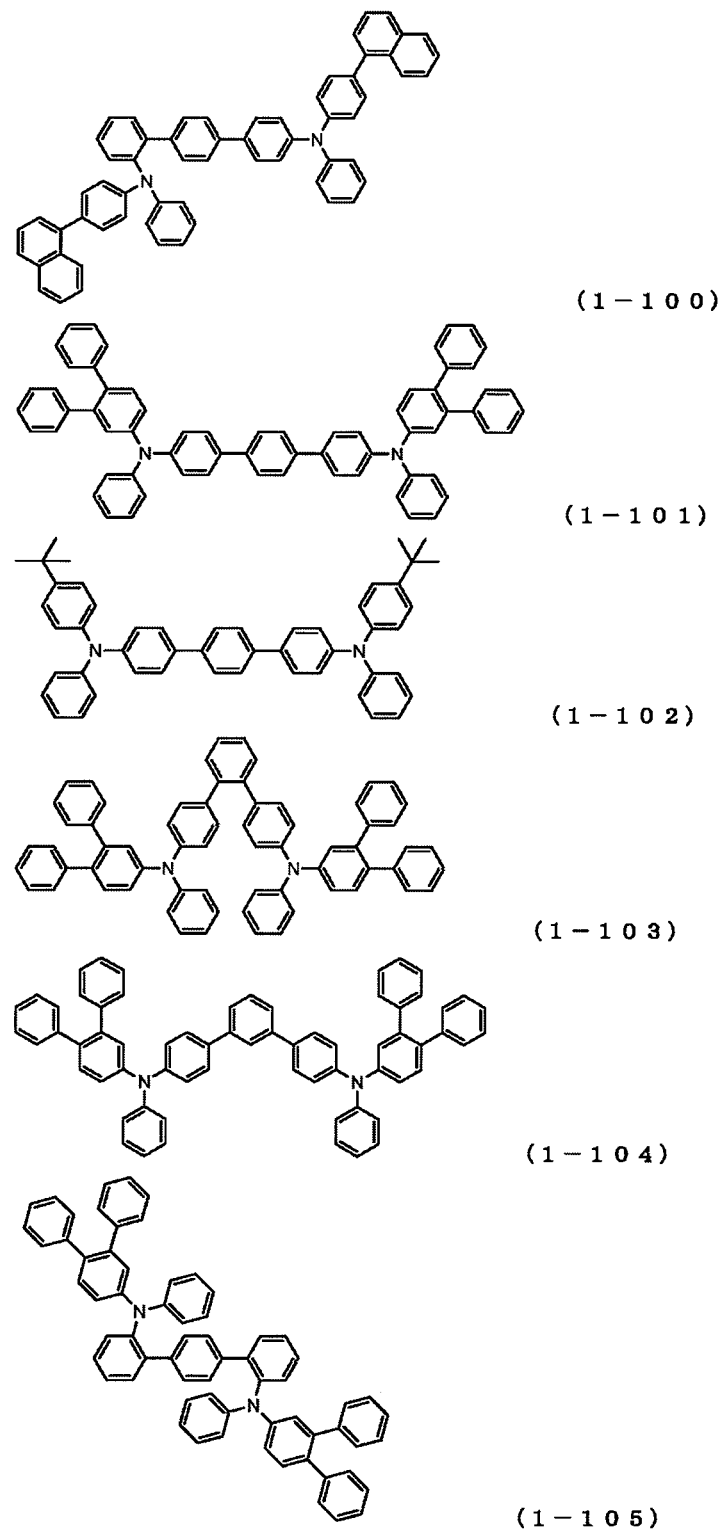
FIG. 19 is a view showing the structural formulas of Compounds (1-100) to (1-105) which are arylamine compounds of the general formula (1).

The organic EL device of the present invention has a basic structure in which an anode, a hole transport layer, a luminous layer, an electron transport layer, and a cathode are provided in this sequence on a substrate such as a glass substrate or a transparent plastic substrate (e.g., polyethylene terephthalate substrate). As long as it has such a basic structure, its layer structure can take various forms. For example, an electron blocking layer can be provided between the hole transport layer and the luminous layer, a hole blocking layer can be provided between the luminous layer and the electron transport layer, or an electron injection layer can be provided between the electron transport layer and the cathode. Moreover, some of the organic layers can be omitted, or can be allowed to concurrently serve as the other layers. For example, a layer concurrently serving as the hole injection layer and the hole transport layer can be formed, or a layer concurrently serving as the electron injection layer and the electron transport layer can be formed. Furthermore, a configuration in which two or more of the organic layers having the same function are laminated can be adopted. Concretely, it is also possible to adopt a configuration in which two of the hole transport layers are laminated, a configuration in which two of the luminous layers are laminated, or a configuration in which two of the electron transport layers are laminated. In the present invention, it is preferred to configure the hole transport layer to have two layers laminated together, i.e., a first hole transport layer and a second hole transport layer. FIG. 1, for example, shows the layer configuration adopted in the Examples to be described later. In this layer configuration, a transparent anode 2, a hole injection layer 3, a hole transport layer 5, a luminous layer 6, an electron transport layer 7, an electron injection layer 8, and a cathode 9 are formed in this sequence on a glass substrate 1, the hole transport layer 5 being composed of two layers, a first hole transport layer 5a and a second hole transport layer 5b.

The respective layers constituting the organic EL device of the present invention will be described below.

<Anode 2>

The anode 2 is formed on the transparent substrate 1 by vapor deposition of an electrode material having a high work function, such as ITO or gold.

<Hole injection layer 3>

The hole injection layer 3 may be provided, if necessary, between the anode 2 and the hole transport layer 5. For the hole injection layer 3, a publicly known material can be used, for example, triphenylamine derivatives of starburst type; various triphenylamine tetramers; porphyrin compounds typified by copper phthalocyanine; acceptor type heterocyclic compounds such as hexacyanoazatriphenylene; and coating type polymeric materials. Moreover, arylamine compounds of the general formula (1) to be described later, triarylamine compounds of the general formula (6) to be described later, or triarylamine compounds of the general formula (7) to be described later can also be used. For the hole injection layer 3, it is preferred to use the triarylamine compounds of the general formula (6) or the general formula (7), because these (tri)arylamine compounds have high hole mobility. If the (tri)arylamine compounds of the general formula (1), (6) or (7) are used for the hole injection layer 3, however, the composition of the hole injection layer 3 and the composition of the hole transport layer 5 must be different.

Any of these materials may be subjected singly to film formation, but may be mixed with other materials and subjected to film formation. Materials p-doped with tris (bromophenyl)aminium hexachloroantimonate, radialene derivatives (see WO2014/009310) or the like, or polymeric compounds containing the structures of benzidine derivatives such as TPD in their partial structures may also be used.

When thin film formation is performed by a publicly known method such as vapor deposition, a spin coat method or an ink jet method with the use of any of the above materials, the hole injection layer 3 can be obtained. Each of the layers to be described below can similarly be obtained by film formation performed using a publicly known method such as vapor deposition, spin coating, or ink jetting.

<Hole transport layer 5>

The hole transport layer 5 is provided between the above anode 2 and the luminous layer 6. In the present invention, this hole transport layer 5 contains an arylamine compound represented by the following general formula (1) (may herein be referred to simply as an "arylamine compound of the general formula (1)"). This is because the arylamine compound of the general formula (1) has high hole mobility, and can thus increase the efficiency of hole transport from the hole transport layer to the luminous layer.

Arylamine compound of the general formula (1):

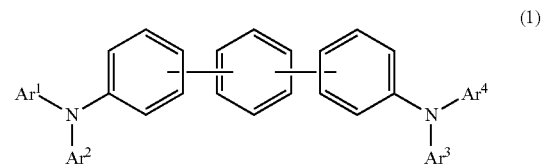

In the general formula (1), $Ar^1$ to $Ar^4$ each represent an aromatic hydrocarbon group, an aromatic heterocyclic group, or a condensed polycyclic aromatic group. Examples of the aromatic hydrocarbon group, the aromatic heterocyclic group, or the condensed polycyclic aromatic group, represented by $Ar^1$ to $Ar^4$, include a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, an isoquinolyl group, a quinazolinyl group, a benzofuranyl group, a benzothienyl group, an indolyl group, a carbazolyl group, a benzimidazolyl group, a benzoxazolyl group, a benzothiazolyl group, a pyridopyrimidinyl group, a naphthyridinyl group, a quinoxalinyl group, a benzimidazolyl group, a pyrazolyl group, a naphthopyrimidinyl group, a dibenzofuranyl group, a dibenzothienyl group, a naphthyridinyl group, a phenanthrolinyl group, an acridinyl group, a carbolinyl group, a benzoquinazolinyl group and the like.

The aromatic hydrocarbon group, the aromatic heterocyclic group, or the condensed polycyclic aromatic group, represented by $Ar^1$ to $Ar^4$, may each be unsubstituted, but may each have a substituent. The substituent can be exemplified by the following groups, in addition to a deuterium atom, a cyano group, and a nitro group:

a halogen atom, for example, a fluorine atom, a chlorine atom, a bromine atom, an iodine atom or the like;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, an n-hexyl group or the like;

an alkyloxy group having 1 to 6 carbon atoms, for example, a methyloxy group, an ethyloxy group, a propyloxy group or the like;

an alkenyl group, for example, a vinyl group, an allyl group or the like;

an aryloxy group, for example, a phenyloxy group, a tolyloxy group or the like;

an arylalkyloxy group, for example, a benzyloxy group, a phenethyloxy group or the like;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group or the like;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a carbolinyl group or the like;

an arylvinyl group, for example, a styryl group, a naphthylvinyl group or the like; and an acyl group, for example, an acetyl group, a benzoyl group or the like;

The alkyl group having 1 to 6 carbon atoms, the alkyloxy group having 1 to 6 carbon atoms, and the alkenyl group may be straight-chain or branched. Any of the above exemplary substituents may be further substituted by the above exemplary substituent. The above exemplary substituents may be present independently of each other in order to avoid formation of a ring. However, they may be bonded to each other via a single bond, a substituted or unsubstituted methylene group, an oxygen atom, or a sulfur atom to form a ring.

As $Ar^1$ to $Ar^4$, an aromatic hydrocarbon group, an oxygen-containing aromatic heterocyclic group, or a condensed polycyclic aromatic group is preferred, and a phenyl group, a biphenylyl group, a terphenylyl group, a naphthyl group, a phenanthrenyl group, a triphenylenyl group, a fluorenyl group, or a dibenzofuranyl group is more preferred.

As the substituent that the aromatic hydrocarbon group, the aromatic heterocyclic group, or the condensed polycyclic aromatic group represented by $Ar^1$ to $Ar^4$ may have, a deuterium atom, an alkyl group having 1 to 6 carbon atoms, an alkenyl group having 2 to 6 carbon atoms, an aromatic hydrocarbon group, an oxygen-containing aromatic heterocyclic group, or a condensed polycyclic aromatic group is preferred, and a deuterium atom, a phenyl group, a biphenylyl group, a naphthyl group, a dibenzofuranyl group, or a vinyl group is more preferred. An embodiment in which $Ar^1$ to $Ar^4$ bind to each other via a single bond to form a condensed aromatic ring is also preferred.

An embodiment in which $Ar^1$ and $Ar^2$ are different groups, or $Ar^3$ and $Ar^4$ are different groups is preferred, and an embodiment in which $Ar^1$ and $Ar^2$ are different groups, and $Ar^3$ and $Ar^4$ are different groups is more preferred. The term "different" includes not only a case in which the basic structures are different, but also a case in which the basic structures are the same, but substituents are different, and a case in which the basic structures and the substituents are the same, but the positions of the substituents are different.

As the mode of binding of the phenylene groups in the general formula (1), a skeleton in which all the bonds are 1,4-bonds (e.g., 4,4"-diamino-[1,1':4',1"]terphenyl skeleton) is not preferred, but a skeleton containing 1,2-bonds or 1,3-bonds is preferred, from the viewpoint of thin film stability which influences the device life. That is, a skeleton in which the phenylene groups are not linearly linked, as shown below, is preferred:

4,4"-diamino-[1,1':3',1"]terphenyl skeleton;
3,3"-diamino-[1,1':3',1"]terphenyl skeleton;
2,2"-diamino-[1,1':3',1"]terphenyl skeleton;
4,4"-diamino-[1,1':2',1"]terphenyl skeleton;
3,3"-diamino-[1,1':2',1"]terphenyl skeleton;
2,2"-diamino-[1,1':2',1"]terphenyl skeleton;
2,4"-diamino-[1,1':4',1"]terphenyl skeleton;
2,2"-diamino-[1,1':4',1"]terphenyl skeleton;
3,3"-diamino-[1,1':4',1"]terphenyl skeleton.

Particularly, an arylamine compound represented by the following general formula (1a-a), (1a-b), (1b-a), (1c-a), (1c-b) or (1c-c) is preferred.

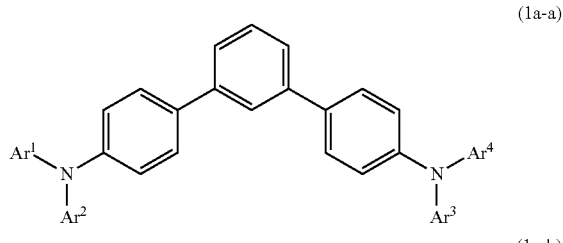
(1a-a)

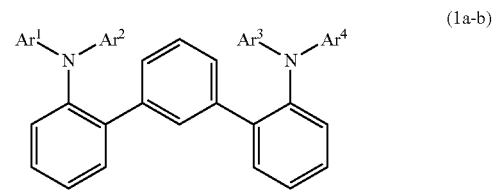
(1a-b)

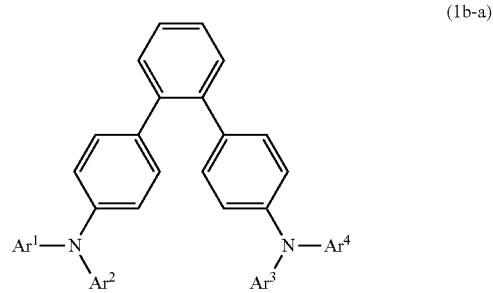
(1b-a)

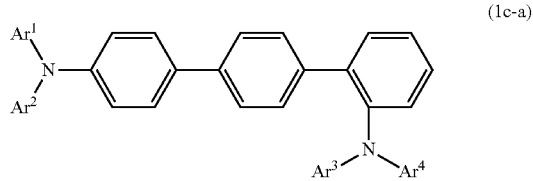
(1c-a)

(1c-b)

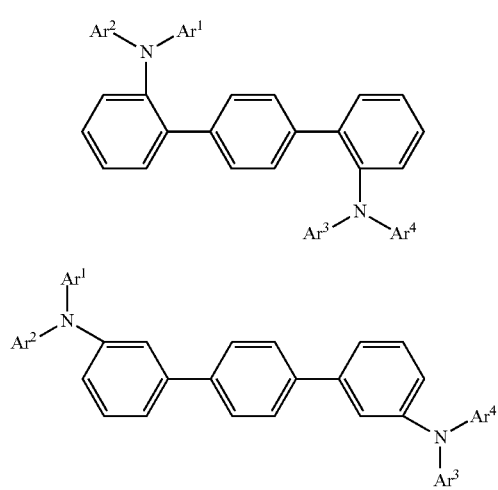

(1c-c)

where Ar¹ to Ar⁴ have the meanings as defined in the general formula (1).

Concrete examples of the preferred compounds among the arylamine compounds represented by the general formula (1) are shown in FIGS. 2 to 19, but such arylamine compounds are not limited to these compounds. D in the structural formulas denotes deuterium.

Of the exemplary compounds shown in FIGS. 2 to 19, the compounds corresponding to the formula (1a-a) are (1-1) to (1-3), (1-5) to (1-7), (1-9) to (1-10), (1-12), (1-14), (1-18) to (1-20), (1-25) to (1-26), (1-28), (1-33) to (1-34), (1-45), (1-94) to (1-97) and (1-104). The compounds corresponding to the formula (1a-b) are (1-15), (1-40), (1-43) to (1-44) and (1-47). The compounds corresponding to the formula (1b-a) are (1-23), (1-38) to (1-39), (1-41) to (1-42) and (1-103). The compounds corresponding to the formula (1c-a) are (1-24), (1-27), (1-30) to (1-32), (1-35) to (1-37), (1-93) and (1-99) to (1-100). The compounds corresponding to the formula (1c-b) are (1-22), (1-29), (1-46), (1-48) to (1-65), (1-98) and (1-105) The compound corresponding to the formula (1c-c) is (1-21).

The arylamine compound represented by the above general formula (1) can be synthesized using a publicly known method such as Suzuki coupling.

The purification of the arylamine compound represented by the general formula (1) can be performed, for example, by purification using a column chromatograph, adsorption purification using silica gel, activated carbon, activated clay, or the like, recrystallization or crystallization using a solvent, or sublimation purification. Like the arylamine compounds represented by the general formula (1), the other compounds for use in the organic EL device of the present invention are also obtainable by purification using a column chromatograph, adsorption purification using silica gel, activated carbon, activated clay, or the like, or purification by recrystallization or crystallization using a solvent, followed by final sublimation purification. The identification of the compounds can be made by NMR analysis. As the physical properties, the glass transition temperature (Tg) and the work function can be measured.

The glass transition temperature (Tg) serves as an index to stability in a thin film state. The glass transition temperature (Tg) can be measured by a high sensitivity differential scanning calorimeter (DSC3100SA, produced by Bruker AXS K.K.) using a powder.

The work function serves as an index to hole transport properties. The work function can be measured by preparing a 100 nm thin film on an ITO substrate, and making a measurement using an ionization potential measuring device (PYS-202, produced by Sumitomo Heavy Industries, Ltd.).

The arylamine compound of the general formula (1) may be subjected singly to film formation, but may be mixed with other materials and subjected to film formation. The hole transporting material that can be mixed with or used in combination with the arylamine compound of the general formula (1) can be exemplified by the following:

benzidine derivatives, for example,
N,N'-diphenyl-N,N'-di(m-tolyl)benzidine (TPD),
N,N'-diphenyl-N,N'-di(α-naphthyl)benzidine (NPD), and
N,N,N',N'-tetrabiphenylylbenzidine;

1,1-bis[4-(di-4-tolylamino)phenyl]cyclohexane (TAPC);

triarylamine compounds which have two triarylamine structures in the molecule, and in which the triarylamine structures are linked to each other via a divalent group containing no hetero-atom, or a single bond, for example, triarylamine compounds represented by the general formula (6) to be described later;

triarylamine compounds which have four triarylamine structures in the molecule, and in which the triarylamine structures are linked to each other via divalent groups containing no hetero-atom, or single bonds, for example, triarylamine compounds represented by the general formula (7) to be described later; and various triphenylamine trimers.

Furthermore, materials p-doped with tris(bromophenyl) aminium hexachloroantimonate, radialene derivatives (see WO2014/009310) or the like, or polymeric compounds containing the structures of benzidine derivatives such as TPD in their partial structures may also be used in combination.

In the present invention, the hole transport layer 5 preferably has a two-layer structure composed of the first hole transport layer 5a located on a side of the anode 2 and the second hole transport layer 5b located on a side of the luminous layer 6, for example, as shown in FIG. 1. The hole transport layer 5 with such a two-layer structure will be described later.

<Luminous layer 6>

In the present invention, it is important for the luminous layer 6 to contain an indenoindole derivative represented by the following general formula (2) (may herein be referred to simply as an "indenoindole derivative of the general formula (2)"), or a carbazole derivative represented by the following general formula (3) (may herein be referred to simply as a "carbazole derivative of the general formula (3)").

Indenoindole Derivative of the General Formula (2)

(2)

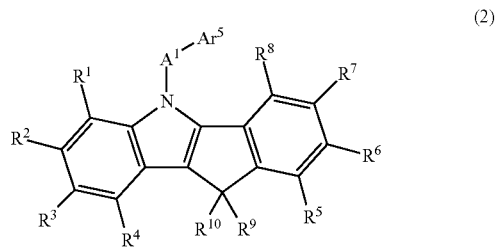

($A^1$)

In the general formula (2), $A^1$ represents a divalent group of an aromatic hydrocarbon, a divalent group of an aromatic heterocycle, a divalent group of a condensed polycyclic aromatic ring, or a single bond. The divalent group of an aromatic hydrocarbon, the divalent group of an aromatic heterocycle, or the divalent group of a condensed polycyclic aromatic ring, represented by $A^1$, is a divalent group formed by removing two hydrogen atoms from an aromatic hydrocarbon, an aromatic heterocycle, or a condensed polycyclic aromatic ring. Examples of the aromatic hydrocarbon, the aromatic heterocycle, or the condensed polycyclic aromatic ring include benzene, biphenyl, terphenyl, tetrakisphenyl, styrene, naphthalene, anthracene, acenaphthalene, fluorene, phenanthrene, indane, pyrene, triphenylene, pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

The divalent group of an aromatic hydrocarbon, the divalent group of an aromatic heterocycle, or the divalent group of a condensed polycyclic aromatic ring, represented by $A^1$, may be unsubstituted or may have a substituent. Examples of the substituent are the same as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

As $A^1$, the divalent group of an aromatic hydrocarbon, the divalent group of a condensed polycyclic aromatic ring, or a single bond is preferred; a divalent group formed by removing two hydrogen atoms from benzene, biphenyl or naphthalene, or a single bond, is more preferred; and a divalent group formed by removing two hydrogen atoms from benzene, or a single bond, is particularly preferred.

($Ar^5$)

In the general formula (2), $Ar^5$ represents an aromatic hydrocarbon group, an aromatic heterocyclic group, or a condensed polycyclic aromatic group. The aromatic hydrocarbon group, the aromatic heterocyclic group, or the condensed polycyclic aromatic group, represented by $Ar^5$, can be the same as those exemplified in connection with the aromatic hydrocarbon group, the aromatic heterocyclic group, or the condensed polycyclic aromatic group represented by $Ar^1$ to $Ar^4$ in the aforementioned general formula (1).

The aromatic hydrocarbon group, the aromatic heterocyclic group, or the condensed polycyclic aromatic group, represented by $Ar^5$, may be unsubstituted, but may have a substituent. Examples of the substituent are the same as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

As $Ar^5$, a phenyl group, a biphenylyl group, a naphthyl group, or an aromatic heterocyclic group is preferred, and an aromatic heterocyclic group is particularly preferred. Of the aromatic heterocyclic groups, a triazinyl group, a quinazolinyl group, a naphthopyrimidinyl group, a benzimidazolyl group, a pyridopyrimidinyl group, a naphthyridinyl group, a pyridyl group, a quinolyl group, and an isoquinolyl group are particularly preferred.

($R^1$ to $R^8$)

In the general formula (2), $R^1$ to $R^8$ each represent a hydrogen atom; a deuterium atom; a fluorine atom; a chlorine atom; a cyano group; a nitro group; an alkyl group having 1 to 6 carbon atoms; a cycloalkyl group having 5 to 10 carbon atoms; an alkenyl group having 2 to 6 carbon atoms; an alkyloxy group having 1 to 6 carbon atoms; a cycloalkyloxy group having 5 to 10 carbon atoms; an aromatic hydrocarbon group; an aromatic heterocyclic group; a condensed polycyclic aromatic group; an aryloxyl group; or a di-substituted amino group having an aromatic hydrocarbon group, an aromatic heterocyclic group, or a condensed polycyclic aromatic group as a substituent. The alkyl group having 1 to 6 carbon atoms, the alkenyl group having 2 to 6 carbon atoms, or the alkyloxy group having 1 to 6 carbon atoms may be straight-chain or branched.

The alkyl group having 1 to 6 carbon atoms, the cycloalkyl group having 5 to 10 carbon atoms, or the alkenyl group having 2 to 6 carbon atoms, represented by $R^1$ to $R^8$, can be exemplified by a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, a 2-butenyl group and the like.

The alkyl group having 1 to 6 carbon atoms, the cycloalkyl group having 5 to 10 carbon atoms, or the alkenyl group having 2 to 6 carbon atoms, represented by $R^1$ to $R^8$, may be unsubstituted, but may have a substituent. The substituent can be exemplified by the following groups, in addition to a deuterium atom, a cyano group, and a nitro group:

a halogen atom, for example, a fluorine atom, a chlorine atom, a bromine atom, an iodine atom or the like;

an alkyloxy group having 1 to 6 carbon atoms, for example, a methyloxy group, an ethyloxy group, a propyloxy group or the like;

an alkenyl group, for example, a vinyl group, an allyl group or the like;

an aryloxy group, for example, a phenyloxy group, a tolyloxy group or the like;

an arylalkyloxy group, for example, a benzyloxy group, a phenethyloxy group or the like;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group or the like;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a carbolinyl group or the like;

a di-substituted amino group substituted by an aromatic hydrocarbon group, for example, a diphenylamino group;

a di-substituted amino group substituted by a condensed polycyclic aromatic group, for example, a dinaphthylamino group or the like;

a di-substituted amino group substituted by an aromatic heterocyclic group, for example, a dipyridylamino group, a dithienylamino group or the like; and a di-substituted amino group substituted by a substituent selected from an aromatic hydrocarbon group, a condensed polycyclic aromatic group, and an aromatic heterocyclic group. The alkenyl group and the alkyloxy group having 1 to 6 carbon atoms may be straight-chain or branched. Any of the above exemplary substituents may be further substituted by the above exemplary substituent. The above exemplary substituents may be present independently of each other to avoid formation of a ring. However, they may be bonded to each other via a single bond, a substituted or unsubstituted methylene group, an oxygen atom, or a sulfur atom to form a ring.

The alkyloxy group having 1 to 6 carbon atoms or the cycloalkyloxy group having 5 to 10 carbon atoms, represented by $R^1$ to $R^8$, can be exemplified by a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, a 2-adamantyloxy group and the like.

The alkyloxy group having 1 to 6 carbon atoms or the cycloalkyloxy group having 5 to 10 carbon atoms, represented by $R^1$ to $R^8$, may be unsubstituted, but may have a substituent. Examples of the substituent are the same as those shown as the substituents that the alkyl group having 1 to 6 carbon atoms, the cycloalkyl group having 5 to 10 carbon atoms, or the alkenyl group having 2 to 6 carbon atoms, represented by $R^1$ to $R^8$ in the general formula (2) may have. The same holds true of the embodiments that the substituents can adopt.

The aromatic hydrocarbon group, the aromatic heterocyclic group, or the condensed polycyclic aromatic group, represented by $R^1$ to $R^8$, can be the same as those exemplified in connection with the aromatic hydrocarbon group, the aromatic heterocyclic group, or the condensed polycyclic aromatic group represented by $Ar^1$ to $Ar^4$ in the aforementioned general formula (1). These groups may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

The aryloxy group represented by $R^1$ to $R^8$ can be exemplified by a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, a perylenyloxy group and the like.

The aryloxy group represented by $R^1$ to $R^8$ may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

The aromatic hydrocarbon group, aromatic heterocyclic group, or condensed polycyclic aromatic group in the "di-substituted amino group having an aromatic hydrocarbon group, an aromatic heterocyclic group, or a condensed polycyclic aromatic group as a substituent," represented by $R^1$ to $R^8$, can be the same ones as those exemplified in connection with the aromatic hydrocarbon group, the aromatic heterocyclic group, or the condensed polycyclic aromatic group represented by $Ar^1$ to $Ar^4$ in the general formula (1). The di-substituted amino group, represented by $R^1$ to $R^8$, may be unsubstituted, but may further have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

It is not necessary for $R^1$ to $R^4$ to be present independently of each other to avoid formation of a ring. However, like Compound 2-14 or Compound 2-15 in FIG. 22, they may be bonded to each other via a single bond, a substituted or unsubstituted methylene group, an oxygen atom, or a sulfur atom to form a ring. Similarly, it is not necessary for $R^5$ to $R^8$ to be present independently of each other to avoid formation of a ring. However, they may be bonded to each other via a single bond, a substituted or unsubstituted methylene group, an oxygen atom, or a sulfur atom to form a ring. Moreover, like Compound 2-1 to Compound 2-5 in FIG. 20, part of $R^1$ to $R^4$ may be detached, and remaining group of $R^1$ to $R^4$ may be bonded to a vacancy, which has been produced by the detachment, via a substituted or unsubstituted methylene group, an oxygen atom, a sulfur atom, or a monoarylamino group to form a ring. Likewise, part of $R^5$ to $R^8$ may be detached, and remaining group of $R^5$ to $R^8$ may be bonded to a vacancy, produced by the detachment, via a substituted or unsubstituted methylene group, an oxygen atom, a sulfur atom, or a monoarylamino group to form a ring.

An embodiment in which $R^1$ to $R^8$ together form a ring, and the group contributing to ring formation is a di-substituted amino group, as mentioned above, includes an embodiment in which $R^1$ to $R^8$ bind to each other via a single bond, a substituted or unsubstituted methylene group, an oxygen atom, or a sulfur atom, while being mediated by the aromatic hydrocarbon group, aromatic heterocyclic group, or condensed polycyclic aromatic group possessed by the di-substituted amino group, to form a ring. The above embodiment also includes an embodiment in which part of $R^1$ to $R^4$ is detached, and remaining group of $R^1$ to $R^4$ (i.e., di-substituted amino group) binds to a vacancy, which has been produced by the detachment, via a substituted or unsubstituted methylene group, an oxygen atom, a sulfur atom, or a monoarylamino group, while being mediated by the aromatic hydrocarbon group, aromatic heterocyclic group, or condensed polycyclic aromatic group possessed by the di-substituted amino group, to form a ring. The above-mentioned embodiment further includes an embodiment in which part of $R^5$ to $R^8$ is detached, and remaining group of $R^5$ to $R^8$ (i.e., di-substituted amino group) binds to a vacancy, which has been produced by the detachment, via a substituted or unsubstituted methylene group, an oxygen atom, a sulfur atom, or a monoarylamino group, while being mediated by the aromatic hydrocarbon group, aromatic heterocyclic group, or condensed polycyclic aromatic group possessed by the di-substituted amino group, to form a ring.

The aryl group in the monoarylamino group playing the role of a linking group for ring formation can be the same ones as those exemplified in connection with the aromatic hydrocarbon group, the aromatic heterocyclic group, or the condensed polycyclic aromatic group represented by $Ar^1$ to $Ar^4$ in the general formula (1). These groups may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

Preferred as the embodiment of the indenoindole derivative of the general formula (2) is an embodiment in which one of $R^1$ to $R^4$ is an aromatic hydrocarbon group, an aromatic heterocyclic group, or a condensed polycyclic aromatic group, and the group binds to the benzene ring to which $R^1$ to $R^4$ are bound via a linking group, such as a substituted or unsubstituted methylene group, an oxygen atom, a sulfur atom, or a monoarylamino group to form a ring. The aromatic hydrocarbon group, the aromatic heterocyclic group, or the condensed polycyclic aromatic group preferred in this case is a phenyl group, an indenyl group, an indolyl group, a benzofuranyl group, or a benzothienyl group. In a preferred embodiment, the group, together with the benzene ring to which $R^1$ to $R^4$ are bound, form a fluorene ring, a carbazole ring, a dibenzofuran ring, a dibenzothiophene ring, an indenoindole ring, an indenobenzofuran ring, an indenobenzothiophene ring, a benzofuroindole ring, a benzothienoindole ring, or an indoloindole ring. Of these embodiments, the embodiments represented by the general formulas (2a) to (2c) indicated below, in particular, are preferred.

Also preferred is an embodiment in which the adjacent two of $R^1$ to $R^4$ are each an alkenyl group having 2 to 6 carbon atoms, an aromatic hydrocarbon group, an aromatic heterocyclic group, or a condensed polycyclic aromatic group, and the adjacent two groups ($R^1$ to $R^4$) bind to each other via a single bond, and these groups, together with the benzene ring to which $R^1$ to $R^4$ are bound, form a condensed ring. The alkenyl group having 2 to 6 carbon atoms, aromatic hydrocarbon group, aromatic heterocyclic group, or condensed polycyclic aromatic group preferred in this case is a vinyl group or a phenyl group. That is, in a preferred embodiment, these groups, together with the benzene ring to which $R^1$ to $R^4$ are bound, form a naphthalene ring, a phenanthrene ring, or a triphenylene ring. Of these embodiments, the embodiment represented by the following general formula (2d) or (2e), in particular, is preferred.

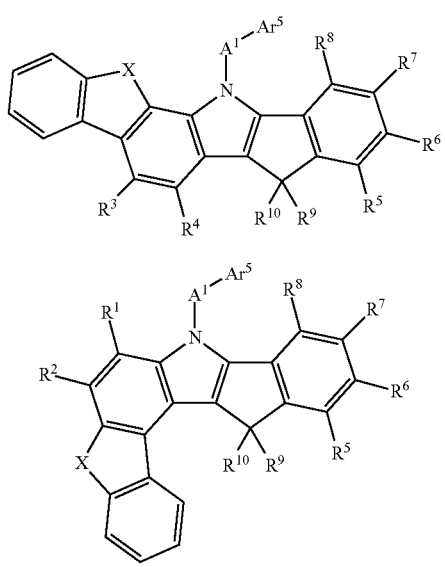

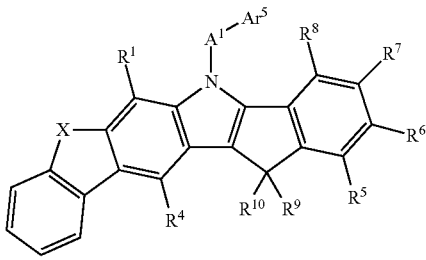

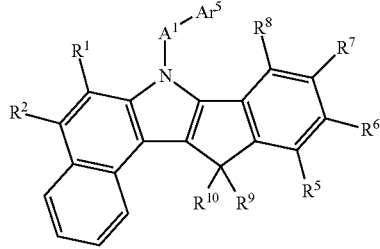

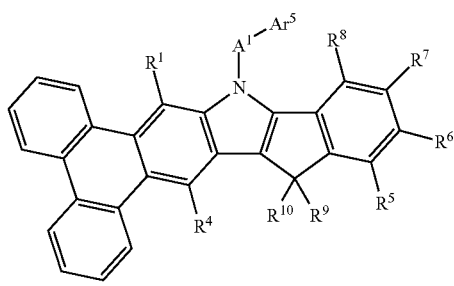

where X represents a substituted or unsubstituted methylene group, an oxygen atom, a sulfur atom, or a monoarylamino group, and $A^1$, $Ar^5$ and $R^1$ to $R^{10}$ have the meanings as indicated in the general formula (2).

Similarly preferred is an embodiment in which the adjacent two of, or all of, $R^5$ to $R^8$ are each a vinyl group, and the adjacent two vinyl groups bind to each other via a single bond to form a condensed ring, that is, an embodiment in which they form a naphthalene ring or a phenanthrene ring, together with the benzene ring to which $R^5$ to $R^8$ are bound. ($R^9$, $R^{10}$)

In the general formula (2), $R^9$ and $R^{10}$ each represent an alkyl group having 1 to 6 carbon atoms, an aromatic hydrocarbon group, an aromatic heterocyclic group, or a condensed polycyclic aromatic group. The alkyl group having 1 to 6 carbon atoms may be straight-chain or branched.

The alkyl group having 1 to 6 carbon atoms, represented by $R^9$ and $R^{10}$, can be exemplified by the same ones as those shown in connection with the alkyl group having 1 to 6 carbon atoms represented by $R^1$ to $R^8$ in the general formula (2). The alkyl group having 1 to 6 carbon atoms, represented by $R^9$ and $R^{10}$, may be unsubstituted, but may have a substituent. The substituent can be exemplified by the same ones as those shown as the substituents optionally possessed by the alkyl group having 1 to 6 carbon atoms, the cycloalkyl group having 5 to 10 carbon atoms, or the alkenyl group having 2 to 6 carbon atoms, represented by $R^1$ to $R^8$ in the general formula (2). The same holds true of the embodiments that the substituents can adopt.

The aromatic hydrocarbon group, aromatic heterocyclic group, or condensed polycyclic aromatic group, represented by $R^9$ and $R^{10}$, can be exemplified by the same ones as those shown in connection with the aromatic hydrocarbon group, the aromatic heterocyclic group, or the condensed polycyclic aromatic group represented by $Ar^1$ to $Ar^4$ in the general formula (1). These substituents may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

As $R^9$, $R^{10}$, an alkyl group having 1 to 6 carbon atoms is preferred, and a methyl group is particularly preferred.

It is not necessary for $R^9$, $R^{10}$ to be present independently of each other to avoid formation of a ring. However, they may be bonded to each other via a single bond, a substituted or unsubstituted methylene group, an oxygen atom, or a sulfur atom to form a ring.

Carbazole derivative of the general formula (3)

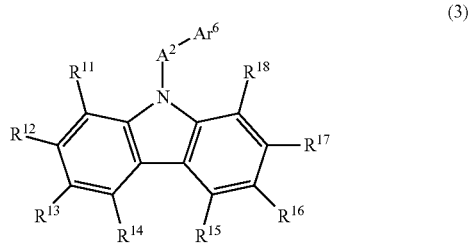

(3)

($A^2$)

In the general formula (3), $A^2$ represents a divalent group of an aromatic hydrocarbon, a divalent group of an aromatic heterocycle, a divalent group of a condensed polycyclic aromatic ring, or a single bond. The divalent group of an aromatic hydrocarbon, the divalent group of an aromatic heterocycle, or the divalent group of a condensed polycyclic aromatic ring, represented by $A^2$, can be exemplified by the same ones as those shown in connection with the divalent group of an aromatic hydrocarbon, the divalent group of an aromatic heterocycle, or the divalent group of a condensed polycyclic aromatic ring, represented by $A^1$ in the general formula (2). These divalent groups may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

As $A^2$, the divalent group of an aromatic hydrocarbon, the divalent group of a condensed polycyclic aromatic ring, or a single bond is preferred; a divalent group formed by removing two hydrogen atoms from benzene, biphenyl or naphthalene, or a single bond, is more preferred; and a divalent group formed by removing two hydrogen atoms from benzene, or a single bond, is particularly preferred.

($Ar^6$)

In the general formula (3), $Ar^6$ represents an aromatic hydrocarbon group, an aromatic heterocyclic group, or a condensed polycyclic aromatic group. The aromatic hydrocarbon group, the aromatic heterocyclic group, or the condensed polycyclic aromatic group, represented by $Ar^6$, can be exemplified by the same ones as those shown in connection with the aromatic hydrocarbon group, the aromatic heterocyclic group, or the condensed polycyclic aromatic group represented by $Ar^1$ to $Ar^4$ in the aforementioned general formula (1). These groups may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

As $Ar^6$, a phenyl group, a biphenylyl group, a naphthyl group, or an aromatic heterocyclic group is preferred, and an aromatic heterocyclic group is particularly preferred. Of the aromatic heterocyclic groups, a triazinyl group, a quinazolinyl group, a naphthopyrimidinyl group, a benzimidazolyl group, a pyridopyrimidinyl group, a naphthyridinyl group, a pyridyl group, a quinolyl group, and an isoquinolyl group are particularly preferred.

($R^{11}$ to $R^{18}$)

In the general formula (3), $R^{11}$ to $R^{18}$ each represent a hydrogen atom; a deuterium atom; a fluorine atom; a chlorine atom; a cyano group; a nitro group; an alkyl group having 1 to 6 carbon atoms; a cycloalkyl group having 5 to 10 carbon atoms; an alkenyl group having 2 to 6 carbon atoms; an alkyloxy group having 1 to 6 carbon atoms; a cycloalkyloxy group having 5 to 10 carbon atoms; an aromatic hydrocarbon group; an aromatic heterocyclic group; a condensed polycyclic aromatic group; an aryloxyl group; or a di-substituted amino group having an aromatic hydrocarbon group, an aromatic heterocyclic group, or a condensed polycyclic aromatic group as a substituent. The alkyl group having 1 to 6 carbon atoms, the alkenyl group having 2 to 6 carbon atoms, or the alkyloxy group having 1 to 6 carbon atoms may be straight-chain or branched.

The alkyl group having 1 to 6 carbon atoms, the cycloalkyl group having 5 to 10 carbon atoms, or the alkenyl group having 2 to 6 carbon atoms, represented by $R^{11}$ to $R^{18}$, can be exemplified by the same ones as those shown in connection with the alkyl group having 1 to 6 carbon atoms, the cycloalkyl group having 5 to 10 carbon atoms, or the alkenyl group having 2 to 6 carbon atoms represented by $R^1$ to $R^8$ in the general formula (2). These groups may be unsubstituted, but may have a substituent. The substituent can be exemplified by the same ones as those shown as the substituents that the alkyl group having 1 to 6 carbon atoms, the cycloalkyl group having 5 to 10 carbon atoms, or the alkenyl group having 2 to 6 carbon atoms represented by $R^1$ to $R^8$ in the general formula (2) may have. The same holds true of the embodiments that the substituents can adopt.

The alkyloxy group having 1 to 6 carbon atoms, or the cycloalkyloxy group having 5 to 10 carbon atoms, represented by $R^{11}$ to $R^{18}$, can be exemplified by the same ones as those shown in connection with the alkyloxy group having 1 to 6 carbon atoms or the cycloalkyloxy group having 5 to 10 carbon atoms, represented by $R^1$ to $R^8$ in the general formula (2). These groups may be unsubstituted, but may have a substituent. The substituent can be exemplified by the same ones as those shown as the substituents that the alkyl group having 1 to 6 carbon atoms, the cycloalkyl group having 5 to 10 carbon atoms, or the alkenyl group having 2 to 6 carbon atoms represented by $R^1$ to $R^8$ in the general formula (2) may have. The same holds true of the embodiments that the substituents can adopt.

The aromatic hydrocarbon group, the aromatic heterocyclic group, or the condensed polycyclic aromatic group, represented by $R^{11}$ to $R^{18}$, can be exemplified by the same ones as those shown in connection with the aromatic hydrocarbon group, the aromatic heterocyclic group, or the condensed polycyclic aromatic group represented by $R^1$ to $R^8$ in the aforementioned general formula (2). These groups may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

The aryloxy group represented by $R^{11}$ to $R^{18}$ can be exemplified by the same ones as those shown in connection with the aryloxy group represented by $R^1$ to $R^8$ in the general formula (2). The aryloxy group represented by $R^{11}$ to $R^{18}$ may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

The di-substituted amino group, represented by $R^{11}$ to $R^{18}$, can be exemplified by the same ones as those shown in connection with the di-substituted amino group represented by $R^1$ to $R^8$ in the general formula (2). The di-substituted amino group, represented by $R^{11}$ to $R^{18}$, may be unsubstituted, but may further have a substituent. The substituent optionally possessed further can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

Figure 23:
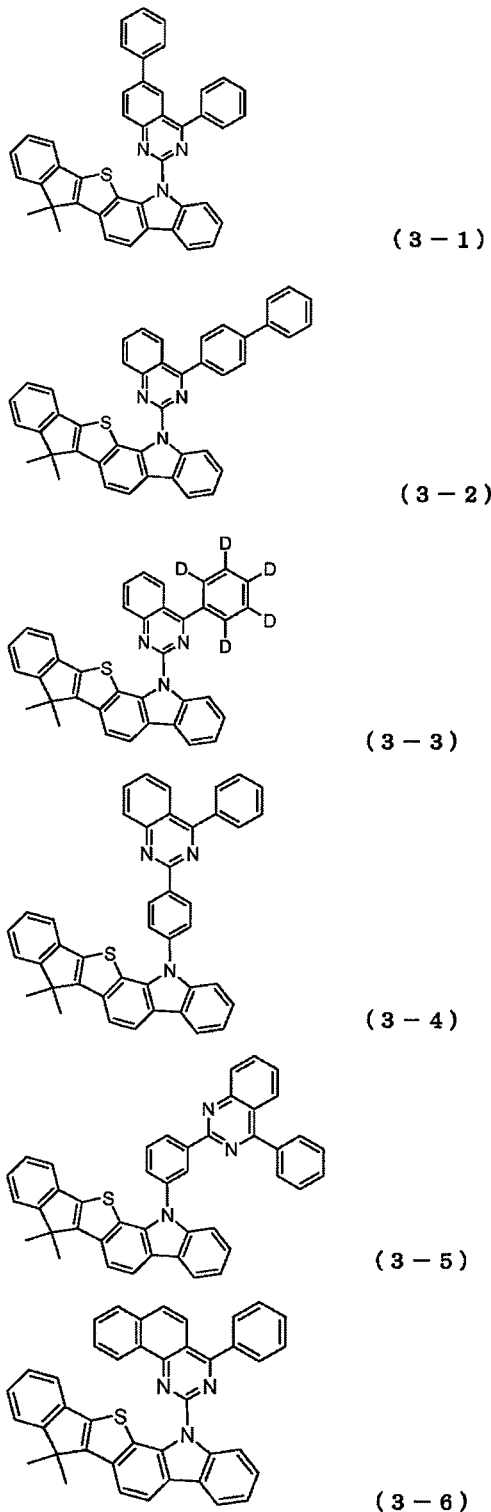
FIG. 23 is a view showing the structural formulas of Compounds (3-1) to (3-6) which are carbazole derivatives of the general formula (3).
Figure 24:
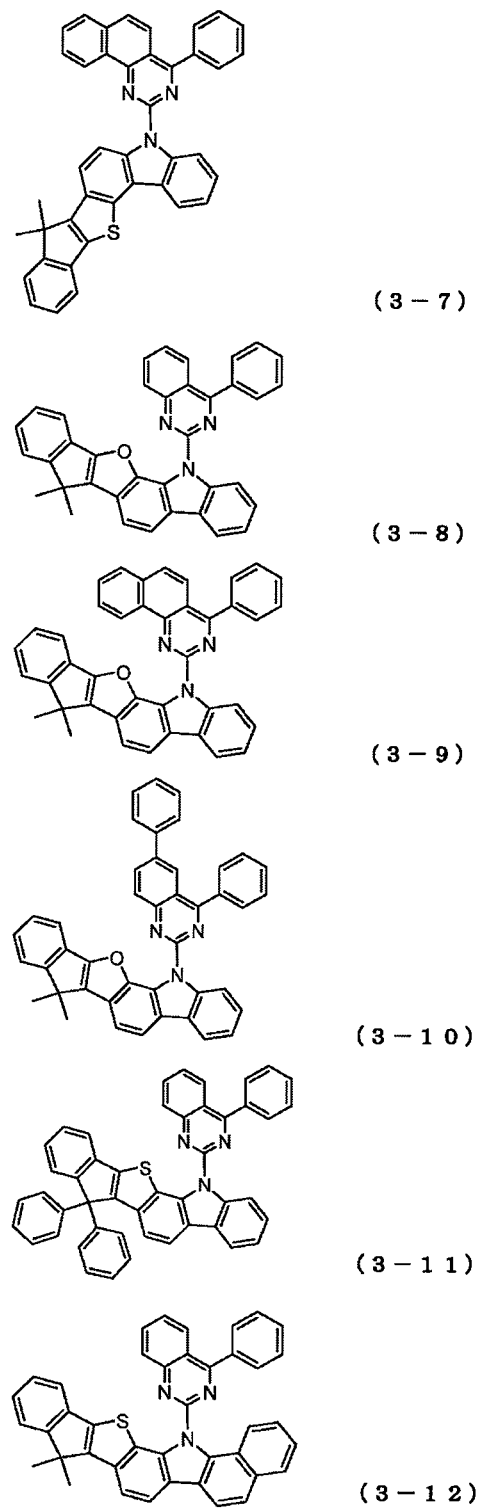
FIG. 24 is a view showing the structural formulas of Compounds (3-7) to (3-12) which are carbazole derivatives of the general formula (3).
Figure 25:
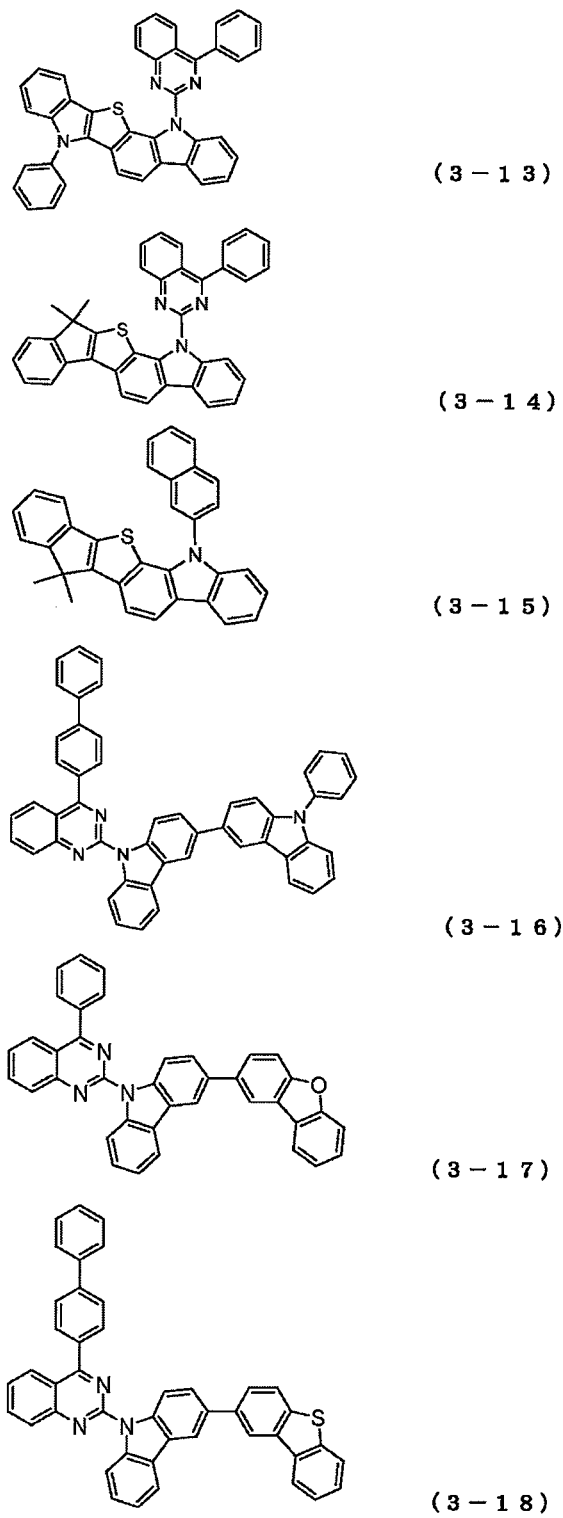
FIG. 25 is a view showing the structural formulas of Compounds (3-13) to (3-18) which are carbazole derivatives of the general formula (3).
Figure 26:
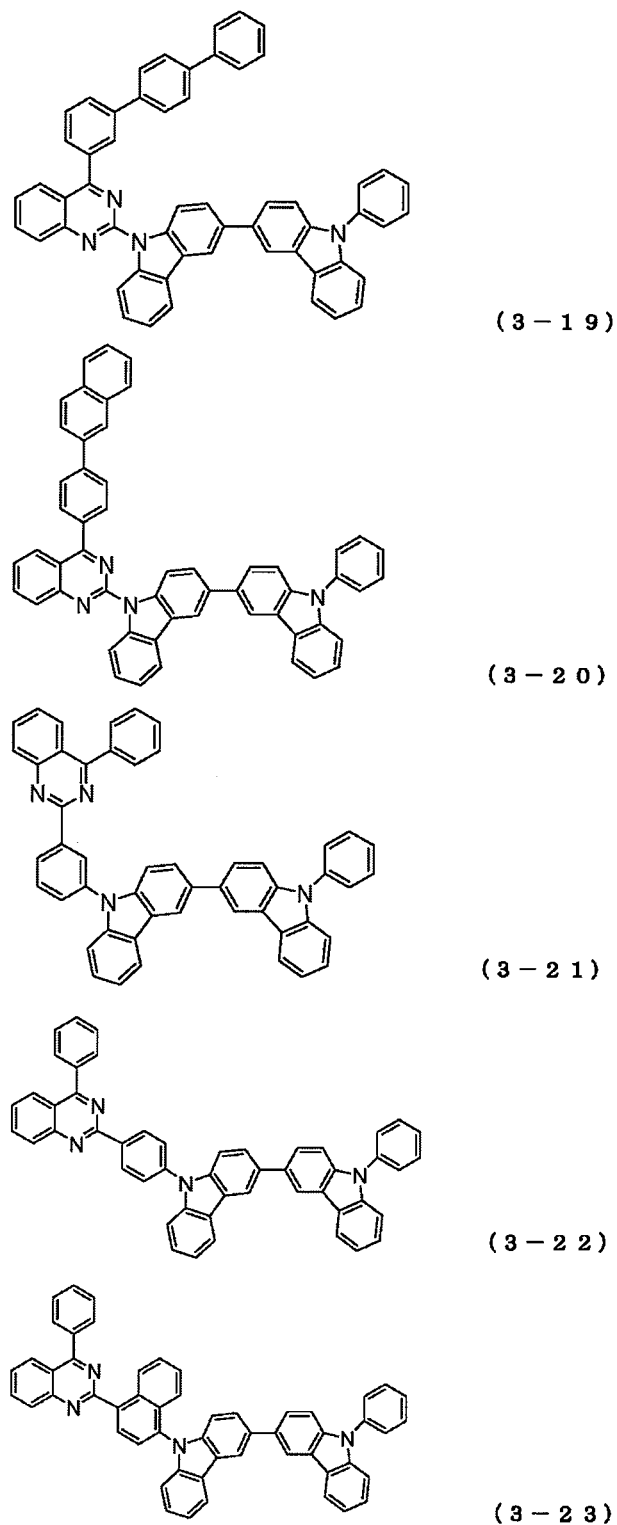
FIG. 26 is a view showing the structural formulas of Compounds (3-19) to (3-23) which are carbazole derivatives of the general formula (3).
Figure 27:
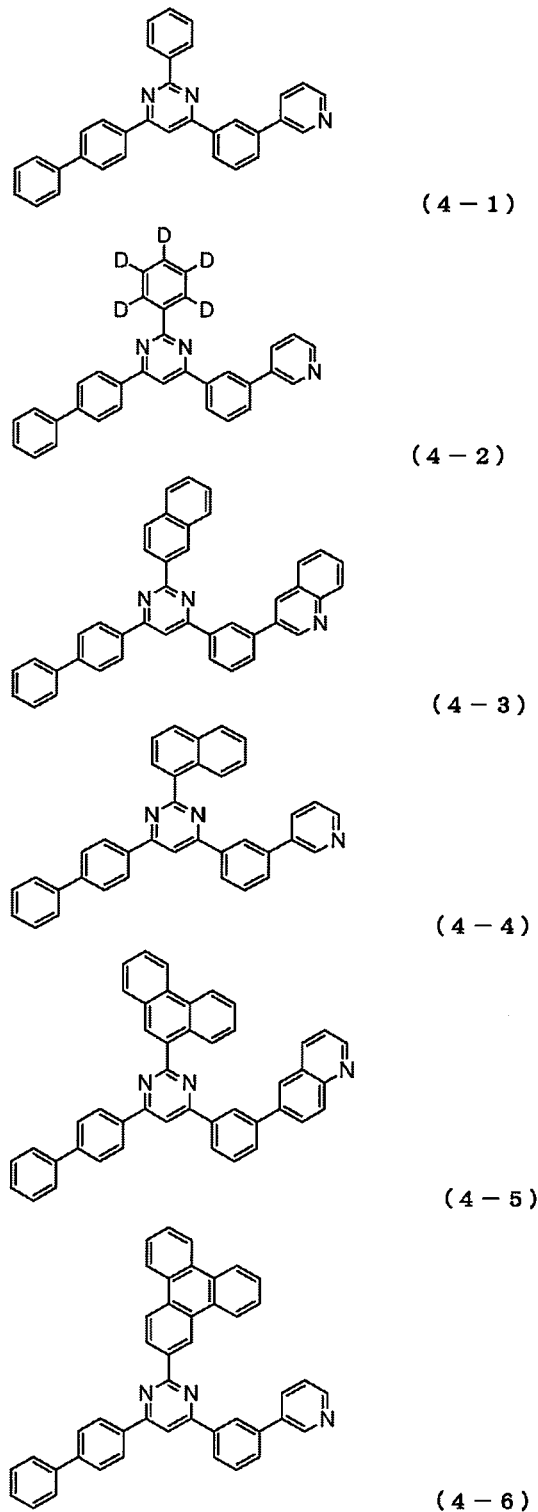
FIG. 27 is a view showing the structural formulas of Compounds (4-1) to (4-6) which are pyrimidine derivatives of the general formula (4).
Figure 28:
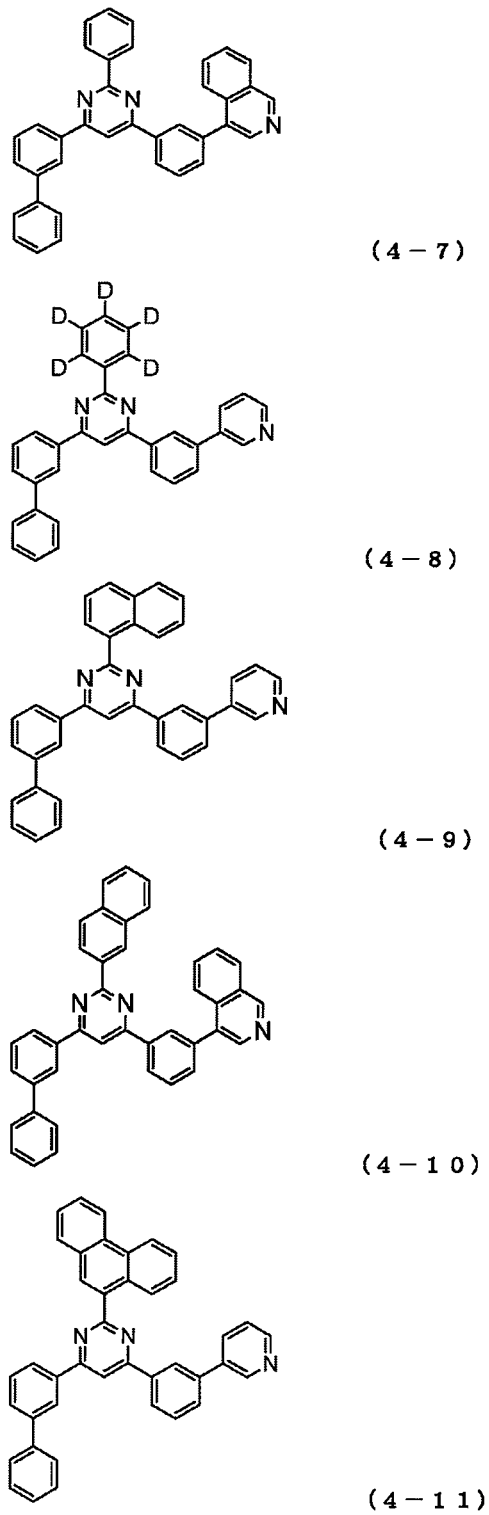
FIG. 28 is a view showing the structural formulas of Compounds (4-7) to (4-11) which are pyrimidine derivatives of the general formula (4).
Figure 29:
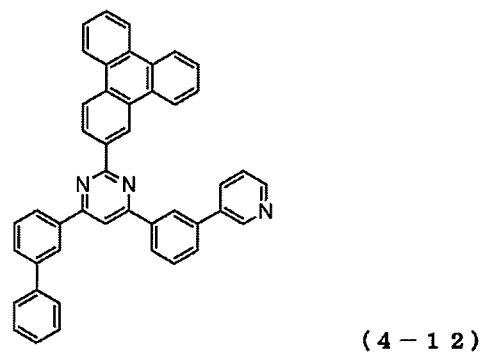
FIG. 29 is a view showing the structural formulas of Compounds (4-12) to (4-16) which are pyrimidine derivatives of the general formula (4).
Figure 29:
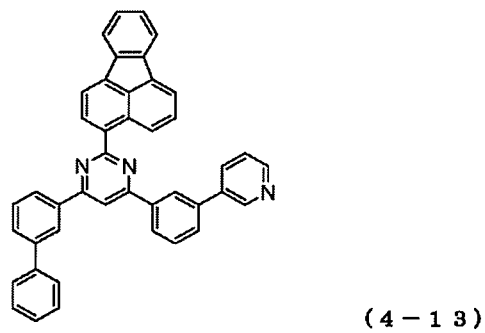
Figure 29:
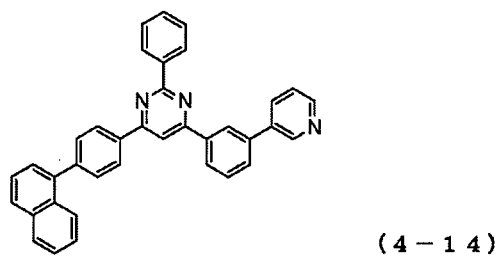
Figure 29:
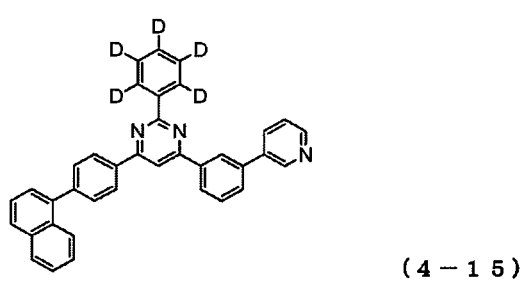
Figure 29:
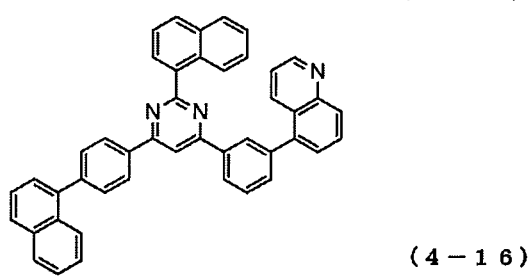
Figure 30:
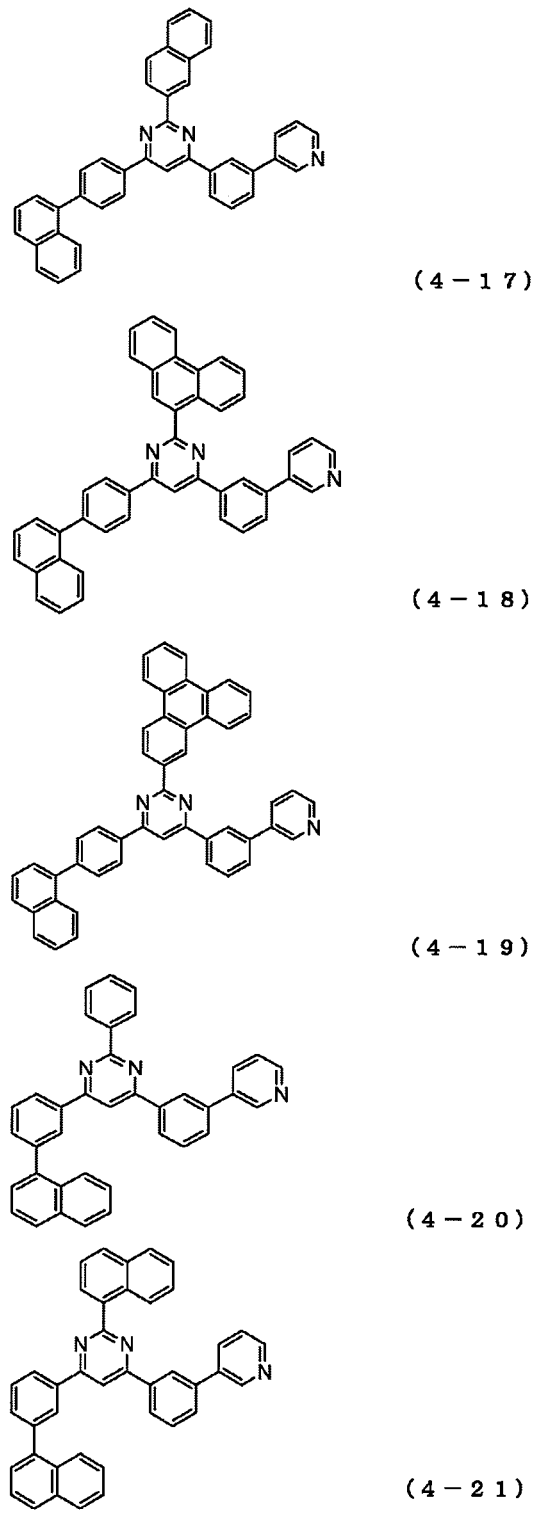
FIG. 30 is a view showing the structural formulas of Compounds (4-17) to (4-21) which are pyrimidine derivatives of the general formula (4).
Figure 31:
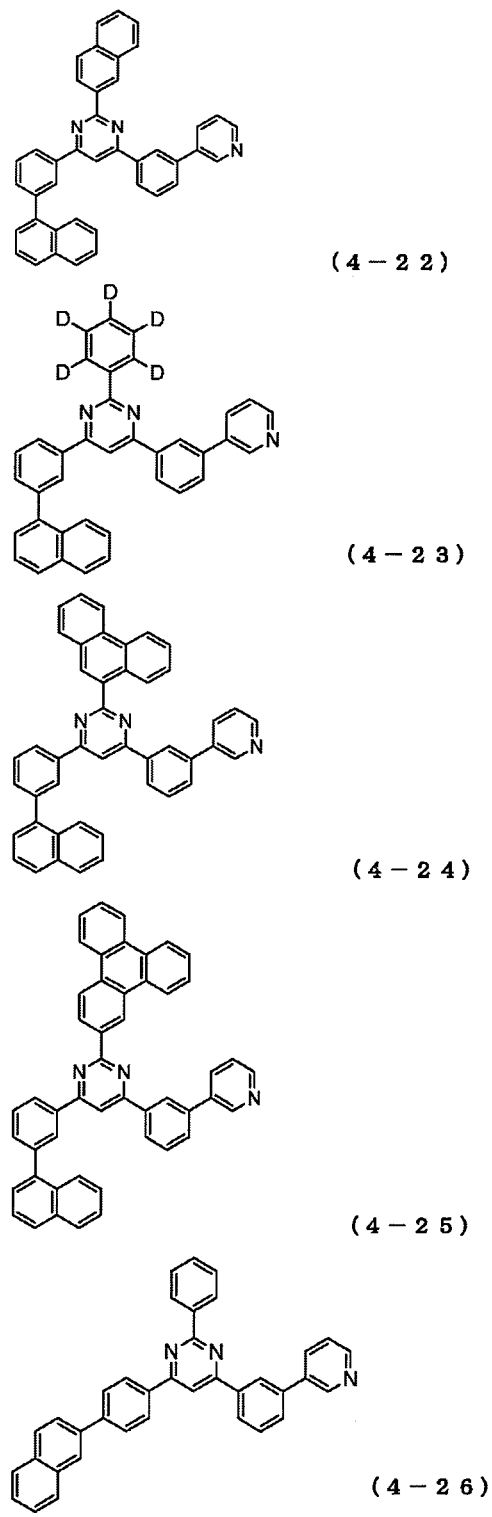
FIG. 31 is a view showing the structural formulas of Compounds (4-22) to (4-26) which are pyrimidine derivatives of the general formula (4).
Figure 32:
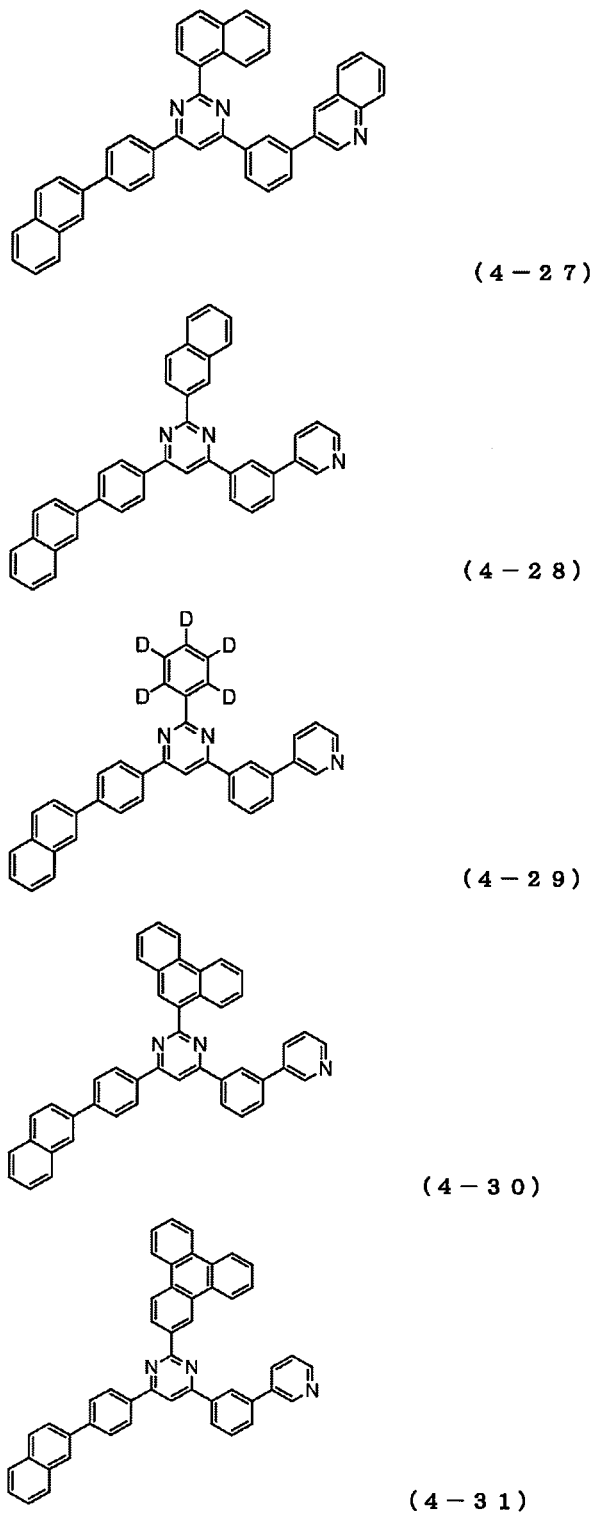
FIG. 32 is a view showing the structural formulas of Compounds (4-27) to (4-31) which are pyrimidine derivatives of the general formula (4).
Figure 33:
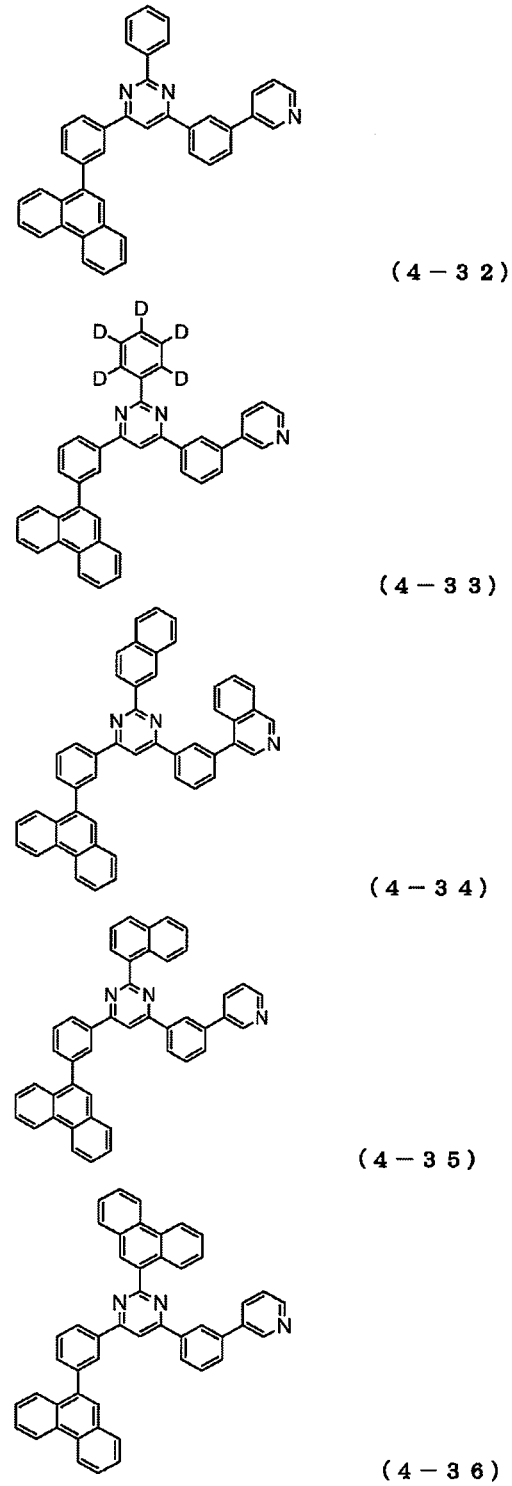
FIG. 33 is a view showing the structural formulas of Compounds (4-32) to (4-36) which are pyrimidine derivatives of the general formula (4).
Figure 34:
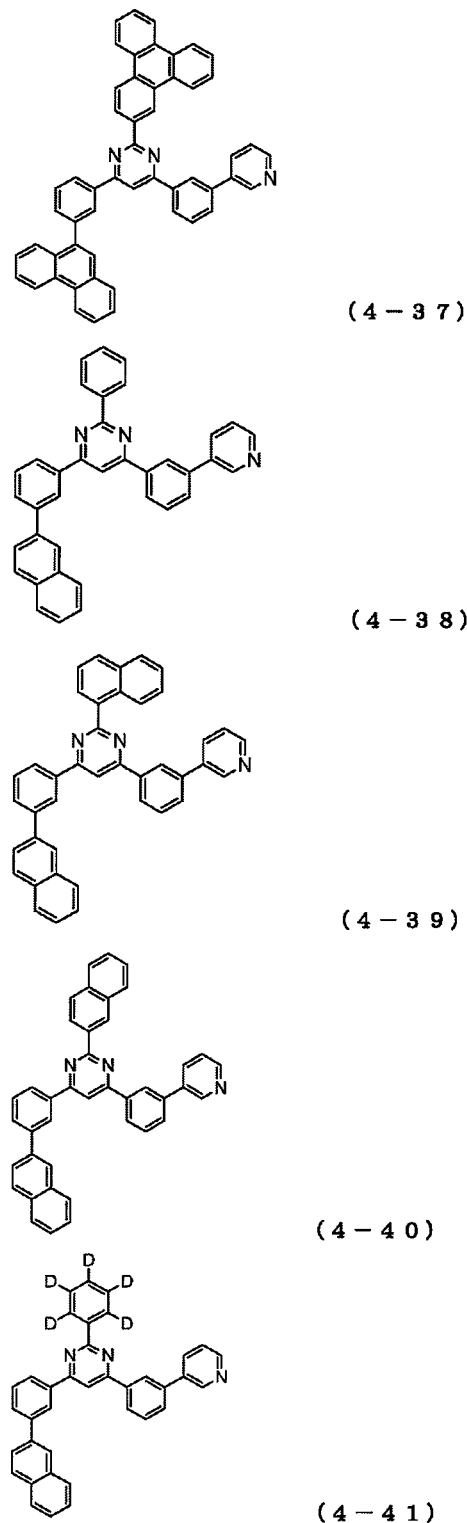
FIG. 34 is a view showing the structural formulas of Compounds (4-37) to (4-41) which are pyrimidine derivatives of the general formula (4).
Figure 35:
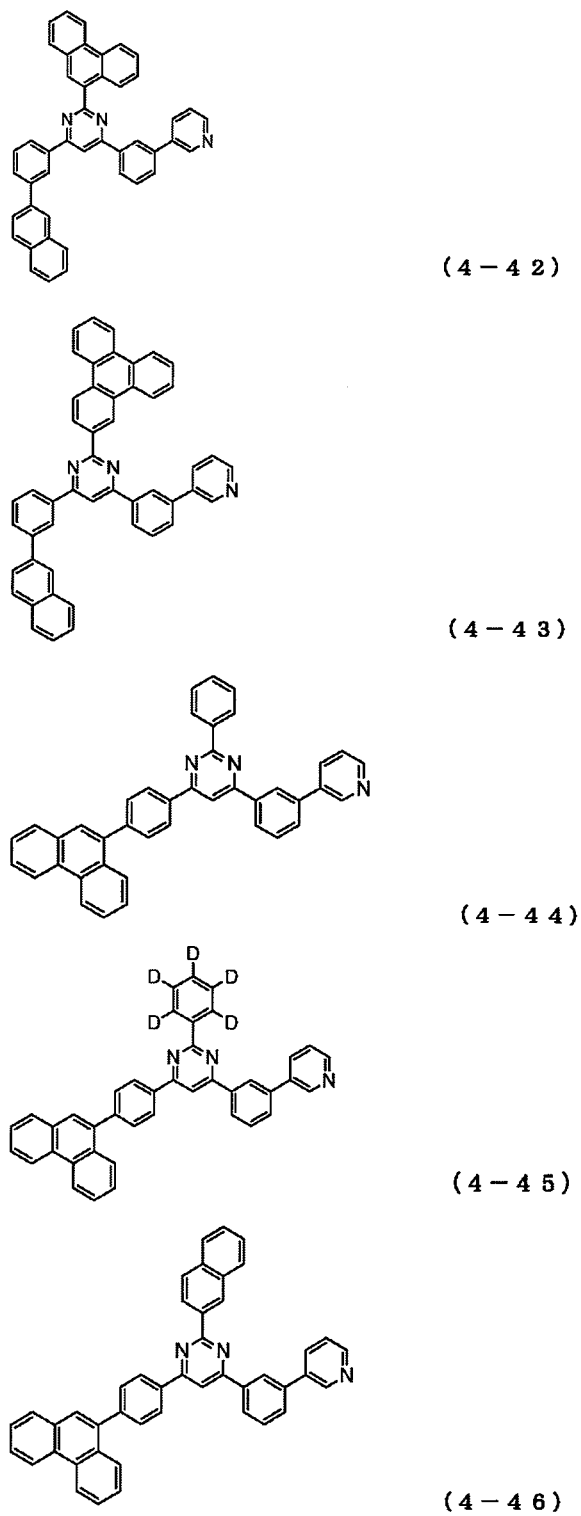
FIG. 35 is a view showing the structural formulas of Compounds (4-42) to (4-46) which are pyrimidine derivatives of the general formula (4).
Figure 36:
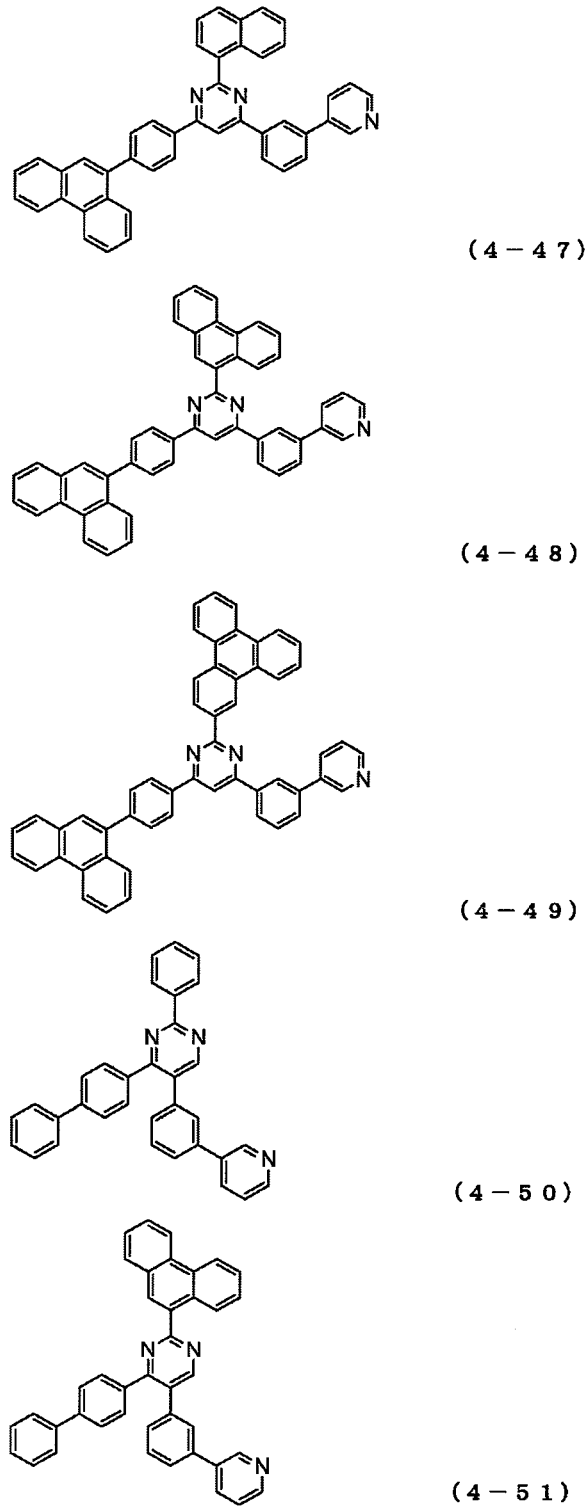
FIG. 36 is a view showing the structural formulas of Compounds (4-47) to (4-51) which are pyrimidine derivatives of the general formula (4).
Figure 37:
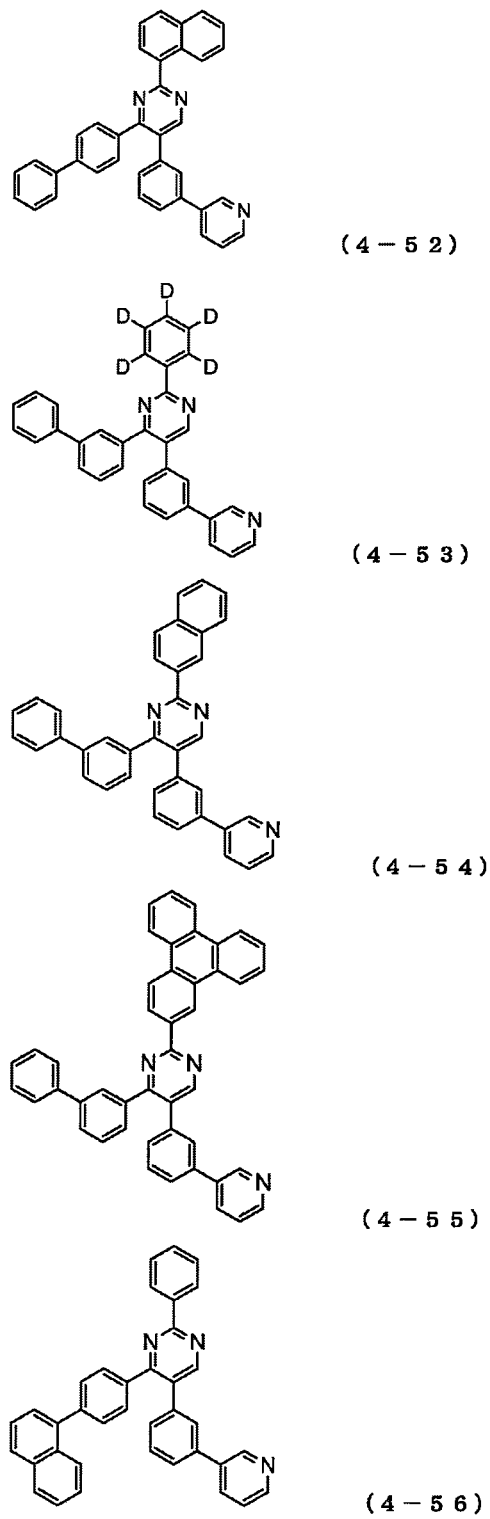
FIG. 37 is a view showing the structural formulas of Compounds (4-52) to (4-56) which are pyrimidine derivatives of the general formula (4).
Figure 38:
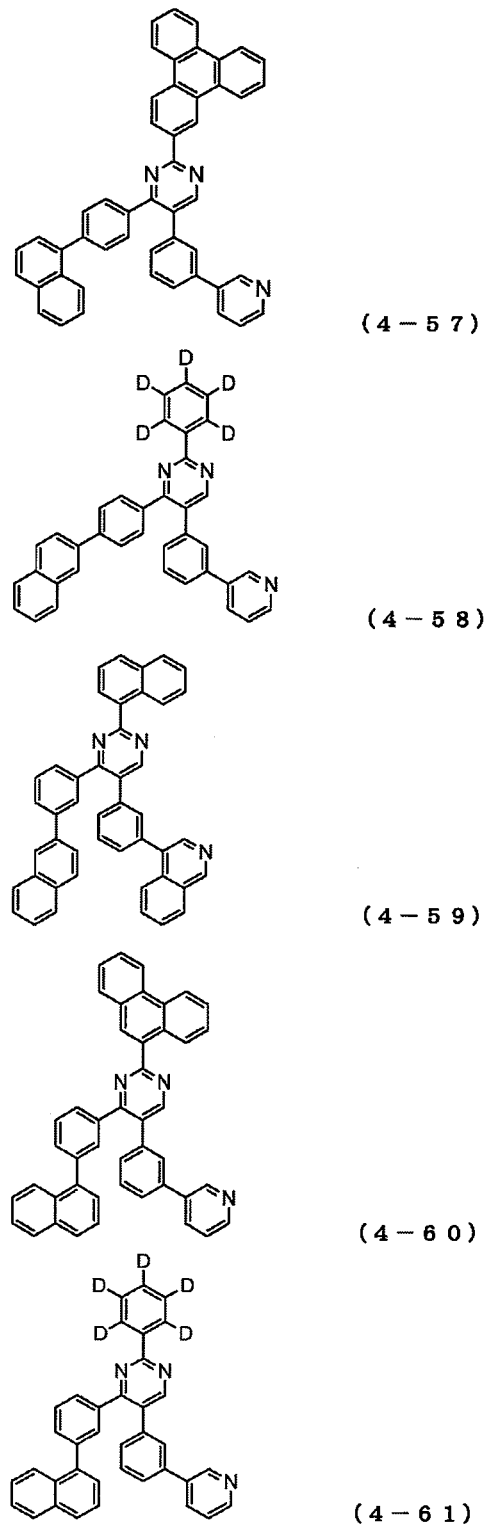
FIG. 38 is a view showing the structural formulas of Compounds (4-57) to (4-61) which are pyrimidine derivatives of the general formula (4).
Figure 39:
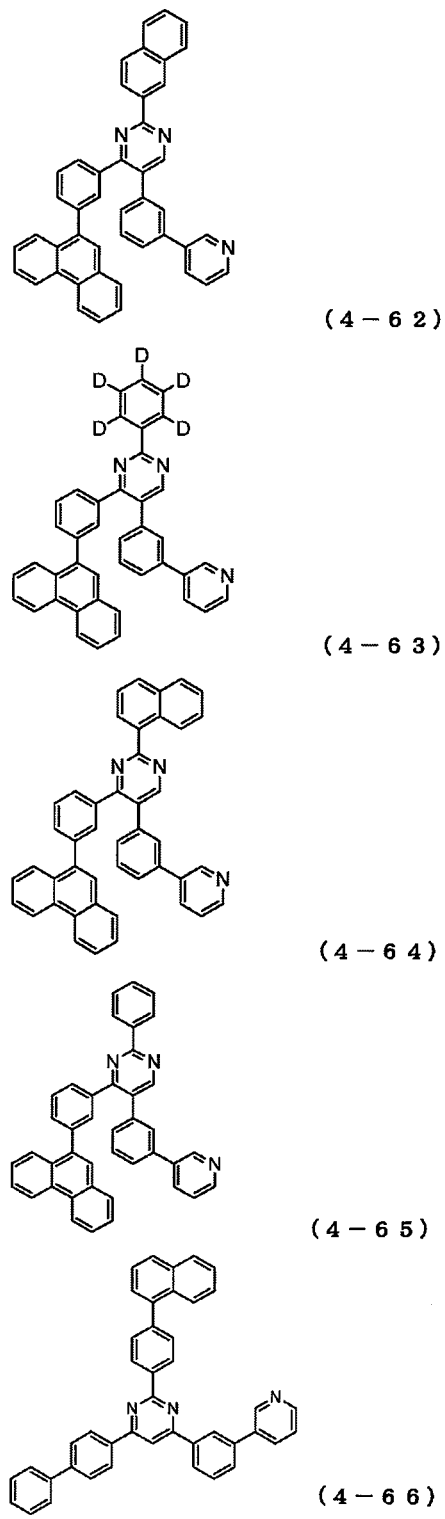
FIG. 39 is a view showing the structural formulas of Compounds (4-62) to (4-66) which are pyrimidine derivatives of the general formula (4).
Figure 40:
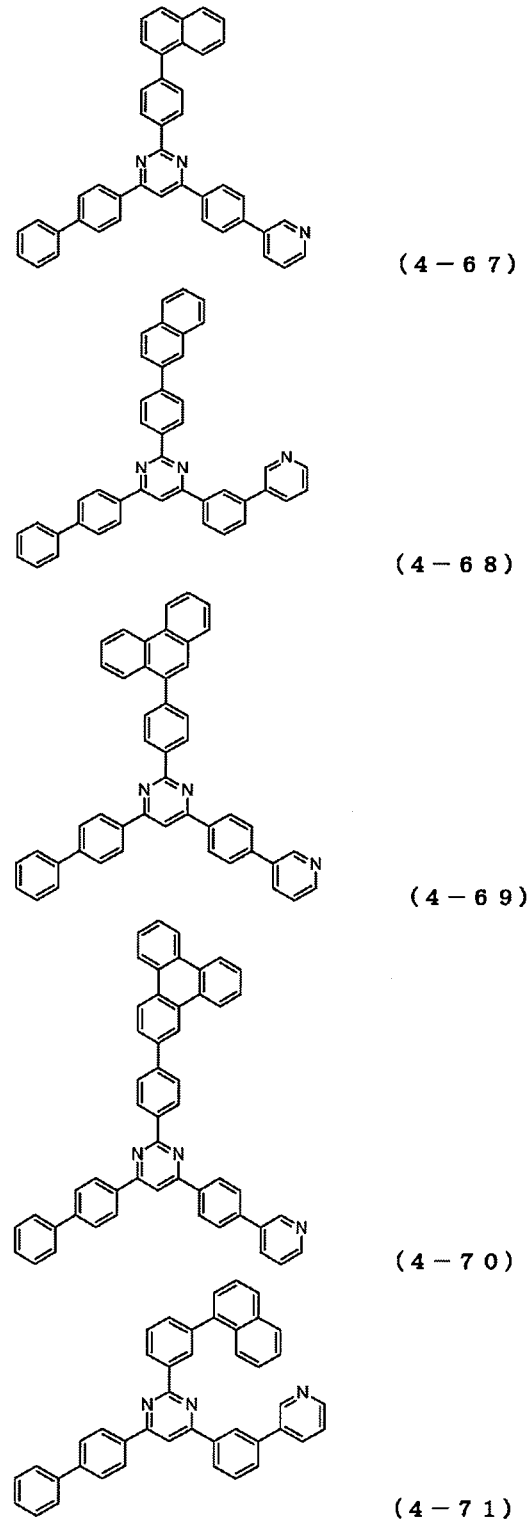
FIG. 40 is a view showing the structural formulas of Compounds (4-67) to (4-71) which are pyrimidine derivatives of the general formula (4).
Figure 41:
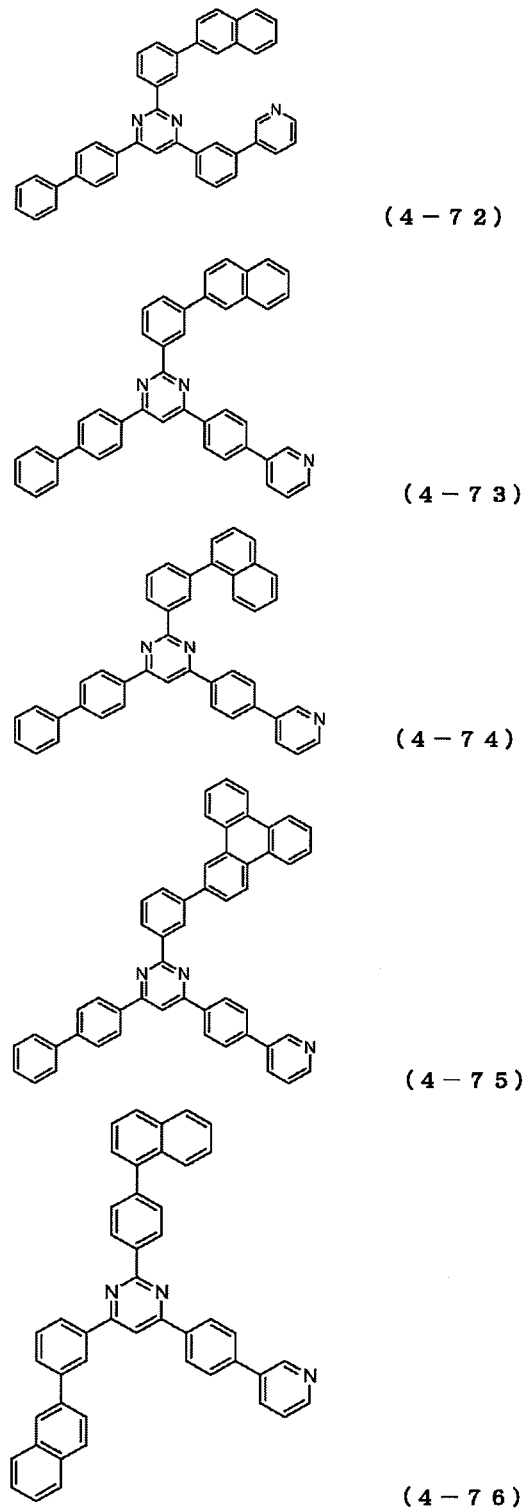
FIG. 41 is a view showing the structural formulas of Compounds (4-72) to (4-76) which are pyrimidine derivatives of the general formula (4).
Figure 42:
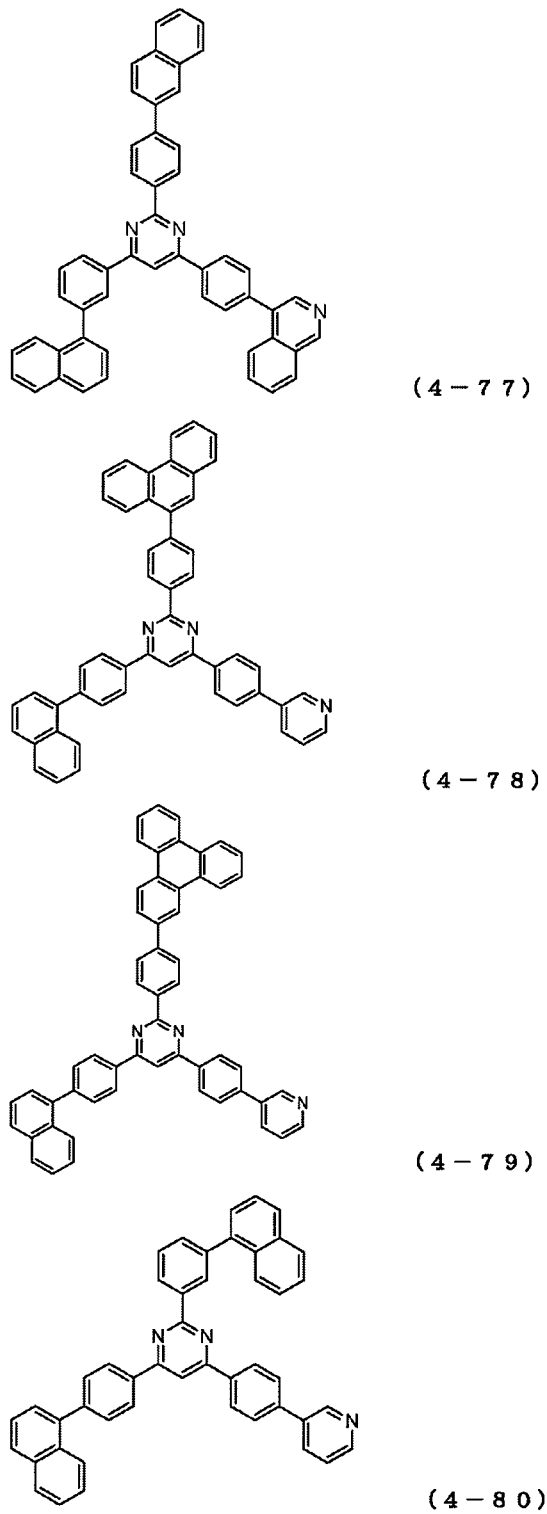
FIG. 42 is a view showing the structural formulas of Compounds (4-77) to (4-80) which are pyrimidine derivatives of the general formula (4).
Figure 43:
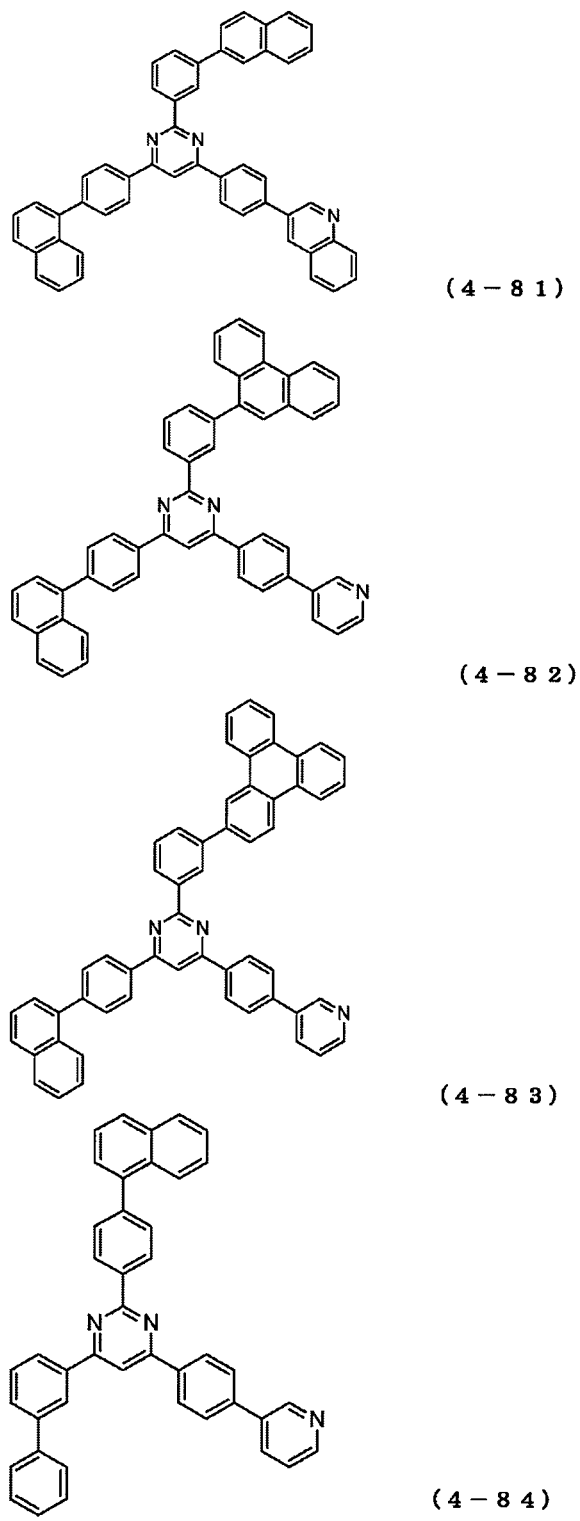
FIG. 43 is a view showing the structural formulas of Compounds (4-81) to (4-84) which are pyrimidine derivatives of the general formula (4).
Figure 44:
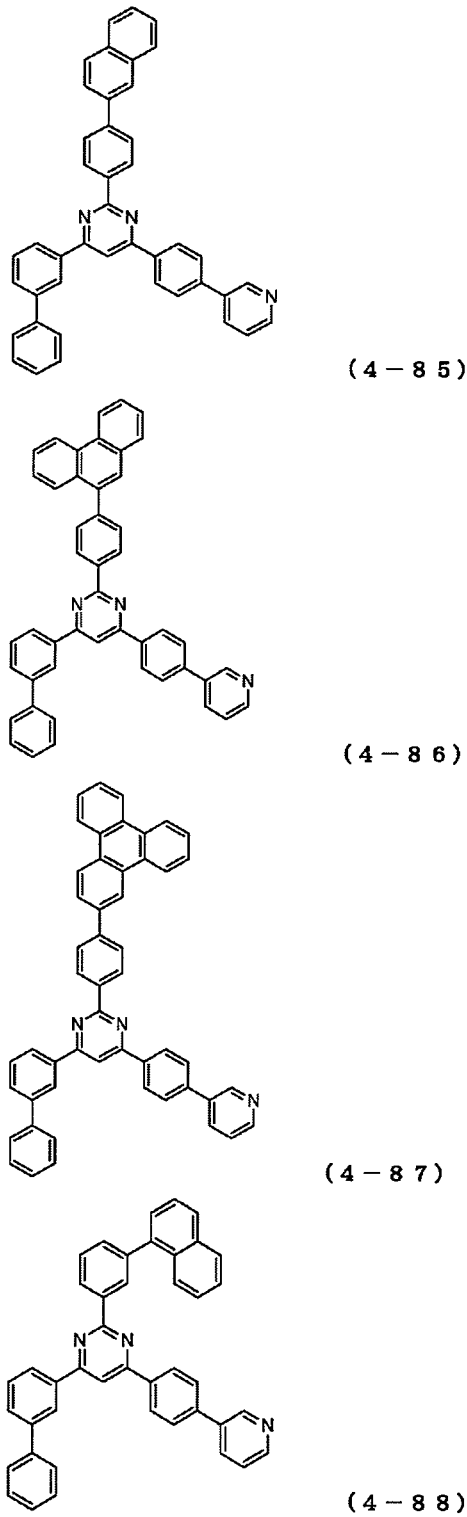
FIG. 44 is a view showing the structural formulas of Compounds (4-85) to (4-88) which are pyrimidine derivatives of the general formula (4).
Figure 45:
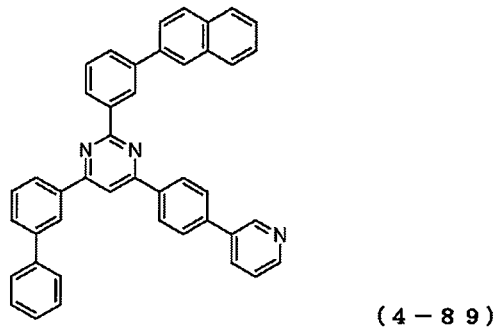
FIG. 45 is a view showing the structural formulas of Compounds (4-89) to (4-92) which are pyrimidine derivatives of the general formula (4).
Figure 45:
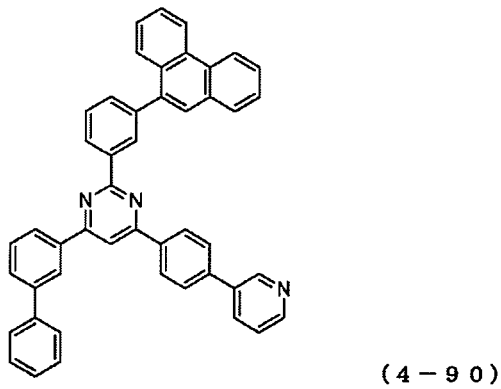
Figure 45:
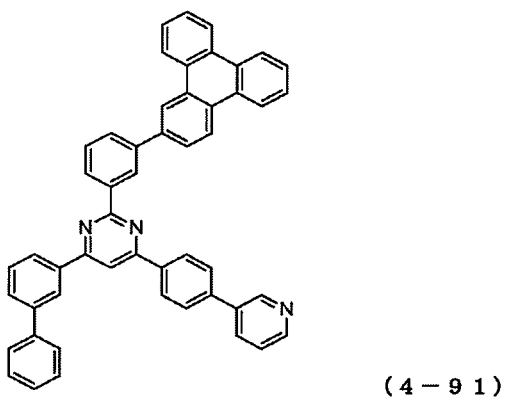
Figure 45:
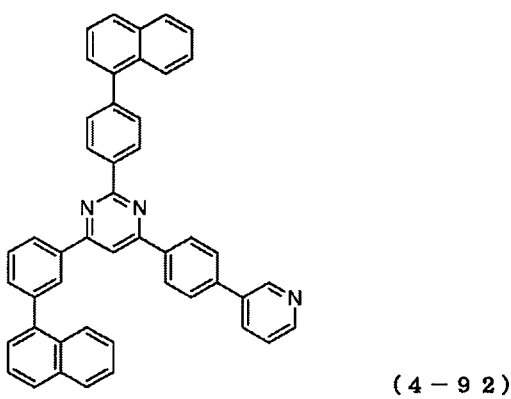
Figure 46:
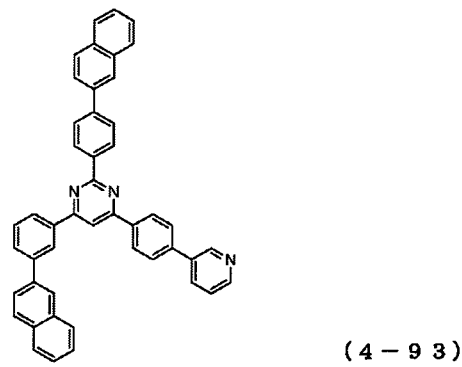
FIG. 46 is a view showing the structural formulas of Compounds (4-93) to (4-96) which are pyrimidine derivatives of the general formula (4).
Figure 46:
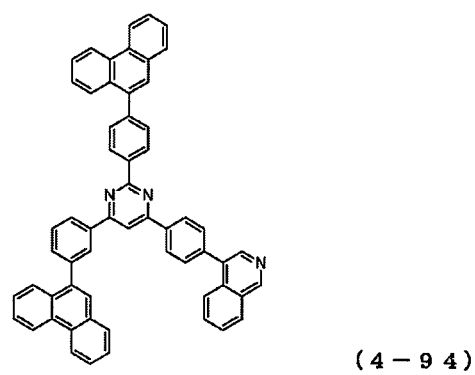
Figure 46:
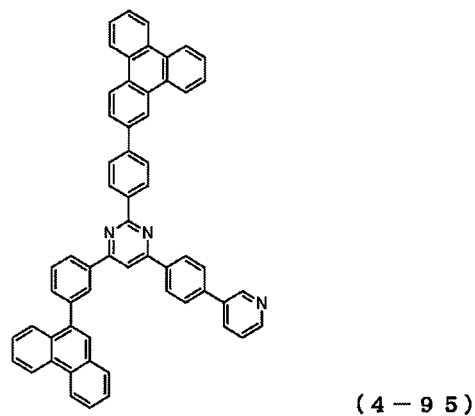
Figure 46:
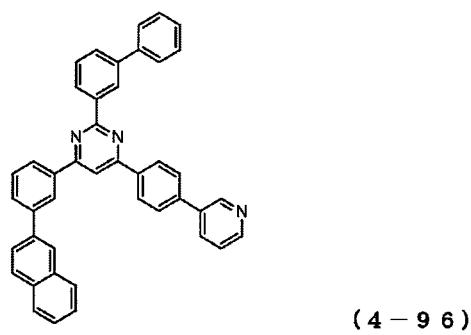
Figure 47:
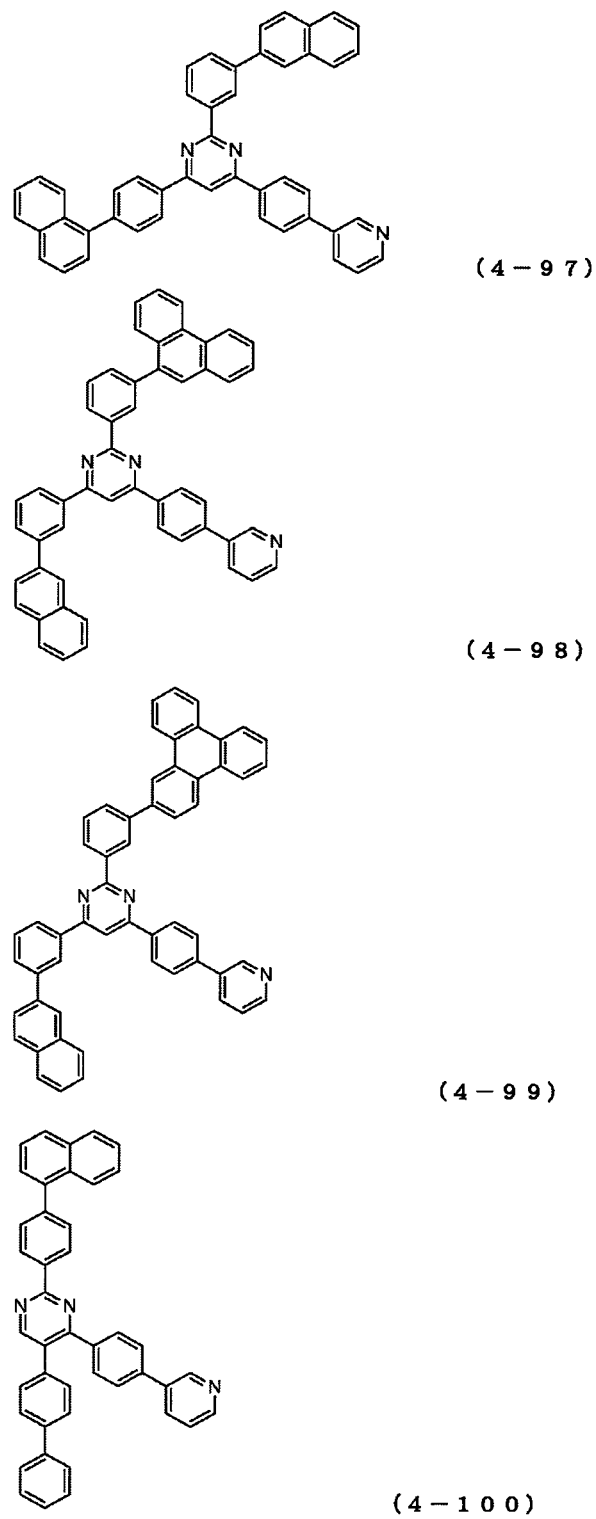
FIG. 47 is a view showing the structural formulas of Compounds (4-97) to (4-100) which are pyrimidine derivatives of the general formula (4).
Figure 48:
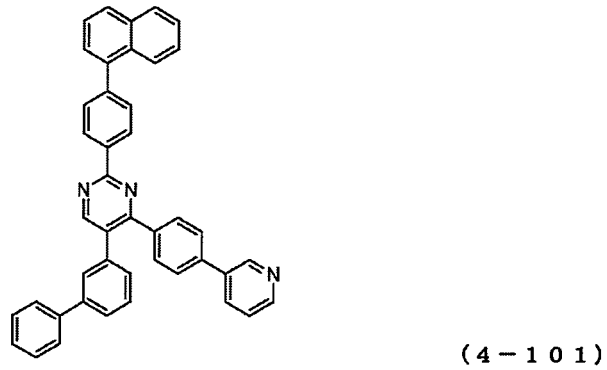
FIG. 48 is a view showing the structural formulas of Compounds (4-101) to (4-104) which are pyrimidine derivatives of the general formula (4).
Figure 48:
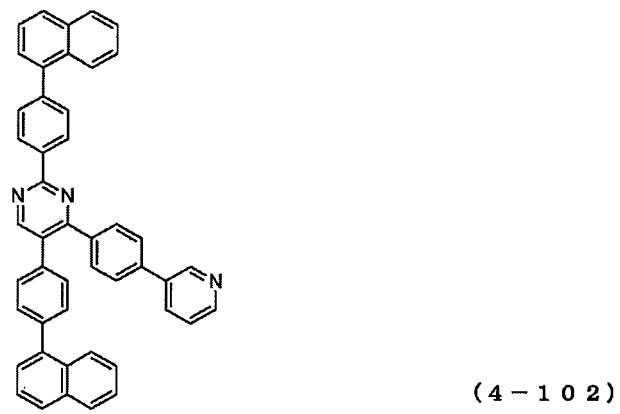
Figure 48:
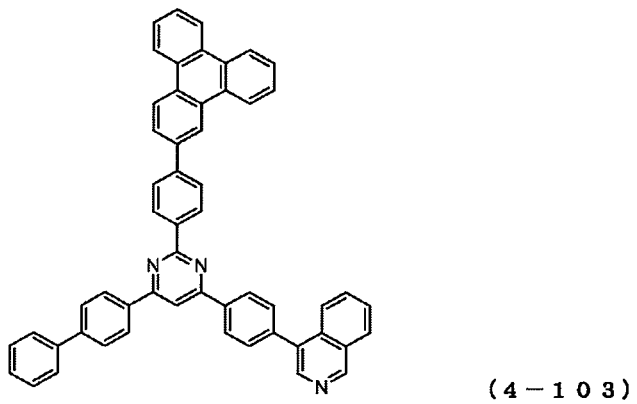
Figure 48:
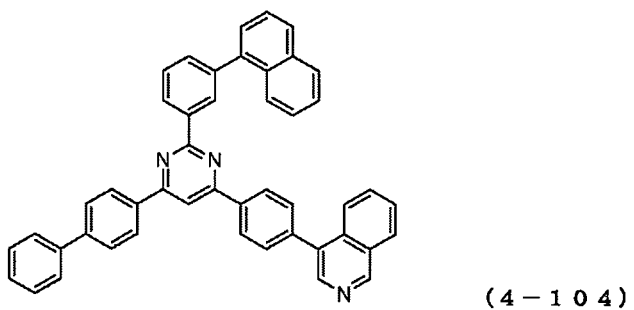
Figure 49:
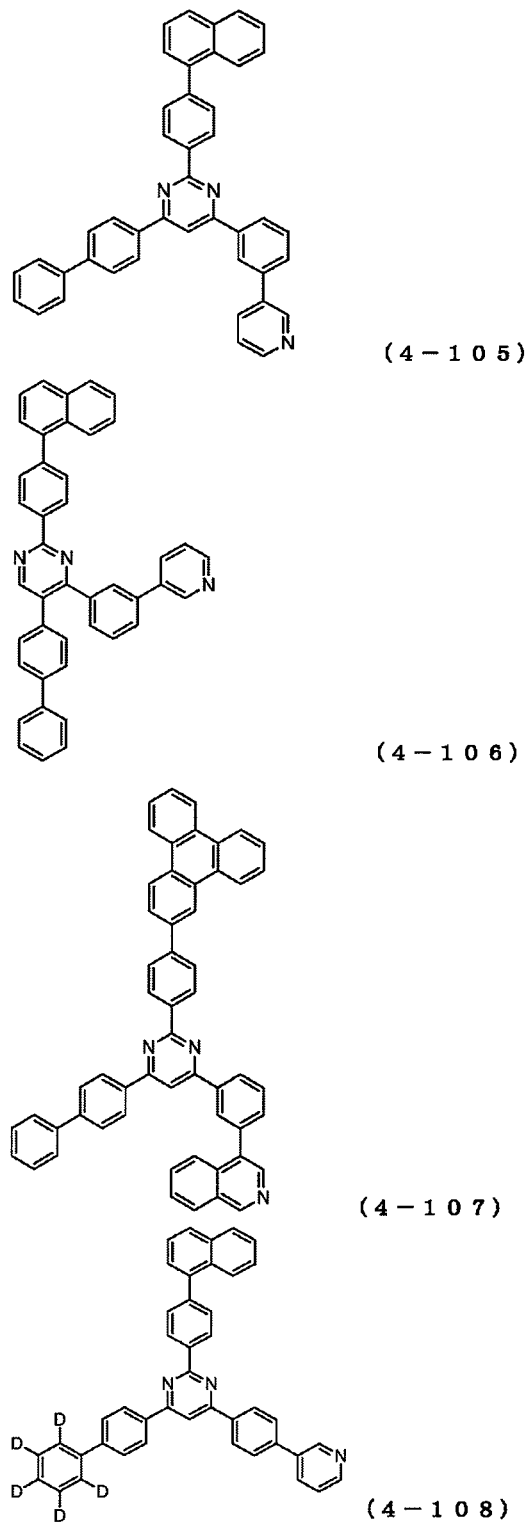
FIG. 49 is a view showing the structural formulas of Compounds (4-105) to (4-108) which are pyrimidine derivatives of the general formula (4).
Figure 50:
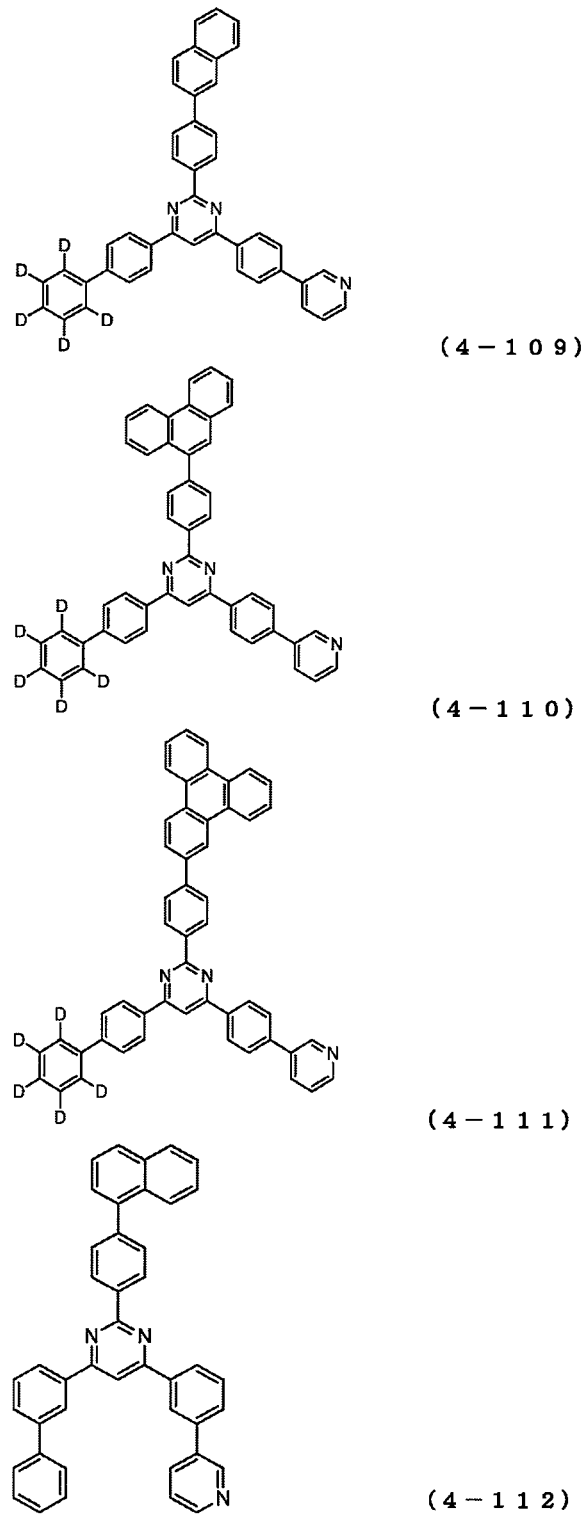
FIG. 50 is a view showing the structural formulas of Compounds (4-109) to (4-112) which are pyrimidine derivatives of the general formula (4).
Figure 51:
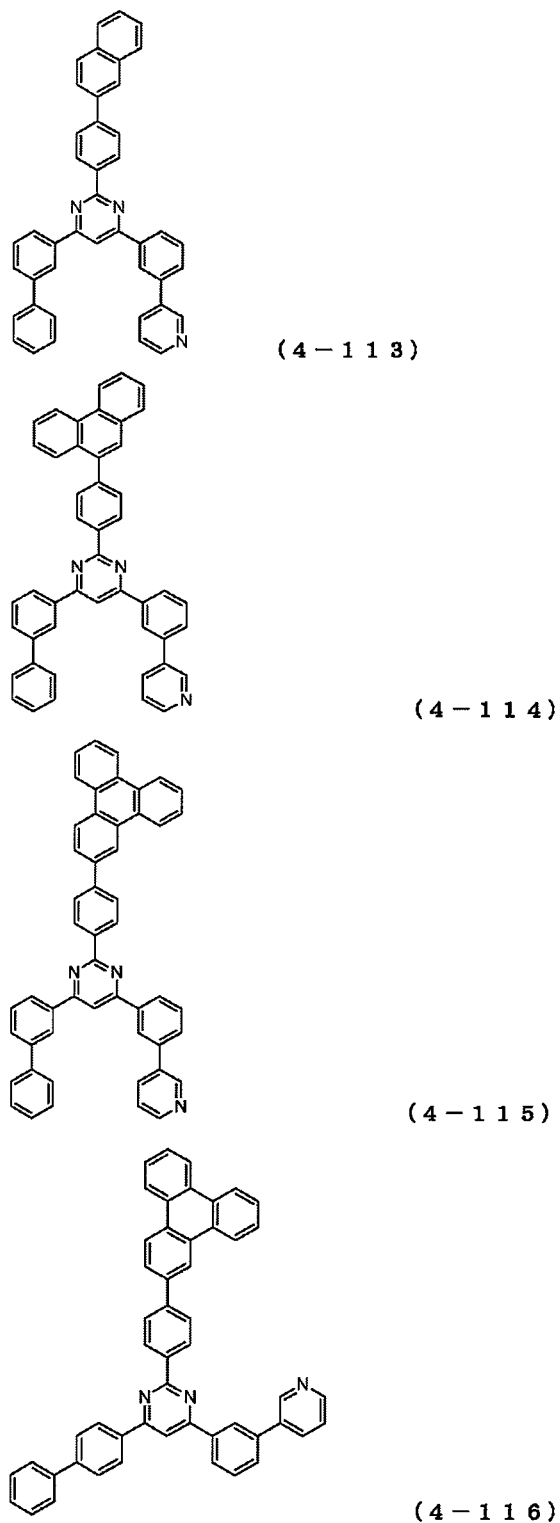
FIG. 51 is a view showing the structural formulas of Compounds (4-113) to (4-116) which are pyrimidine derivatives of the general formula (4).
Figure 52:
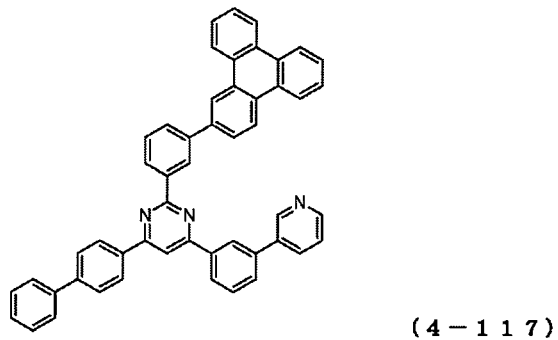
FIG. 52 is a view showing the structural formulas of Compounds (4-117) to (4-120) which are pyrimidine derivatives of the general formula (4).
Figure 52:
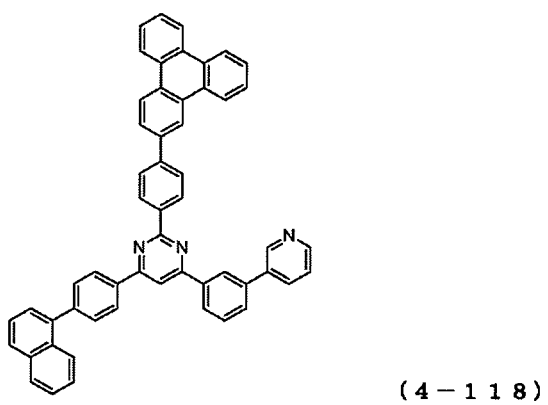
Figure 52:
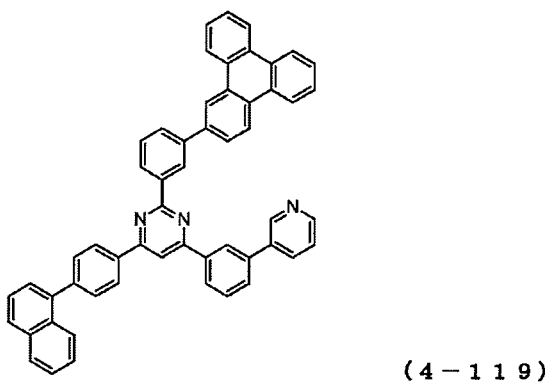
Figure 52:
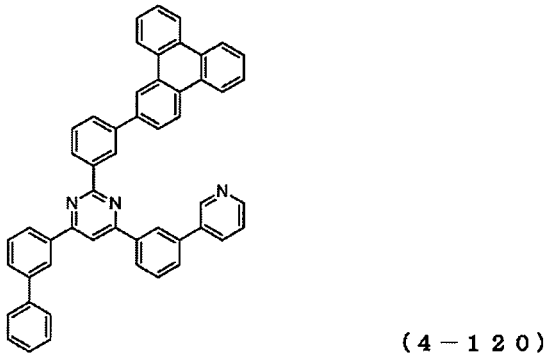
Figure 53:
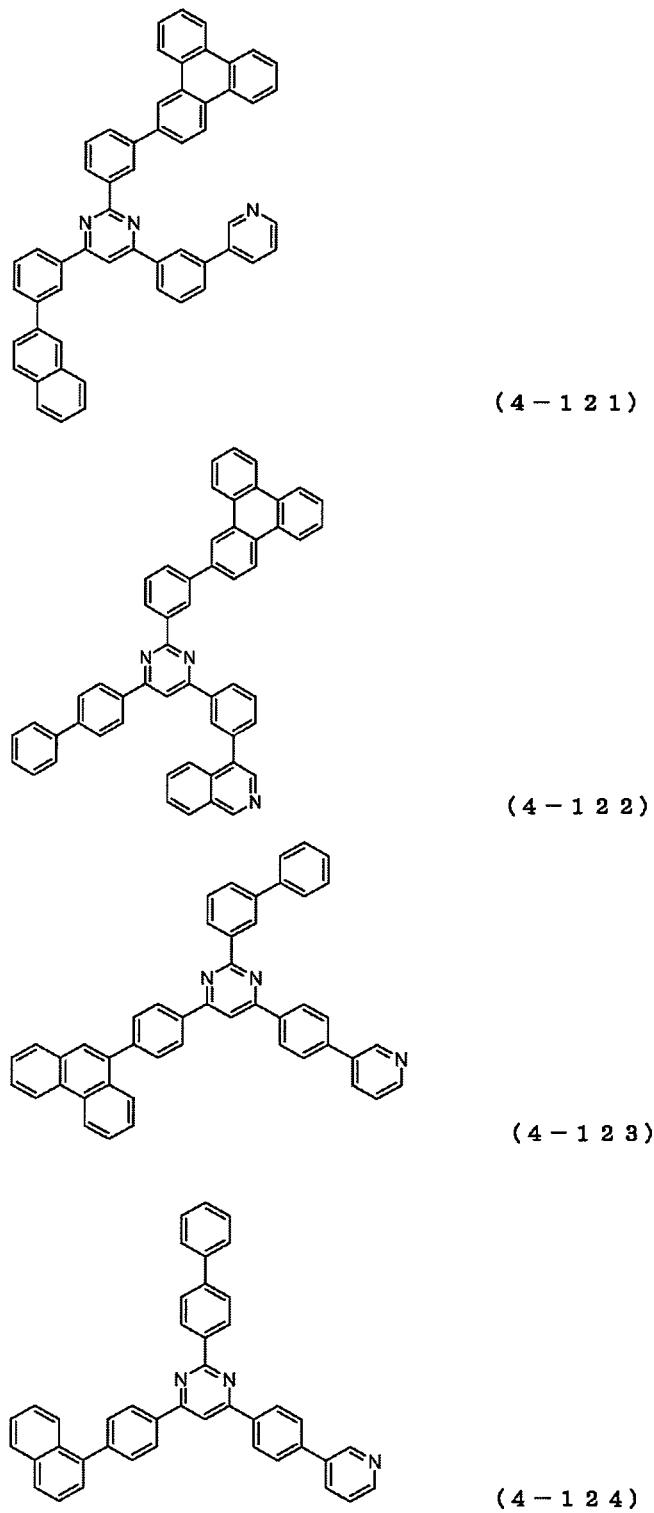
FIG. 53 is a view showing the structural formulas of Compounds (4-121) to (4-124) which are pyrimidine derivatives of the general formula (4).
Figure 54:
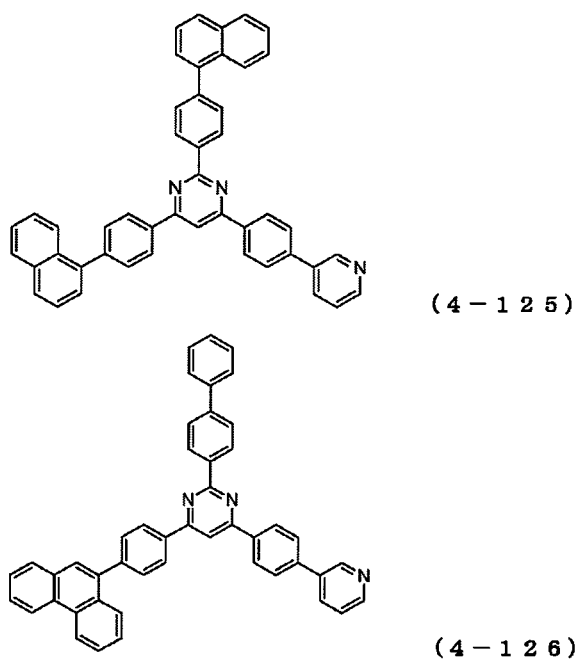
FIG. 54 is a view showing the structural formulas of Compounds (4-125) to (4-126) which are pyrimidine derivatives of the general formula (4).
Figure 55:
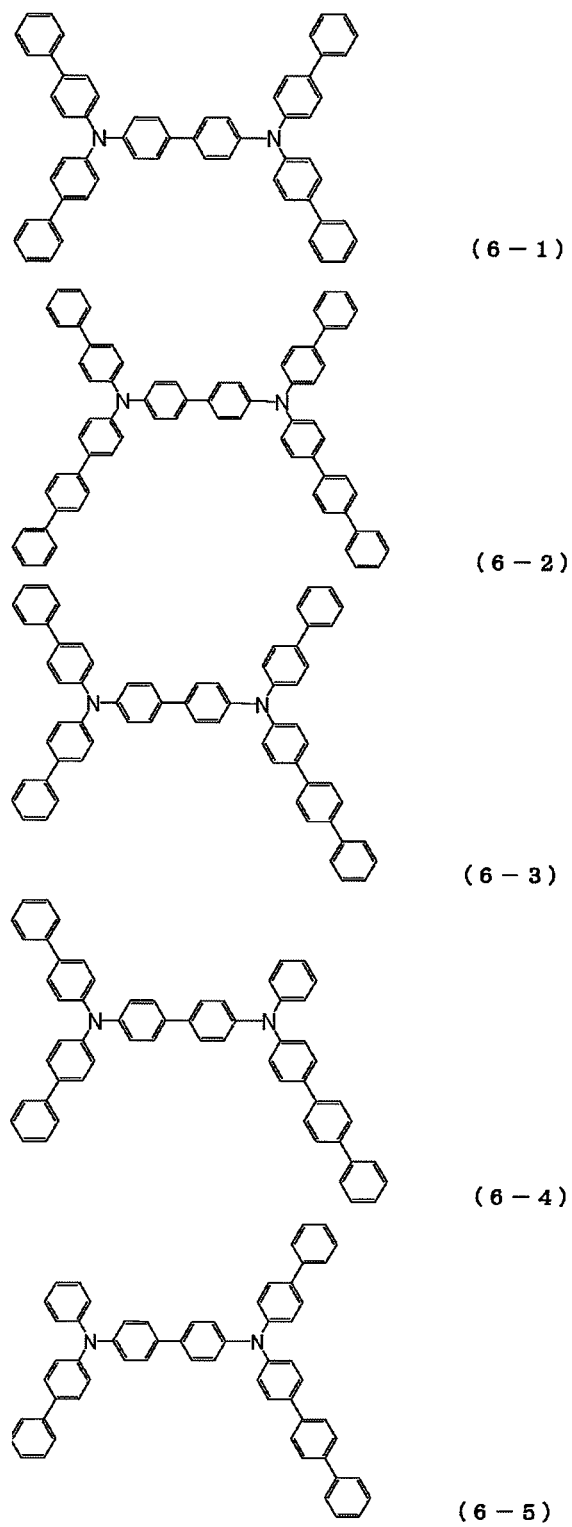
FIG. 55 is a view showing the structural formulas of Compounds (6-1) to (6-5) which are triarylamine compounds of the general formula (6).
Figure 56:
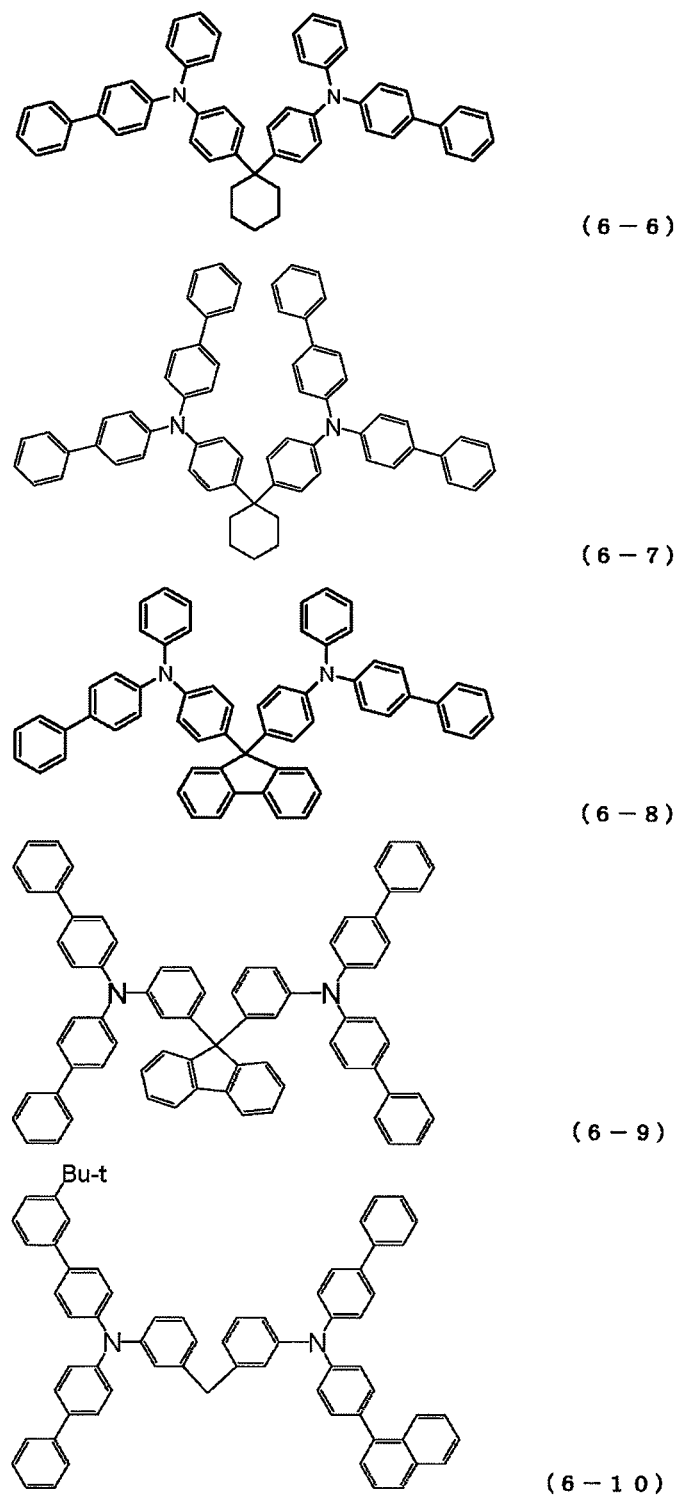
FIG. 56 is a view showing the structural formulas of Compounds (6-6) to (6-10) which are triarylamine compounds of the general formula (6).

It is not necessary for $R^{11}$ to $R^{14}$ to be present independently of each other to avoid formation of a ring. However, they may be bonded to each other via a single bond, a substituted or unsubstituted methylene group, an oxygen atom, or a sulfur atom to form a ring. Similarly, it is not necessary for $R^{15}$ to $R^{18}$ to be present independently of each other to avoid formation of a ring. However, they may be bonded to each other via a single bond, a substituted or unsubstituted methylene group, an oxygen atom, or a sulfur atom to form a ring. Moreover, like Compound 3-1 to Compound 3-6 in FIG. 23, part of $R^1$ to $R^{14}$ may be detached, and remaining group of $R^{11}$ to $R^{14}$ may be bonded to a vacancy, which has been produced by the detachment, via a substituted or unsubstituted methylene group, an oxygen atom, a sulfur atom, or a monoarylamino group to form a ring. Likewise, part of $R^{15}$ to $R^{18}$ may be detached, and remaining group of $R^{15}$ to $R^{18}$ may be bonded to a vacancy, produced by the detachment, via a substituted or unsubstituted methylene group, an oxygen atom, a sulfur atom, or a monoarylamino group to form a ring.

An embodiment in which $R^{11}$ to $R^{18}$ together form a ring, and the group contributing to ring formation is a di-substituted amino group, as mentioned above, includes an embodiment in which $R^{11}$ to $R^{18}$ bind to each other via a single bond, a substituted or unsubstituted methylene group, an oxygen atom, or a sulfur atom, while being mediated by the aromatic hydrocarbon group, aromatic heterocyclic group, or condensed polycyclic aromatic group possessed by the di-substituted amino group, to form a ring. The above embodiment also includes an embodiment in which part of $R^{11}$ to $R^{14}$ is detached, and remaining group of $R^{11}$ to $R^{14}$ (i.e., di-substituted amino group) binds to a vacancy, which has been produced by the detachment, via a substituted or unsubstituted methylene group, an oxygen atom, a sulfur atom, or a monoarylamino group, while being mediated by the aromatic hydrocarbon group, aromatic heterocyclic group, or condensed polycyclic aromatic group possessed by the di-substituted amino group, to form a ring. The above-mentioned embodiment further includes an embodiment in which part of $R^{15}$ to $R^{18}$ is detached, and remaining group of $R^{15}$ to $R^{18}$ (i.e., di-substituted amino group) binds to a vacancy, which has been produced by the detachment, via a substituted or unsubstituted methylene group, an oxygen atom, a sulfur atom, or a monoarylamino group, while being mediated by the aromatic hydrocarbon group, aromatic heterocyclic group, or condensed polycyclic aromatic group possessed by the di-substituted amino group, to form a ring.

The monoarylamino group playing the role of a linking group for ring formation can be exemplified by the same one as the monoarylamino group as the linking group in the general formula (2). The monoarylamino group may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

Preferred as the embodiment of the carbazole derivative of the general formula (3) is an embodiment in which the adjacent two of $R^{15}$ to $R^{18}$ are each an alkenyl group having 2 to 6 carbon atoms, an aromatic hydrocarbon group, an aromatic heterocyclic group, or a condensed polycyclic aromatic group, and the adjacent two groups ($R^{15}$ to $R^{18}$) bind to each other via a single bond and, together with the benzene ring to which $R^{15}$ to $R^{18}$ are bound, and form a condensed ring. The alkenyl group having 2 to 6 carbon atoms, aromatic hydrocarbon group, aromatic heterocyclic group, or condensed polycyclic aromatic group preferred in this case is a vinyl group or a phenyl group. That is, in a preferred embodiment, these groups, together with the benzene ring to which $R^{15}$ to $R^{18}$ are bound, form a naphthalene ring, a phenanthrene ring, or a triphenylene ring.

Also preferred is an embodiment in which one of $R^{11}$ to $R^{14}$ is an aromatic hydrocarbon group, an aromatic heterocyclic group, or a condensed polycyclic aromatic group, and the group binds to the benzene ring to which $R^{11}$ to $R^{14}$ are bound via a linking group, such as a substituted or unsubstituted methylene group, an oxygen atom, a sulfur atom, or a monoarylamino group, to form a ring. The aromatic hydrocarbon group, the aromatic heterocyclic group, or the condensed polycyclic aromatic group preferred in this case is a phenyl group, an indenyl group, an indolyl group, a benzofuranyl group, or a benzothienyl group. Particularly preferred as such an embodiment in which $R^1$ to $R^{14}$ and the benzene ring, to which $R^{11}$ to $R^{14}$ are bound, bind together to form a ring is an embodiment represented by the general formula (3a-1), (3a-2), (3a-3), (3a-4) or (3b-1) shown below. Concretely, it is preferred that $R^{11}$ to $R^{14}$ and the benzene ring, to which $R^{11}$ to $R^{14}$ are bound, together form a fluorene ring, a carbazole ring, a dibenzofuran ring, a dibenzothiophene ring, an indenoindole ring, an indenobenzofuran ring, an indenobenzothiophene ring, a benzofuroindole ring, a benzothienoindole ring, or an indoloindole ring.

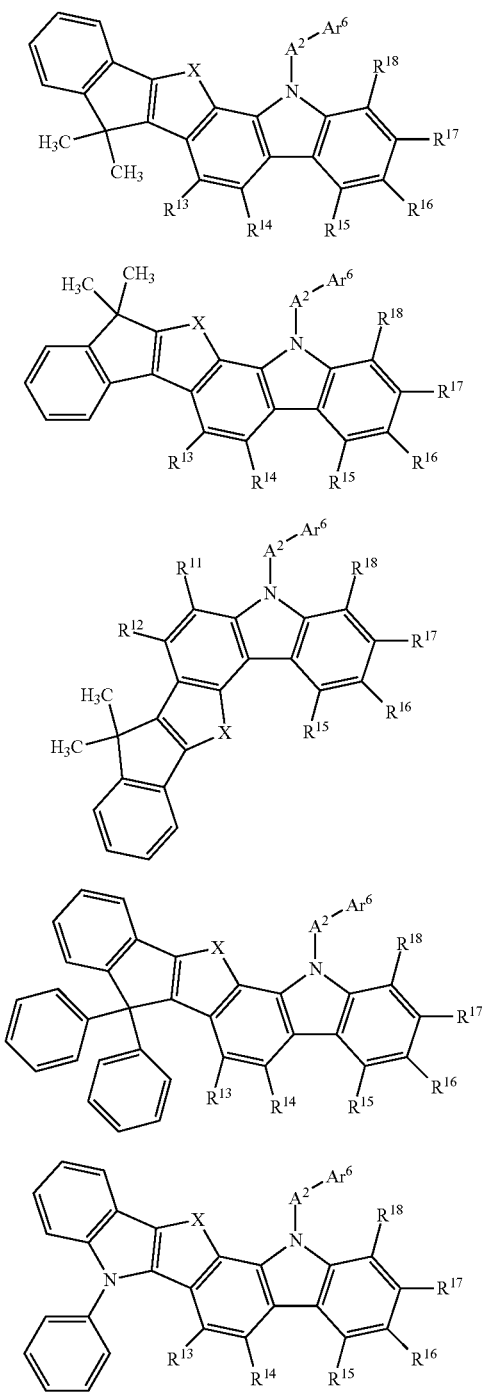

where X represents a substituted or unsubstituted methylene group, an oxygen atom, a sulfur atom, or a monoarylamino group, and $A^2$, $Ar^6$ and $R^{11}$ to $R^{18}$ have the meanings as indicated in the general formula (3).

Also preferred is an embodiment in which the adjacent two of, or all of, $R^{11}$ to $R^{14}$ are each a vinyl group, and the adjacent two vinyl groups bind to each other via a single bond to form a condensed ring, that is, an embodiment in which they form a naphthalene ring or a phenanthrene ring, together with the benzene ring to which $R^{11}$ to $R^{14}$ are bound.

An embodiment in which one of $R^{15}$ to $R^{18}$ is an aromatic hydrocarbon group, an aromatic heterocyclic group, or a condensed polycyclic aromatic group is also preferred. More preferably, one of $R^{15}$ to $R^{18}$ is a group selected from a fluorenyl group, a carbazolyl group, a dibenzofuranyl group, and a dibenzothienyl group. Particularly preferably, $R^{16}$ is a fluorenyl group, a carbazolyl group, a dibenzofuranyl group, or a dibenzothienyl group, and $R^{15}$, $R^{17}$ and $R^{18}$ are each a hydrogen atom.

Figure 20:
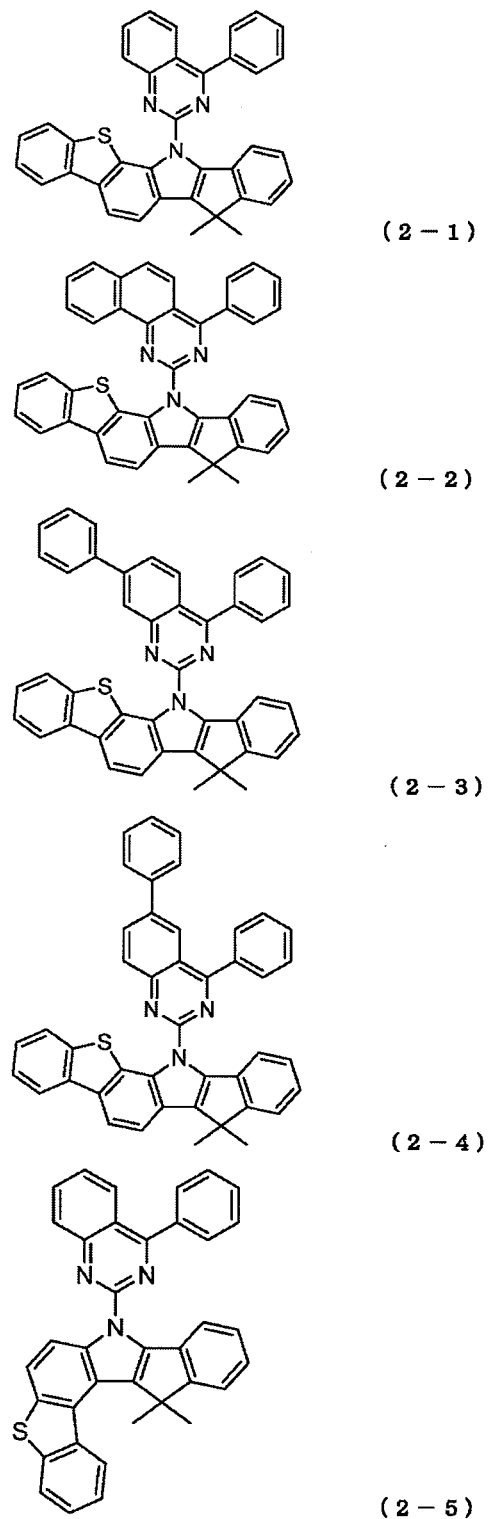
FIG. 20 is a view showing the structural formulas of Compounds (2-1) to (2-5) which are indenoindole derivatives of the general formula (2).
Figure 21:
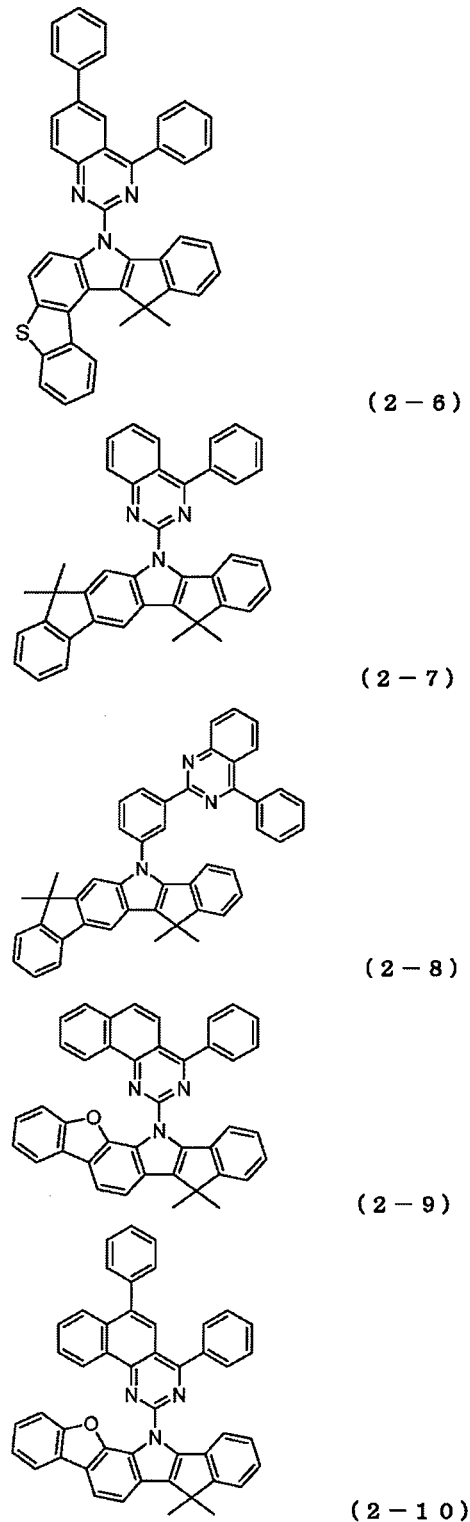
FIG. 21 is a view showing the structural formulas of Compounds (2-6) to (2-10) which are indenoindole derivatives of the general formula (2).
Figure 22:
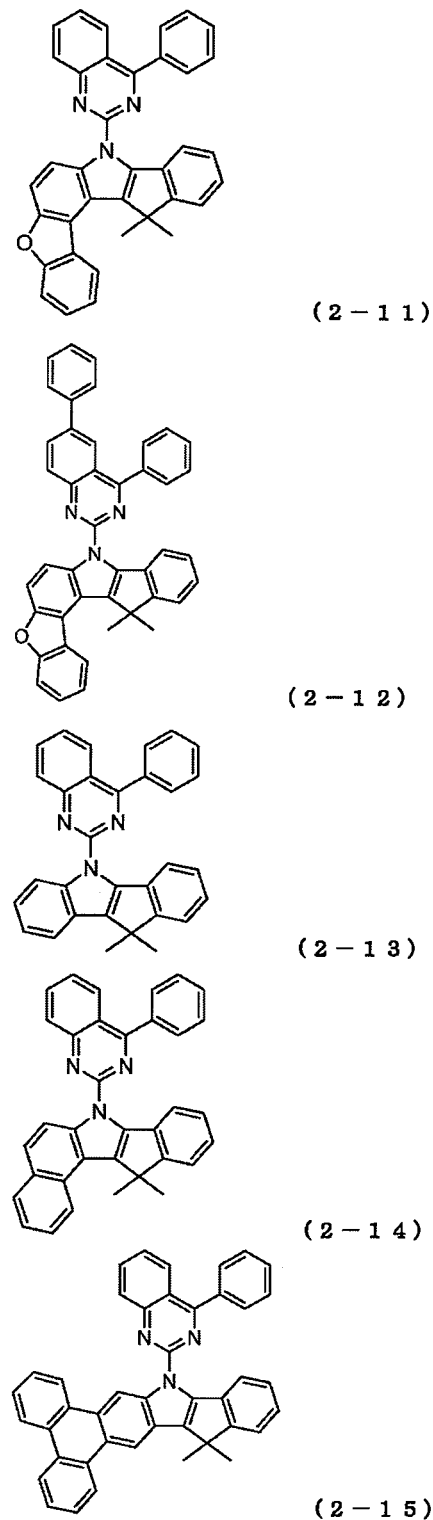
FIG. 22 is a view showing the structural formulas of Compounds (2-11) to (2-15) which are indenoindole derivatives of the general formula (2).

Examples of the preferred compounds among the indenoindole derivatives of the general formula (2) are shown in FIGS. 20 to 22. However, the indenoindole derivatives of the general formula (2) are not limited to these exemplary compounds.

Of the exemplary compounds in FIGS. 20 to 22, the compounds corresponding to the formula (2a) are (2-1) to (2-4) and (2-9) to (2-10). The compounds corresponding to the formula (2b) are (2-5) to (2-6) and (2-11) to (2-12). The compounds corresponding to the formula (2c) are (2-7) to (2-8). The compound corresponding to the formula (2d) is (2-14). The compound corresponding to the formula (2e) is (2-15).

Examples of the preferred compounds among the carbazole derivatives of the general formula (3) are shown in FIGS. 23 to 26. However, the carbazole derivatives of the general formula (3) are not limited to these exemplary compounds.

Of the exemplary compounds in FIGS. 23 to 26, the compounds corresponding to the formula (3a-1) are (3-1) to (3-6), (3-8) to (3-10), (3-12) and (3-15). The compound corresponding to the formula (3a-2) is (3-14). The compound corresponding to the formula (3a-3) is (3-7). The compound corresponding to the formula (3a-4) is (3-11). The compound corresponding to the formula (3b-1) is (3-13).

The indenoindole derivatives of the general formula (2) and the carbazole derivatives of the general formula (3), mentioned above, can be synthesized in accordance with publicly known methods (see Patent Document 6).

The indenoindole derivatives of the general formula (2) and the carbazole derivatives of the general formula (3) are compounds excellent in luminous efficiency as compared with conventional materials, and they are preferred as host materials for the luminous layer, in particular, as host materials for the luminous layer containing phosphorescent luminous materials.

For the luminous layer in the organic EL device of the present invention, publicly known luminous materials, such as various metal complexes, for example, metal complexes of quinolinol derivatives including $Alq_3$; anthracene derivatives; bisstyrylbenzene derivatives; pyrene derivatives; oxazole derivatives; and polyparaphenylenevinylene derivatives, can be used in combination, as far as they do not impair the excellent characteristics of the indenoindole derivatives of the general formula (2) or the carbazole derivatives of the general formula (3).

In the present invention, the luminous layer may be composed of a host material and a dopant material. Examples of the host material include the indenoindole derivatives of the general formula (2); the carbazole derivatives of the general formula (3); the aforementioned luminous materials; thiazole derivatives; benzimidazole derivatives; and polydialkylfluorene derivatives. Preferred are the indenoindole derivatives of the general formula (2), or the carbazole derivatives of the general formula (3).

As the dopant material, there can be used quinacridone, coumarin, rubrene, perylene, pyrene and derivatives thereof;

benzopyran derivatives; indenophenanthrene derivatives; rhodamine derivatives; aminostyryl derivatives and the like.

Furthermore, a phosphorescent luminous material can be preferably used as the luminous material. As the phosphorescent luminous material, a phosphorescent luminous body in the form of a metal complex containing iridium, platinum or the like can be used. For example, a green phosphorescent luminous body such as Ir(ppy)$_3$; a blue phosphorescent luminous body such as FIrpic or FIr6; or a red phosphorescent luminous body such as Btp$_2$Ir(acac) is used.

As the host material in this case, the indenoindole derivative of the general formula (2) or the carbazole derivative of the general formula (3) can be used. Moreover, use can be made of the following hole injecting/transporting host material:

a carbazole derivative, for example,
4,4'-di(N-carbazolyl)biphenyl (CBP),
TCTA, or
mCP.
The following electron transporting host material is also usable:
p-bis(triphenylsilyl)benzene (UGH2); or
2,2',2''-(1,3,5-phenylene)-tris(1-phenyl-1H-benzimidazole) (TPBI).
By using such a host material, a high performance organic EL device can be prepared.

Doping of the host material with the phosphorescent luminous material is preferably performed by codeposition in a range of 1 to 30% by weight based on the entire luminous layer in order to avoid concentration quenching.

In the present invention, moreover, a material which emits delayed fluorescence, such as a CDCB derivative, for example, PIC-TRZ, CC2TA, PXZ-TRZ, or 4CzIPN, can be used as the luminous material.

In the present invention, a red luminous material is used preferably as the luminous material to be combined with the indenoindole derivative of the general formula (2) or the carbazole derivative of the general formula (3).

<Electron transport layer 7>

In the present invention, the electron transport layer 7 is provided on the above-described luminous layer 6. The electron transport layer 7 may be formed from a publicly known electron transport material. For example, it may be formed from various metal complexes such as metal complexes of quinolinol derivatives including Alq$_3$ and BAlq; triazole derivatives; triazine derivatives; oxadiazole derivatives; pyridine derivatives; anthracene derivatives; benzimidazole derivatives; thiadiazole derivatives; benzotriazole derivatives; carbodiimide derivatives; quinoxaline derivatives; pyridoindole derivatives; phenanthroline derivatives; and silole derivatives.

In the present invention, moreover, it is preferred that a pyrimidine derivative represented by the general formula (4) (may herein be referred to simply as a "pyrimidine derivative of the general formula (4)") shown below be used as an electron transport material to form the electron transport layer. It is more preferred that a pyrimidine derivative represented by the general formula (4a) or (4b) shown below be used as an electron transport material to form the electron transport layer. Such a pyrimidine derivative is excellent in electron injecting and transporting capabilities, and also excels in thin film stability and durability. The electron transport layer containing such a pyrimidine derivative is improved in the efficiency of electron transport from the electron transport layer to the luminous layer.

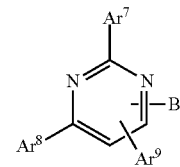

(4)

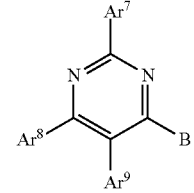

(4a)

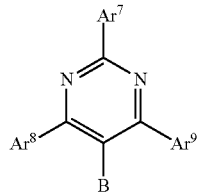

(4b)

(Ar$^7$ to Ar$^9$)

In the general formulas (4), (4a) and (4b), Ar$^7$ represents an aromatic hydrocarbon group, an aromatic heterocyclic group, or a condensed polycyclic aromatic group; Ar$^8$ and Ar$^9$ each represent a hydrogen atom, an aromatic hydrocarbon group, an aromatic heterocyclic group, or a condensed polycyclic aromatic group; and Ar$^8$ and Ar$^9$ are each not a hydrogen atom at the same time.

Examples of the aromatic hydrocarbon group, the aromatic heterocyclic group, or the condensed polycyclic aromatic group, represented by Ar$^7$ to Ar$^9$, include a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, a spirobifluorenyl group, a furyl group, a thienyl group, a benzofuranyl group, a benzothienyl group, a dibenzofuranyl group, a dibenzothienyl group and the like.

The aromatic hydrocarbon group, the aromatic heterocyclic group, or the condensed polycyclic aromatic group, represented by Ar$^7$ to Ar$^9$, may each be unsubstituted, but may each have a substituent. The substituent can be exemplified by the following groups, in addition to a deuterium atom, a cyano group, and a nitro group:

a halogen atom, for example, a fluorine atom, a chlorine atom, a bromine atom, an iodine atom or the like;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, an n-hexyl group or the like;

an alkyloxy group having 1 to 6 carbon atoms, for example, a methyloxy group, an ethyloxy group, a propyloxy group or the like;

an alkenyl group, for example, a vinyl group, an allyl group or the like;

an aryloxy group, for example, a phenyloxy group, a tolyloxy group or the like;

an arylalkyloxy group, for example, a benzyloxy group, a phenethyloxy group or the like;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a spirobifluorenyl group, an acenaphthenyl group or the like;

an aromatic heterocyclic group, for example, a pyridyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a carbolinyl group, an azaspirobifluorenyl group, a diazaspirobifluorenyl group or the like;

an arylvinyl group, for example, a styryl group a naphthylvinyl group or the like; and an acyl group, for example, an acetyl group, a benzoyl group or the like, The alkyl group having 1 to 6 carbon atoms, the alkenyl group, and the alkyloxy group having 1 to 6 carbon atoms may be straight-chain or branched. Any of the above exemplary substituents may be further substituted by the above exemplary substituent. The above exemplary substituents may be present independently of each other to avoid formation of a ring. However, they may be bonded to each other via a single bond, a substituted or unsubstituted methylene group, an oxygen atom, or a sulfur atom to form a ring. Further, these substituents and $Ar^7$, $Ar^8$ or $Ar^9$, to which these substituents are bound, may be bonded to each other via an oxygen atom or a sulfur atom to form a ring.

Preferred as $Ar^7$ is a phenyl group; a biphenylyl group; a naphthyl group; an anthracenyl group; an acenaphthenyl group; a phenanthrenyl group; a fluorenyl group; an indenyl group; a pyrenyl group; a perylenyl group; a fluoranthenyl group; a triphenylenyl group; a spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group. More preferred as $Ar^7$ is a phenyl group, a biphenylyl group, a naphthyl group, a phenanthrenyl group, a fluorenyl group, a pyrenyl group, a fluoranthenyl group, a triphenylenyl group, a spirobifluorenyl group, a dibenzofuranyl group, or a dibenzothienyl group.

If $Ar^7$ is a phenyl group, this phenyl group preferably has a substituted or unsubstituted condensed polycyclic aromatic group or phenyl group as a substituent, and more preferably has a substituent selected from a naphthyl group, a phenanthrenyl group, a pyrenyl group, a fluoranthenyl group, a triphenylenyl group, a spirobifluorenyl group, and a phenyl group. Also preferably, the substituent possessed by the phenyl group and the phenyl group bind to each other via an oxygen atom or a sulfur atom to form a ring.

Preferred as $Ar^8$ is a phenyl group having a substituent; a substituted or unsubstituted spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group.

As the substituent for the phenyl group in this case, an aromatic hydrocarbon group, for example, a phenyl group, a biphenylyl group, or a terphenyl group; a condensed polycyclic aromatic group, for example, a naphthyl group, an acenaphthenyl group, a phenanthrenyl group, a fluorenyl group, an indenyl group, a pyrenyl group, a perylenyl group, a fluoranthenyl group, a triphenylenyl group, or a spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group; is preferred and, a phenyl group, a naphthyl group, a phenanthrenyl group, a fluorenyl group, a pyrenyl group, a fluoranthenyl group, a triphenylenyl group, a spirobifluorenyl group, a dibenzofuranyl group, or a dibenzothienyl group is more preferred. It is also preferred that the substituent possessed by the phenyl group and the phenyl group bind to each other via an oxygen atom or a sulfur atom to form a ring.

Preferred as $Ar^9$ is a hydrogen atom; a phenyl group having a substituent; a substituted or unsubstituted spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group.

As the substituent for the phenyl group in this case, an aromatic hydrocarbon group, for example, a phenyl group, a biphenylyl group, or a terphenyl group; a condensed polycyclic aromatic group, for example, a naphthyl group, an acenaphthenyl group, a phenanthrenyl group, a fluorenyl group, an indenyl group, a pyrenyl group, a perylenyl group, a fluoranthenyl group, a triphenylenyl group, or a spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group; is preferred, and a phenyl group, a naphthyl group, a phenanthrenyl group, a fluorenyl group, a pyrenyl group, a fluoranthenyl group, a triphenylenyl group, a spirobifluorenyl group, a dibenzofuranyl group, or a dibenzothienyl group is more preferred. It is also preferred that the substituent possessed by the phenyl group and the phenyl group bind to each other via an oxygen atom or a sulfur atom to form a ring.

It is preferred for one of $Ar^8$ and $Ar^9$ to be a hydrogen atom.

(B) In the above general formulas (4), (4a) and (4b), B represents a monovalent group represented by the structural formula (5) indicated below and, from the viewpoint of thin film stability, preferably represents a monovalent group represented by the structural formula (5a) indicated below. In the structural formula (5a), the position of binding of $Ar^{10}$ in the benzene ring is the meta-position with respect to the position of binding to the pyrimidine ring represented by the general formula (4).

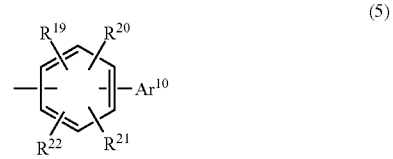

(5)

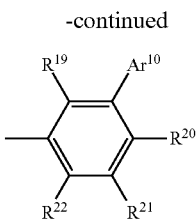

(5a)

In the structural formulas (5) and (5a), $Ar^{10}$ represents an aromatic heterocyclic group. Examples of the aromatic heterocyclic group represented by $Ar^{10}$ include a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a naphthyridinyl group, a phenanthrolinyl group, an acridinyl group, a carbolinyl group, an azaspirobifluorenyl group, a diazaspirobifluorenyl group and the like.

The aromatic heterocyclic group represented by $Ar^{10}$ may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^7$ to $Ar^9$ in the general formula (4) may have. The same holds true of the embodiments that the substituents can adopt.

As $Ar^{10}$, a nitrogen-containing heterocyclic group, for example, a triazinyl group, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzimidazolyl group, a pyrazolyl group, an azafluorenyl group, a diazafluorenyl group, a naphthyridinyl group, a phenanthrolinyl group, an acridinyl group, a carbolinyl group, an azaspirobifluorenyl group, or a diazaspirobifluorenyl group is preferred; a triazinyl group, a pyridyl group, a pyrimidinyl group, a quinolyl group, an isoquinolyl group, an indolyl group, a quinoxalinyl group, an azafluorenyl group, a diazafluorenyl group, a benzimidazolyl group, a naphthyridinyl group, a phenanthrolinyl group, an acridinyl group, an azaspirobifluorenyl group, or a diazaspirobifluorenyl group is more preferred; and a pyridyl group, a pyrimidinyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, or a diazaspirobifluorenyl group is particularly preferred.

In the structural formulas (5) and (5a), $R^{19}$ to $R^{22}$ each represent a hydrogen atom, a deuterium atom, a fluorine atom, a chlorine atom, a cyano group, a trifluoromethyl group, an alkyl group having 1 to 6 carbon atoms, an aromatic hydrocarbon group, an aromatic heterocyclic group, or a condensed polycyclic aromatic group. The alkyl group having 1 to 6 carbon atoms may be straight-chain or branched. $R^{19}$ to $R^{22}$ and $Ar^{10}$ may be present independently of each other so as not to form a ring. However, they may be bonded to each other via a single bond, a substituted or unsubstituted methylene group, an oxygen atom, or a sulfur atom to form a ring.

The alkyl group having 1 to 6 carbon atoms, represented by $R^{19}$ to $R^{22}$, can be exemplified by a methyl group, an ethyl group, an n-propyl group, an i-propyl group, an n-butyl group, a 2-methylpropyl group, a t-butyl group, an n-pentyl group, a 3-methylbutyl group, a tert-pentyl group, an n-hexyl group, an iso-hexyl group, a tert-hexyl group and the like.

The alkyl group having 1 to 6 carbon atoms, represented by $R^{19}$ to $R^{22}$, may be unsubstituted, but may have a substituent. The substituent can be exemplified by the same ones as those shown as the substituents that the alkyl group having 1 to 6 carbon atoms, the cycloalkyl group having 5 to 10 carbon atoms, or the alkenyl group having 2 to 6 carbon atoms, represented by $R^1$ to $R^8$ in the general formula (2), may have. The same holds true of the embodiments that the substituents can adopt.

Examples of the aromatic hydrocarbon group, the aromatic heterocyclic group, or the condensed polycyclic aromatic group, represented by $R^{19}$ to $R^{22}$, include a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, a spirobifluorenyl group, a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a naphthyridinyl group, a phenanthrolinyl group, an acridinyl group, a carbolinyl group, a phenoxazinyl group, a phenothiazinyl group, a phenazinyl group, an azaspirobifluorenyl group, a diazaspirobifluorenyl group and the like.

The aromatic hydrocarbon group, the aromatic heterocyclic group, or the condensed polycyclic aromatic group, represented by $R^{19}$ to $R^{22}$, may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^7$ to $Ar^9$ in the general formula (4) may have. The same holds true of the embodiments that the substituents can adopt.

Concrete examples of the preferred compounds among the pyrimidine derivatives represented by the general formula (4) are shown in FIGS. 27 to 54. However, such pyrimidine derivatives are not limited to these exemplary compounds. D in the structural formulas represents a deuterium atom.

Of the exemplary compounds in FIGS. 27 to 54, the compounds corresponding to the formula (4a) are (4-1) to (4-49), (4-66) to (4-99), (4-103) to (4-105) and (4-107) to (4-126). The compounds corresponding to the formula (4b) are (4-50) to (4-65). The compounds in which the group B is a monovalent group represented by the structural formula (5a) are (4-1) to (4-66), (4-68), (4-71) to (4-72), (4-105) to (4-107) and (4-112) to (4-122).

The pyrimidine derivatives of the general formula (4), mentioned above, can be synthesized in accordance with a publicly known method (see Patent Document 7).

The above-described electron transport material may be subjected singly to film formation, but may be mixed with other materials and subjected to film formation.

<Electron injection layer 8>

The organic EL device of the present invention may have the electron injection layer 8 between the electron transport layer 7 and the cathode 9. The electron injection layer 8 may contain an alkali metal salt such as lithium fluoride or cesium fluoride; an alkaline earth metal salt such as magnesium fluoride; a metal oxide such as aluminum oxide or the like. However, such a material can be omitted in the suitable selection of the electron transport layer and the cathode.

<Cathode 9>

In connection with the cathode 9 in the organic EL device of the present invention, a metal with a low work function such as aluminum, or an alloy having a lower work function, such as a magnesium-silver alloy, a magnesium-indium alloy, or an aluminum-magnesium alloy, is used as an electrode material.

<Other Layers>

The organic EL device of the present invention may have other layers, if desired. For example, an electron blocking layer can be provided between the hole transport layer 5 and the luminous layer 6, and a hole blocking layer can be provided between the luminous layer 6 and the electron transport layer 7, although they are not shown in FIG. 1.

Electron blocking layer:

For the electron blocking layer, publicly known compounds having electron blocking action can be used. As the publicly known compounds, the following can be exemplified:

carbazole derivatives, for example,
4,4',4''-tri(N-carbazolyl)triphenylamine (TCTA);
9,9-bis[4-(carbazol-9-yl)phenyl]fluorene;
1,3-bis(carbazol-9-yl)benzene (mCP); and
2,2-bis(4-carbazol-9-ylphenyl)adamantane (Ad-Cz). compounds having a triphenylsilyl group and a triarylamine structure, for example,
9-[4-(carbazol-9-yl)phenyl]-9-[4-(triphenylsilyl) phenyl]-9H-fluorene.

For the electron blocking layer, the arylamine compound represented by the general formula (1) can be used suitably because of its high electron blocking performance. In this case, however, the composition of the electron blocking layer and the composition of the hole transport layer have to be different. These materials may be subjected singly to film formation, but may be mixed with other materials and subjected to film formation.

Hole Blocking Layer:

The hole blocking layer can use compounds having hole blocking action, such as phenanthroline derivatives, e.g., bathocuproine (BCP), metal complexes of quinolinol derivatives, e.g., aluminum(III) bis(2-methyl-8-quinolinate)-4-phenylphenolate (BAlq), various rare earth complexes, triazole derivatives, triazine derivatives, and oxadiazole derivatives. These materials may be subjected singly to film formation, but may be mixed with other materials and subjected to film formation. These materials may also concurrently serve as the materials for the electron transport layer.

Each layer constituting the organic EL device of the present invention may be structured in a single layer or in a plurality of layers. In the present invention, in particular, in order to exhibit the excellent characteristics of the arylamine compound of the general formula (1), it is preferred to structure the hole transport layer 5 in two layers, the first hole transport layer 5a and the second hole transport layer 5b as shown in FIG. 1. The hole transport layer 5 of the two-layer structure will be described below.

<Hole Transport Layer 5 of Two-Layer Structure>

The organic EL device of the present invention uses the arylamine compound represented by the general formula (1) in forming the hole transport layer 5. The hole transport layer 5 containing such an arylamine compound is preferably configured as a two-layer structure. That is, as shown in FIG. 1, it is preferred that the hole transport layer 5 be configured to be of a two-layer structure in which it is divided into the first hole transport layer 5a located on a side of the anode 2, and the second hole transport layer 5b located on a side of the luminous layer 6.

In the second hole transport layer 5b, it is preferred to contain the arylamine compound of the general formula (1), because this compound shows high electron blocking performance. In this case, the aforementioned hole transporting material or the like can be used in combination with the arylamine compound of the general formula (1) for the second hole transport layer 5b.

The composition of the first hole transport layer 5a is different from the composition of the second hole transport layer 5b. Concretely, the first hole transport layer 5a can use, in addition to the above hole transporting material, a triarylamine compound which has 2 to 6 triarylamine structures in the molecule, and in which the triarylamine structures are linked to each other via a single bond, or a divalent group containing no hetero-atom, for example. This is because the arylamine skeleton shows excellent hole transporting properties.

Preferred as the above-mentioned triarylamine compound having 2 to 6 triarylamine structures is a triarylamine compound having 2 triarylamine structures, represented by the following general formula (6) (may herein be referred to simply as "triarylamine compound of the general formula (6)"), or a triarylamine compound having 4 triarylamine structures, represented by the following general formula (7) (may herein be referred to simply as "triarylamine compound of the general formula (7)").

Triarylamine compound of the general formula (6);

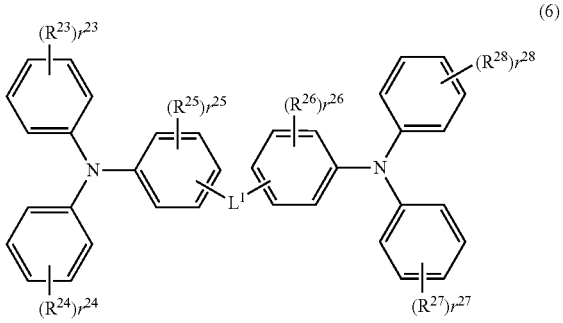

($r^{23}$ to $r^{28}$) In the general formula (6), $r^{23}$ to $r^{28}$ are each an integer showing the number of the substituents $R^{23}$'s to the substituents $R^{28}$'s bound to each benzene ring, $r^{23}$, $r^{24}$, $r^{27}$ and $r^{28}$ each denote an integer of 0 to 5, and $r^{25}$ and $r^{26}$ each denote an integer of 0 to 4. As $r^{23}$ to $r^{28}$, an integer of 0 to 3 is preferred, and an integer of 0 to 2 is more preferred.

If $r^{23}$ to $r^{28}$ are each 0, this means that there are none of $R^{23}$ to $R^{28}$ on the benzene rings. That is, the benzene rings are not substituted by groups represented by $R^{23}$ to $R^{28}$.

Figure 57:
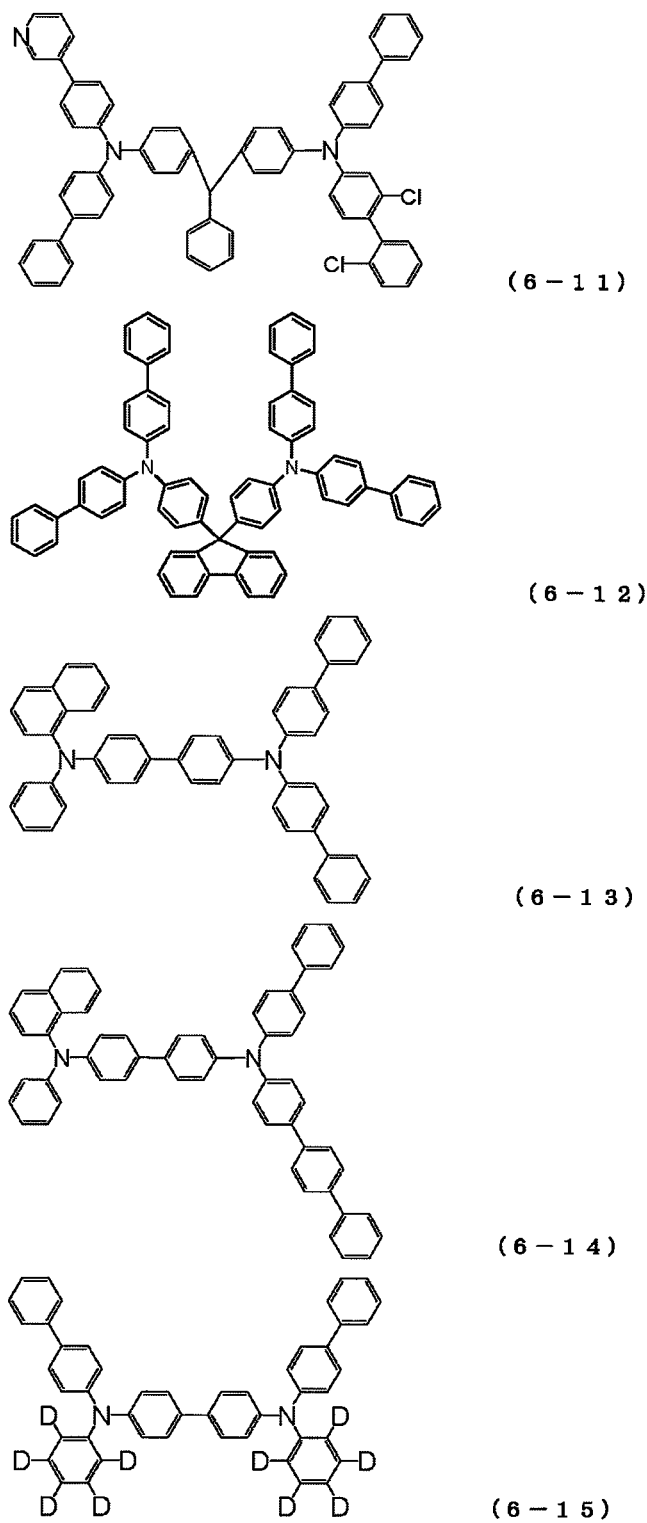
FIG. 57 is a view showing the structural formulas of Compounds (6-11) to (6-15) which are triarylamine compounds of the general formula (6).
Figure 58:
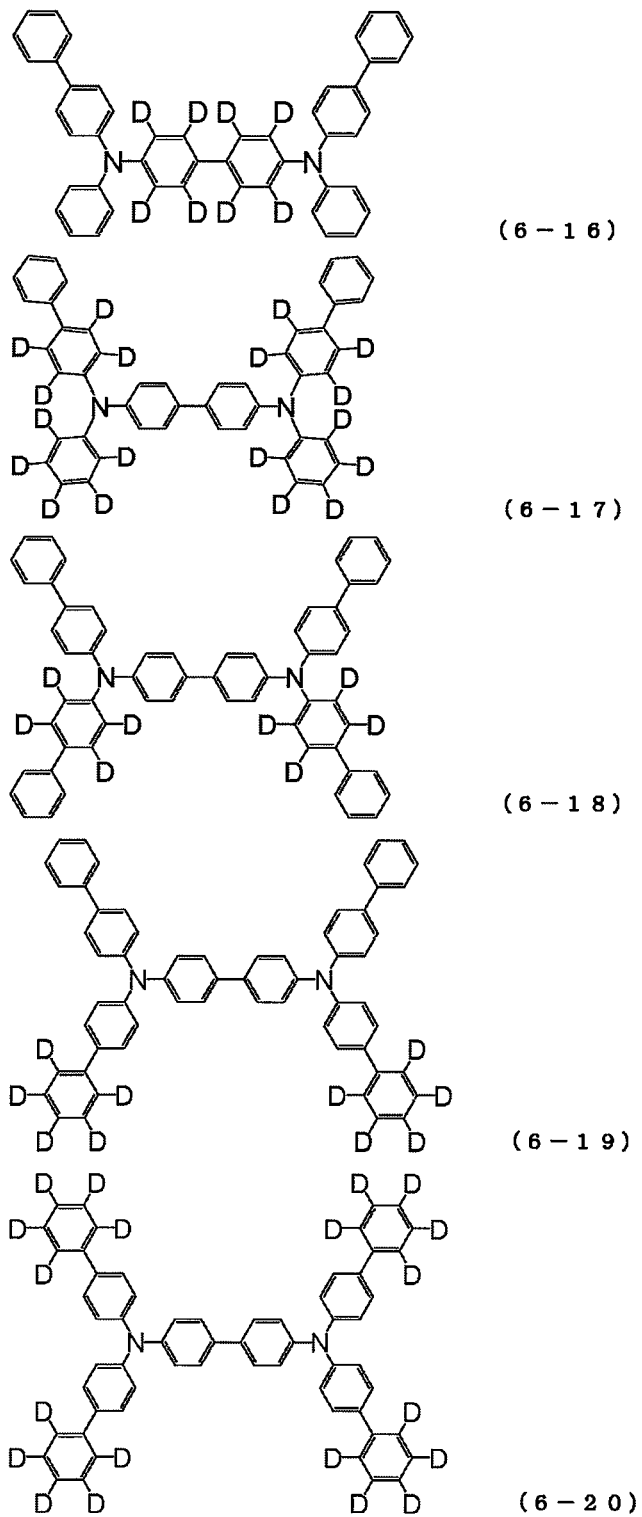
FIG. 58 is a view showing the structural formulas of Compounds (6-16) to (6-20) which are triarylamine compounds of the general formula (6).
Figure 59:
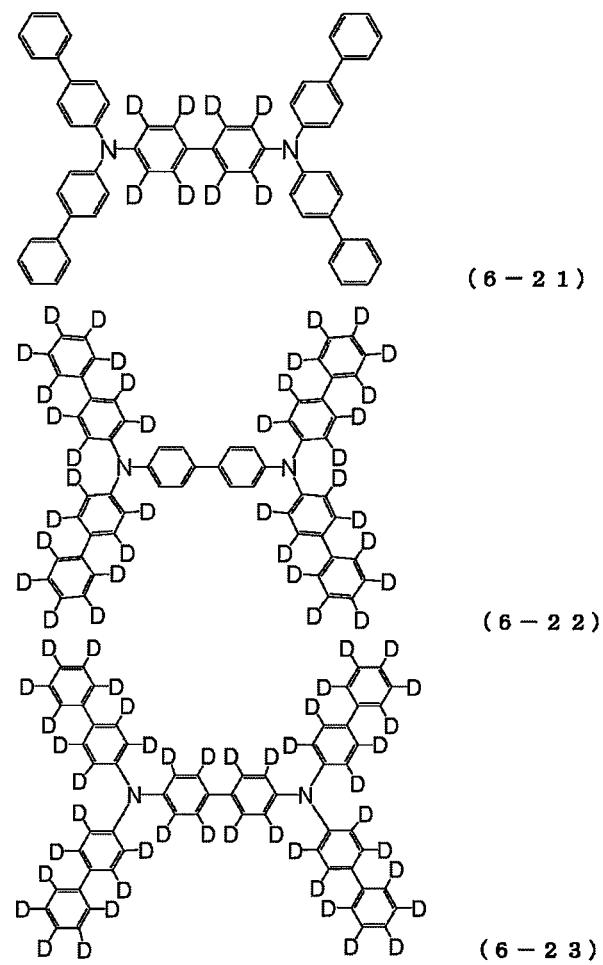
FIG. 59 is a view showing the structural formulas of Compounds (6-21) to (6-23) which are triarylamine compounds of the general formula (6).

If $r^{23}$, $r^{24}$, $r^{27}$ and $r^{28}$ are each an integer of 2 to 5, or if $r^{25}$ and $r^{26}$ are each an integer of 2 to 4, on the other hand, a plurality of the substituents $R^{23}$'s to the substituents $R^{28}$'s are bound to the same benzene ring. In this case, the plurality of the substituents present may be present independently of each other so as not to form a ring, but may be bonded to each other via a single bond, a substituted or unsubstituted methylene group, an oxygen atom, or a sulfur atom to form a ring. For example, the plurality of substituents may be bound together to form a naphthalene ring, as in the exemplary compounds 6-13 and 6-14 in FIG. 57.

($R^{23}$ to $R^{28}$)

In the general formula (6), $R^{23}$ to $R^{28}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxy group. The alkyl group having 1 to 6 carbon atoms, the alkenyl group having 2 to 6 carbon atoms, and the alkyloxy group having 1 to 6 carbon atoms may be straight-chain or branched.

The alkyl group having 1 to 6 carbon atoms, the cycloalkyl group having 5 to 10 carbon atoms, or the alkenyl group having 2 to 6 carbon atoms, represented by $R^{23}$ to $R^{28}$, can be exemplified by a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, a 2-butenyl group and the like.

The alkyl group having 1 to 6 carbon atoms, the cycloalkyl group having 5 to 10 carbon atoms, or the alkenyl group having 2 to 6 carbon atoms, represented by $R^{23}$ to $R^{28}$, may be unsubstituted, but may have a substituent. The substituent can be exemplified by the following groups, in addition to a deuterium atom, a cyano group, and a nitro group:

a halogen atom, for example, a fluorine atom, a chlorine atom, a bromine atom, an iodine atom or the like;

an alkyloxy group having 1 to 6 carbon atoms, for example, a methyloxy group, an ethyloxy group, a propyloxy group or the like;

an alkenyl group, for example, a vinyl group, an allyl group or the like;

an aryloxy group, for example, a phenyloxy group, a tolyloxy group or the like;

an arylalkyloxy group, for example, a benzyloxy group, a phenethyloxy group or the like;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group or the like; and an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a carbolinyl group or the like; The alkenyl group and the alkyloxy group having 1 to 6 carbon atoms may be straight-chain or branched. Any of the above exemplary substituents may be further substituted by the above exemplary substituent. The above exemplary substituents may be present independently of each other to avoid formation of a ring. However, they may be bonded to each other via a single bond, a substituted or unsubstituted methylene group, an oxygen atom, or a sulfur atom to form a ring.

The alkyloxy group having 1 to 6 carbon atoms or the cycloalkyloxy group having 5 to 10 carbon atoms, represented by $R^{23}$ to $R^{28}$, can be exemplified by a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, a 2-adamantyloxy group and the like.

The alkyloxy group having 1 to 6 carbon atoms or the cycloalkyloxy group having 5 to 10 carbon atoms, represented by $R^{23}$ to $R^{28}$, may be unsubstituted, but may have a substituent. Examples of the substituent are the same as those shown as the substituents that the alkyl group having 1 to 6 carbon atoms, the cycloalkyl group having 5 to 10 carbon atoms, or the alkenyl group having 2 to 6 carbon atoms, represented by $R^{23}$ to $R^{28}$ in the general formula (6), may have. The same holds true of the embodiments that the substituents can adopt.

The aromatic hydrocarbon group, the aromatic heterocyclic group, or the condensed polycyclic aromatic group, represented by $R^{23}$ to $R^{28}$, can be exemplified by the same ones as those shown in connection with the aromatic hydrocarbon group, the aromatic heterocyclic group, or the condensed polycyclic aromatic group represented by $Ar^1$ to $Ar^4$ in the aforementioned general formula (1). These groups may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

The aryloxy group represented by $R^{23}$ to $R^{28}$ can be exemplified by a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, a perylenyloxy group and the like.

The aryloxy group represented by $R^{23}$ to $R^{28}$ may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

As $R^{23}$ to $R^{28}$, a deuterium atom, an alkyl group having 1 to 6 carbon atoms, an alkenyl group having 2 to 6 carbon atoms, an aromatic hydrocarbon group, or a condensed polycyclic aromatic group is preferred; and a deuterium atom, a phenyl group, a biphenylyl group, a naphthyl group, or a vinyl group is more preferred. It is also preferred for $R^{23}$ to $R^{28}$ to bind to each other via a single bond, thereby forming a condensed aromatic ring. Particularly, a deuterium atom, a phenyl group, or a biphenylyl group is preferred.

($L^1$)

In the general formula (6), $L^1$ is a bridging group connecting the two triarylamine structures, and represents a single bond, or a divalent group represented by each of the following structural formulas (B) to (G):

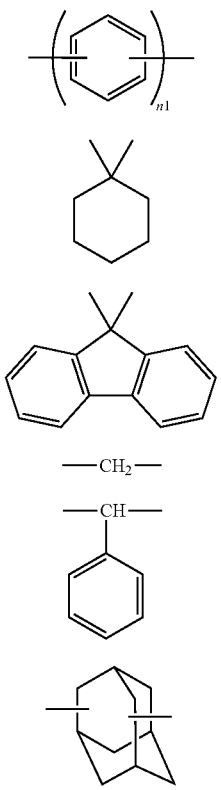

(B), (C), (D), (E), (F), (G)

where n1 denotes an integer of 1 to 4.

As $L^1$, the divalent group represented by the structural formula (B), (D) or (G), or a single bond, is preferred; and the divalent group represented by the structural formula (D) or (G), or a single bond, is more preferred. In the structural formula (B), n1 is preferably 1 or 2.

Triarylamine compound of the general formula (7);

bound to the respective benzene rings, $r^{29}$, $r^{30}$, $r^{33}$, $r^{36}$, $r^{39}$ and $r^{40}$ each denote an integer of 0 to 5, and $r^{31}$, $r^{32}$, $r^{34}$, $r^{35}$, $r^{37}$ and $r^{38}$ each denote an integer of 0 to 4. As $r^{29}$ to $r^{40}$, an integer of 0 to 3 is preferred, and an integer of 0 to 2 is more preferred.

If $r^{29}$ to $r^{40}$ are each 0, this means that there are none of $R^{29}$ to $R^{40}$ on the benzene rings. That is, the benzene rings are not substituted by groups represented by $R^{29}$ to $R^{40}$.

Figure 62:
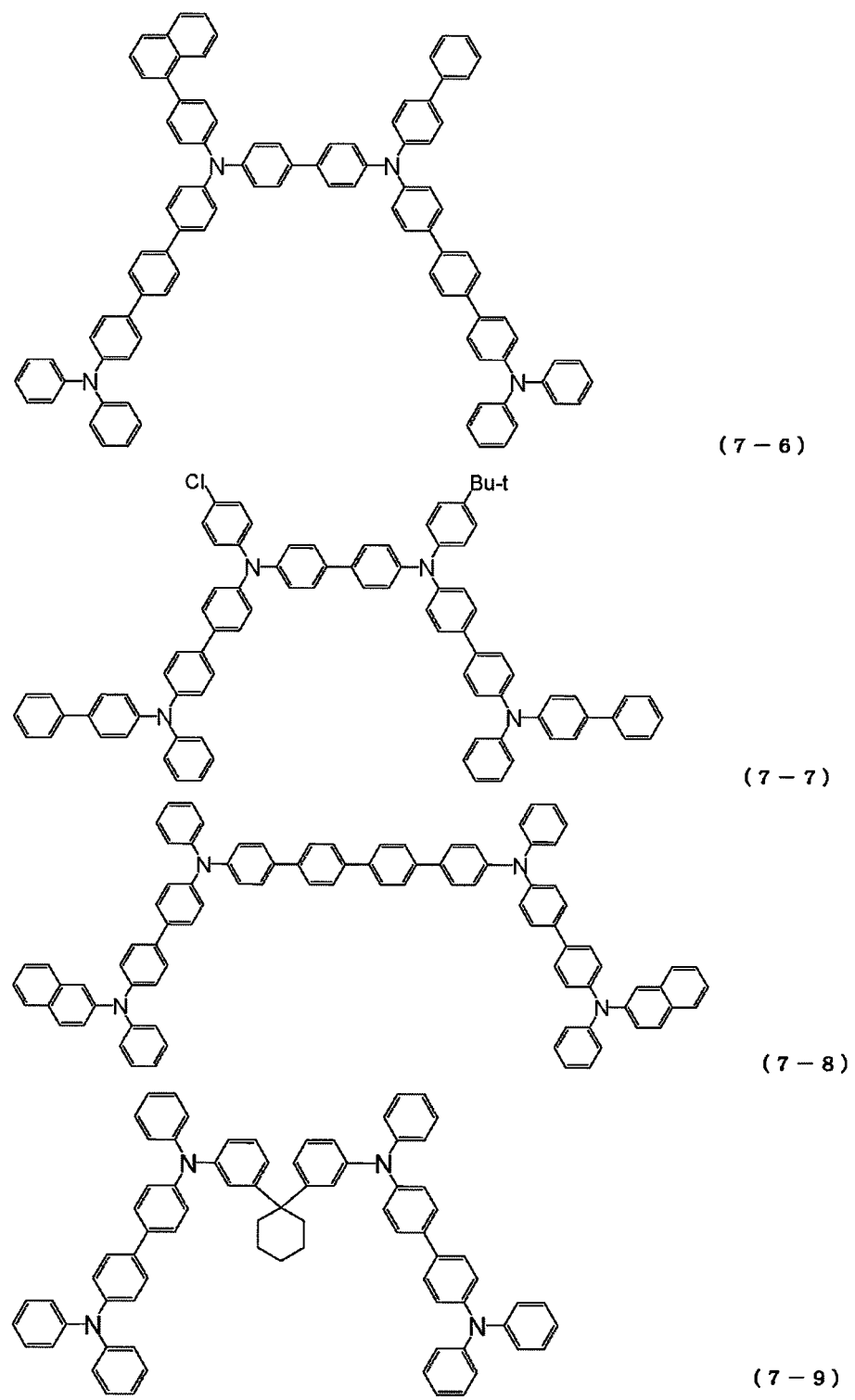
FIG. 62 is a view showing the structural formulas of Compounds (7-6) to (7-9) which are triarylamine compounds of the general formula (7).
Figure 63:
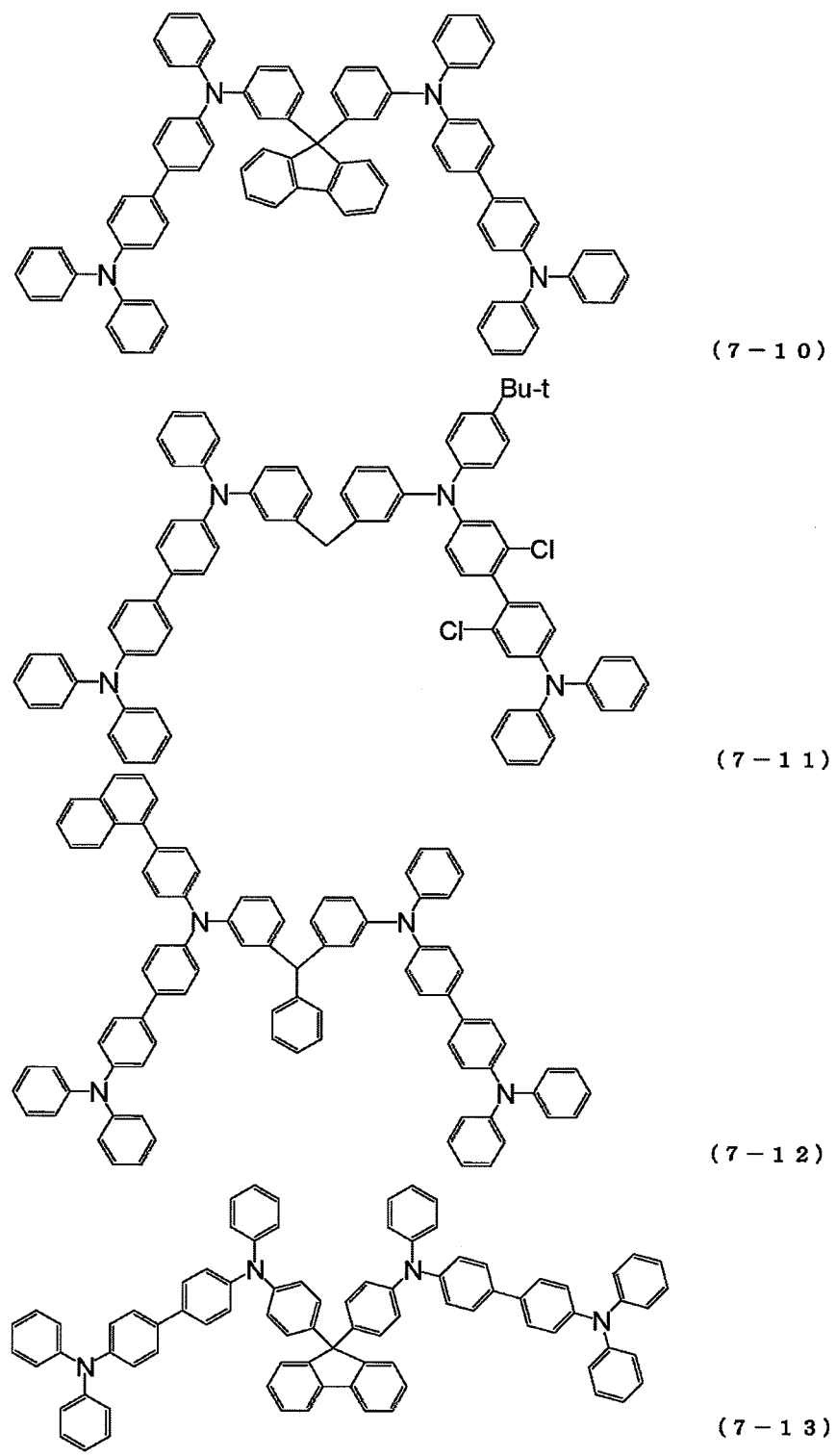
FIG. 63 is a view showing the structural formulas of Compounds (7-10) to (7-13) which are triarylamine compounds of the general formula (7).

If $r^{29}$, $r^{30}$, $r^{33}$, $r^{36}$, $r^{39}$ and $r^{40}$ are each an integer of 2 to 5, or if $r^{31}$, $r^{32}$, $r^{34}$, $r^{35}$, $r^{37}$ and $r^{38}$ are each an integer of 2 to 4, on the other hand, a plurality of the groups $R^{29}$'s to the groups $R^{40}$'s, respectively, are bound to the same benzene ring. In this case, a plurality of the substituents present may be present independently of each other so as not to form a ring, but may be bonded to each other via a single bond, a substituted or unsubstituted methylene group, an oxygen atom, or a sulfur atom to form a ring. For example, the plurality of the substituents may be bound together to form a naphthalene ring, as in the exemplary compound 7-8 in FIG. 62.

($R^{29}$ to $R^{40}$)

In the general formula (7), $R^{29}$ to $R^{40}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxy group. The alkyl group having 1 to 6 carbon atoms, the alkenyl group having 2 to 6 carbon atoms, and the alkyloxy group having 1 to 6 carbon atoms may be straight-chain or branched.

The alkyl group having 1 to 6 carbon atoms, the cycloalkyl group having 5 to 10 carbon atoms, or the alkenyl group having 2 to 6 carbon atoms, represented by $R^{29}$ to $R^{40}$, can be exemplified by the same ones as those shown in connection with the alkyl group having 1 to 6 carbon atoms, the cycloalkyl group having 5 to 10 carbon atoms, or the

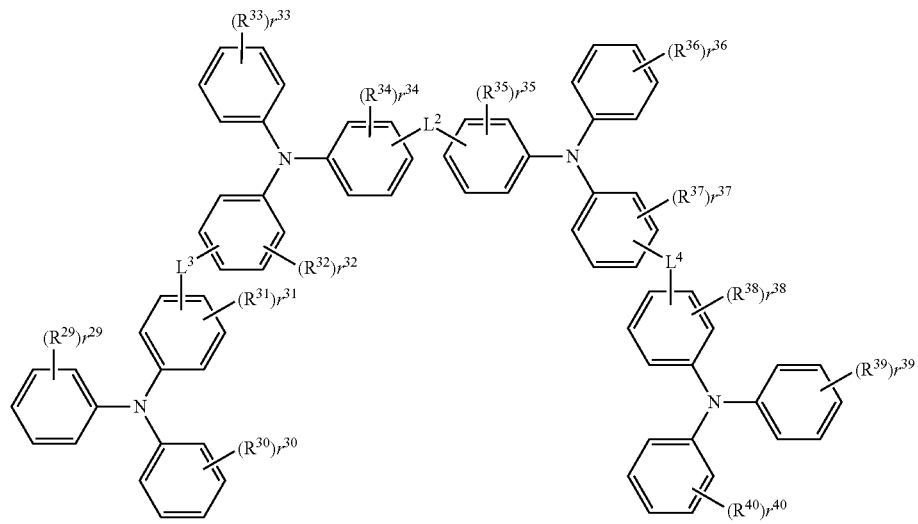

(7)

($r^{29}$ to $r^{40}$)

In the general formula (7), $r^{29}$ to $r^{40}$ are each an integer showing the number of the groups $R^{29}$'s to the groups $R^{40}$'s alkenyl group having 2 to 6 carbon atoms, represented by $R^{23}$ to $R^{28}$ in the general formula (6). These groups may be unsubstituted, but may have a substituent. The substituent can be exemplified by the same ones as those shown as the substituents optionally possessed by the alkyl group having 1 to 6 carbon atoms, the cycloalkyl group having 5 to 10 carbon atoms, or the alkenyl group having 2 to 6 carbon atoms, represented by $R^{23}$ to $R^{28}$ in the general formula (6). The same holds true of the embodiments that the substituents can adopt.

The alkyloxy group having 1 to 6 carbon atoms or the cycloalkyloxy group having 5 to 10 carbon atoms, represented by $R^{29}$ to $R^{40}$, can be exemplified by the same ones as those shown in connection with the alkyloxy group having 1 to 6 carbon atoms, or the cycloalkyloxy group having 5 to 10 carbon atoms, represented by $R^{23}$ to $R^{28}$ in the general formula (6). These groups may be unsubstituted, but may have a substituent. The substituent can be exemplified by the same ones as those shown in connection with the substituents for the alkyl group having 1 to 6 carbon atoms, the cycloalkyl group having 5 to 10 carbon atoms, or the alkenyl group having 2 to 6 carbon atoms, represented by $R^{23}$ to $R^{28}$ in the general formula (6). The same holds true of the embodiments that the substituents can adopt.

The aromatic hydrocarbon group, aromatic heterocyclic group, or condensed polycyclic aromatic group, represented by $R^{29}$ to $R^{40}$, can be exemplified by the same ones as those shown in connection with the aromatic hydrocarbon group, the aromatic heterocyclic group, or the condensed polycyclic aromatic group represented by $Ar^1$ to $Ar^4$ in the general formula (1). These groups may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

The aryloxy group represented by $R^{29}$ to $R^{40}$ can be exemplified by the same ones as those shown in connection with the aryloxy group represented by $R^{23}$ to $R^{28}$ in the general formula (6). The aryloxy group represented by $R^{29}$ to $R^{40}$ may be unsubstituted, but may have a substituent. The substituent can be exemplified by the same ones as those shown as the substituents that the aromatic hydrocarbon group, the aromatic heterocyclic group, or the condensed polycyclic aromatic group represented by $Ar^1$ to $Ar^4$ in the general formula (1) may have. The same holds true of the embodiments that the substituents can adopt.

As $R^{29}$ to $R^{40}$, a deuterium atom, an alkyl group having 1 to 6 carbon atoms, an alkenyl group having 2 to 6 carbon atoms, an aromatic hydrocarbon group, or a condensed polycyclic aromatic group is preferred; and a deuterium atom, a phenyl group, a biphenylyl group, a naphthyl group, or a vinyl group is more preferred. $R^{29}$ to $R^{40}$ may be present independently of each other to avoid the formation of a ring. However, it is preferred for $R^{29}$ to $R^{40}$ to bind to each other via a single bond, thereby forming a condensed aromatic ring. Particularly, a deuterium atom, a phenyl group, or a biphenylyl group is preferred.

($L^2$ to $L^4$)

Figure 64:
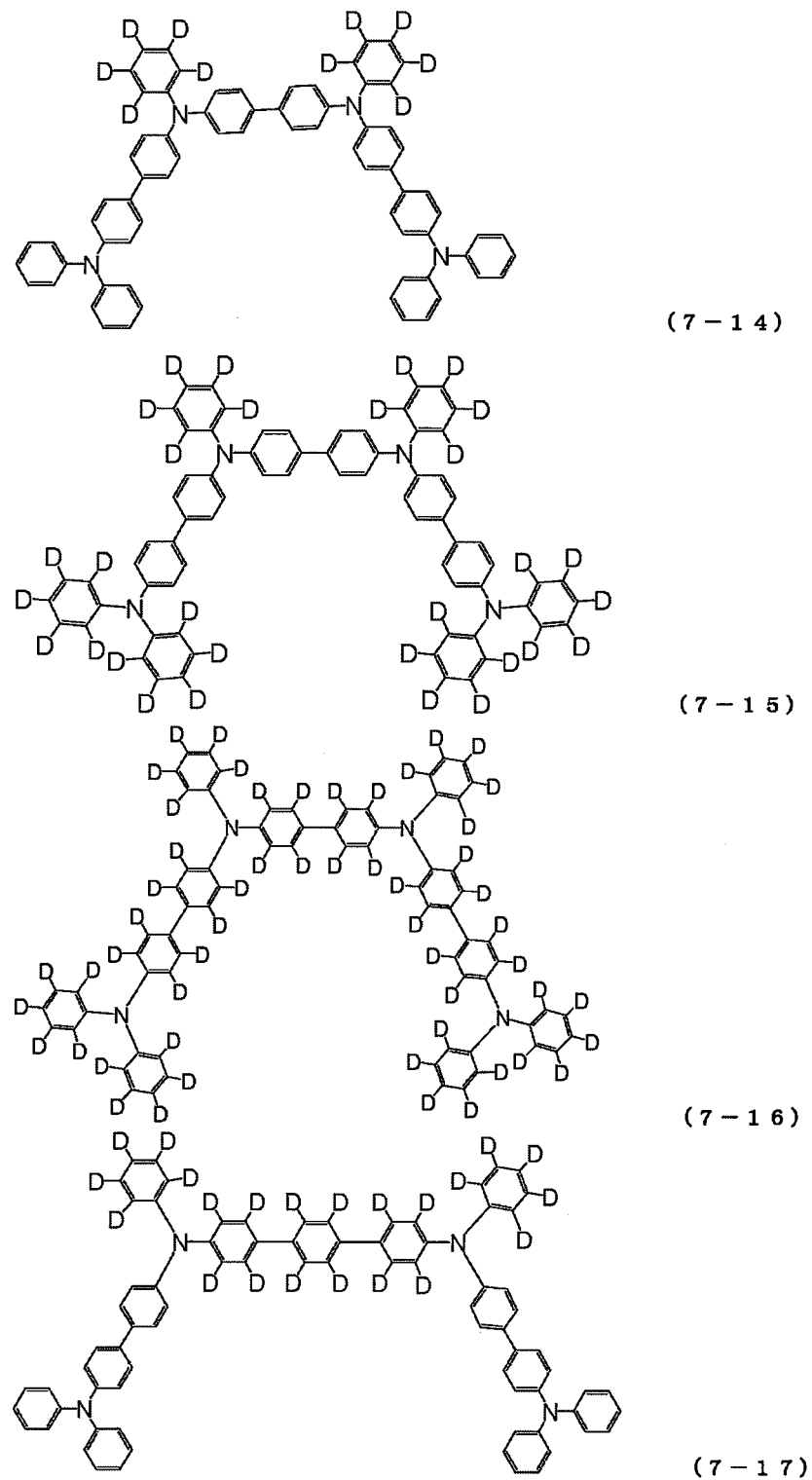
FIG. 64 is a view showing the structural formulas of Compounds (7-14) to (7-17) which are triarylamine compounds of the general formula (7).

In the general formula (7), $L^2$ to $L^4$ are each a bridging group connecting the two triarylamine skeletons, and each represent a single bond, or a divalent group represented by the following structural formula (B') or each of the aforementioned structural formulas (C) to (G). The divalent group represented by the following structural formula (B') may be unsubstituted, or may be substituted by deuterium, as in the exemplary compound 7-17 in FIG. 64.

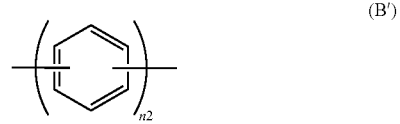

where n2 denotes an integer of 1 to 3.

As $L^2$ to $L^4$, the divalent group represented by the structural formula (B') or (D), or a single bond, is preferred; and the divalent group represented by the structural formula (B'), or a single bond, is more preferred. In the structural formula (B'), n2 is preferably 1 or 2, and more preferably 1.

Figure 60:
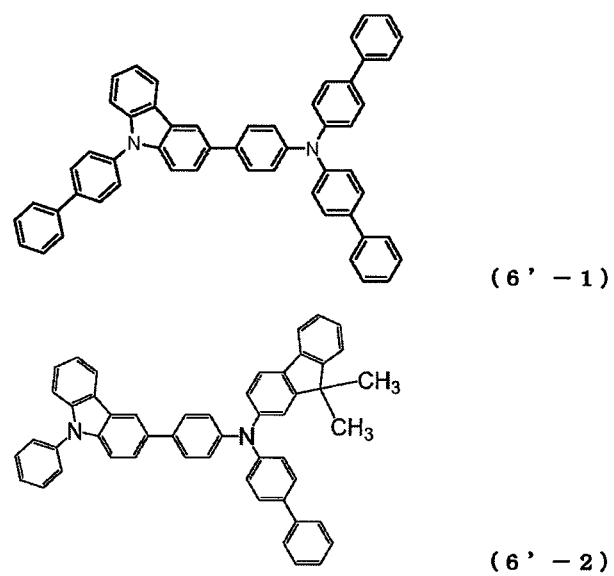
FIG. 60 is a view showing the structural formulas of Compounds (6'-1) and (6'-2), other than triarylamine compounds of the general formula (6), among triarylamine compounds having two triarylamine structures.
Figure 61:
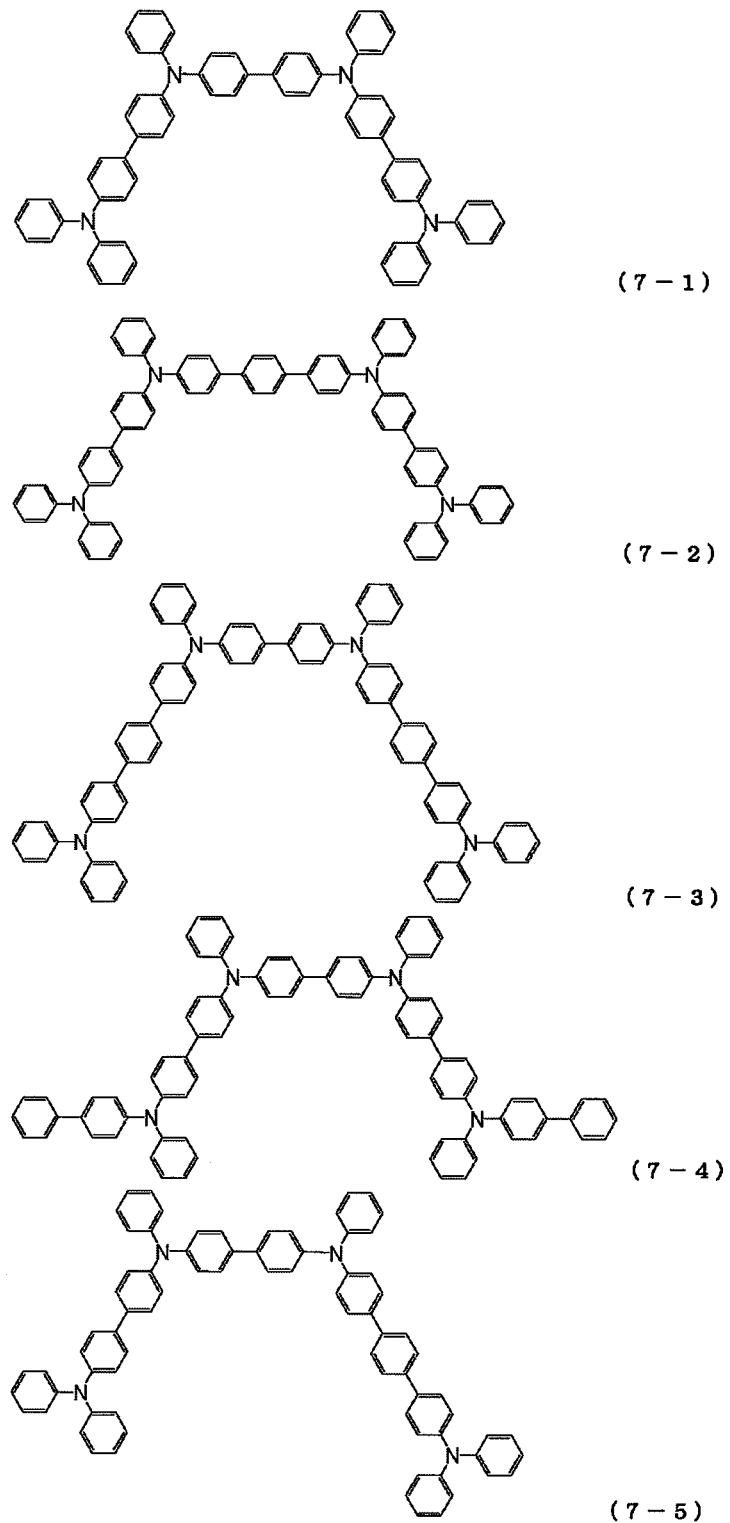
FIG. 61 is a view showing the structural formulas of Compounds (7-1) to (7-5) which are triarylamine compounds of the general formula (7).

Concrete examples of the preferred compounds among the triarylamine compounds of the general formula (6) are shown in FIGS. 55 to 59, but the triarylamine compounds of the general formula (6) are not limited to these exemplary compounds. In connection with the triarylamine compounds having two triarylamine structures among the aforementioned triarylamine compounds having two to six triarylamine structures, preferred examples of the compounds other than the triarylamine compounds of the general formula (6) are shown in FIG. 60. However, the triarylamine compounds having two triarylamine structures are not limited to these exemplary compounds. D in the structural formulas represents deuterium.

Concrete examples of the preferred compounds among the arylamine compounds of the general formula (7) are shown in FIGS. 61 to 64, but the triarylamine compounds of the general formula (7) are not limited to these exemplary compounds. D in the structural formulas represents deuterium.

The triarylamine compounds having 2 to 6 triarylamine structures, such as the triarylamine compounds of the general formula (6) or the triarylamine compounds of the general formula (7), can be synthesized in accordance with publicly known methods (see Patent Documents 1, 8 to 9).

Examples

The embodiments of the present invention will now be described specifically by the following Examples, which in no way limit the present invention.

Synthesis Example 1: Compound 1-5

Synthesis of 4-{(biphenyl-4-yl)-phenylamino}-4"-{(9,9-dimethyl-9H-fluoren-2-yl)-phenylamino}-1,1':3',1"-terphenyl:

| | |
|---|---|
| A nitrogen-purged reaction vessel was charged with N-(biphenyl-4-yl)-N-(4-bromophenyl)aniline | 8.0 g, |
| N-(9,9-dimethyl-9H-fluoren-2-yl)-N-{3'-(4,4,5,5-tetramethyl-[1,3,2]dioxaboran-2-yl)biphenyl-4-yl}aniline | 11.4 g, |
| potassium carbonate | 7.5 g, |
| water | 64 ml, |
| toluene | 64 ml, |
| ethanol and | 16 ml, |
| tetrakis(triphenylphosphine)palladium | 0.8 g. |

The charge was heated, and stirred for 16 hours at 70° C. to prepare a mixture. The mixture was cooled to room temperature, and ethyl acetate and water were added, whereafter an organic layer was collected by liquid separation. The organic layer was concentrated, and then subjected to recrystallization using a THF/acetone mixed solvent. As a result, 9.54 g (yield 69%) of 4-{(biphenyl-4-yl)-phenylamino}-4"-{(9,9-dimethyl-9H-fluoren-2-yl)-phenylamino}-1,1':3',1"-terphenyl (Compound 1-5) was obtained as a white powder.

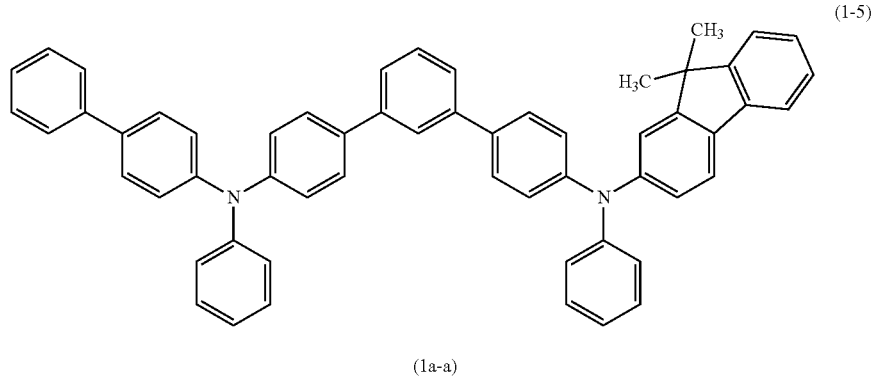 [SMILES: CC1(C)c2ccccc2-c2ccc(N(c3ccccc3)c3ccc(-c4cccc(-c5ccc(N(c6ccccc6)c6ccc(-c7ccccc7)cc6)cc5)c4)cc3)cc21]

(1-5)

(1a-a)

In connection with the resulting white powder, its structure was identified using NMR. In $^1$H-NMR (THF-$d_8$), the following signals of 44 hydrogens were detected:

$$\delta\ (ppm) = 7.86\ (1H)$$
$$7.68 - 6.97\ (37H)$$
$$1.41\ (6H)$$

Synthesis Example 2: Compound 1-6

Synthesis of 4-{(9,9-dimethyl-9H-fluoren-2-yl)-phenylamino}-4"-{(naphthalen-1-yl)-phenylamino}-1,1':3',1"-terphenyl:

Reactions were performed under the same conditions as in Synthesis Example 1, except that
N-(3'-bromobiphenyl-4-yl)-N-(naphthalen-1-yl)aniline was used instead of
N-(biphenyl-4-yl)-N-(4-bromophenyl)aniline,
and
4-{N-(9,9-dimethyl-9H-fluoren-2-yl)-phenylamino}-phenylboronic acid
was used instead of
N-(9,9-dimethyl-9H-fluoren-2-yl)-N-{3'-(4,4,5,5-tetramethyl-[1,3,2]dioxaboran-2-yl)biphenyl-4-yl}aniline.
As a result, 7.88 g (yield 62%) of 4-{(9,9-dimethyl-9H-fluoren-2-yl)-phenylamino}-4"-{(naphthalen-1-yl)-phenylamino}-1,1':3',1"-terphenyl (Compound 1-6) was obtained as a light yellowish white powder.

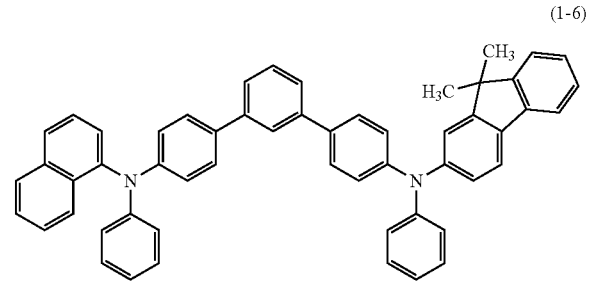

(1-6)

(1a-a)

In connection with the resulting light yellowish white powder, its structure was identified using NMR. In $^1$H-NMR (CDCl$_3$), the following signals of 42 hydrogens were detected:

$$\delta\ (ppm) = 7.98\ (1H)$$
$$7.92\ (1H)$$
$$7.84 - 7.75\ (2H)$$
$$7.70 - 6.94\ (32H)$$
$$1.49\ (6H)$$

Synthesis Example 3: Compound 1-21

Synthesis of 3,3"-bis{(biphenyl-4-yl)-phenylamino}-1,1':4',1"-terphenyl:

| | |
|---|---|
| A nitrogen-purged reaction vessel was charged with 1,4-dibromobenzene | 6.20 g, |
| N-(biphenyl-4-yl)-N-{3-(4,4,5,5-tetramethyl-[1,3,2]dioxaboran-2-yl)phenyl}aniline | 25.1 g, |
| potassium carbonate | 10.8 g, |
| water | 39 ml, |
| toluene | 380 ml, |
| and | |
| ethanol | 95 ml. |

With the charge being ultrasonically irradiated for 30 minutes, a nitrogen gas was passed therethrough to prepare a mixture. To the mixture, tetrakis(triphenylphosphine)palladium (0.95 g) was added, and the system was heated and refluxed for 18 hours with stirring. Then, the mixture was cooled to room temperature, 200 ml of water and 190 ml of heptane were added, whereafter the resulting precipitate was collected by filtration. The precipitate was dissolved with heating in 1,200 ml of 1,2-dichlorobenzene, and the solution was subjected to adsorption purification using 39 g of silica gel, and then to adsorption purification using 19 g of activated clay. Then, 725 ml of methanol was added, and a crude product precipitated was collected by filtration. For the crude product, crystallization using a 1,2-dichlorobenzine/methanol mixed solvent was repeated, and then reflux washing using 300 ml of methanol was performed. As a result, 15.22 g (yield 81%) of 3,3"-bis{(biphenyl-4-yl)-phenylamino}-1,1':4',1"-terphenyl (Compound 1-21) was obtained as a white powder.

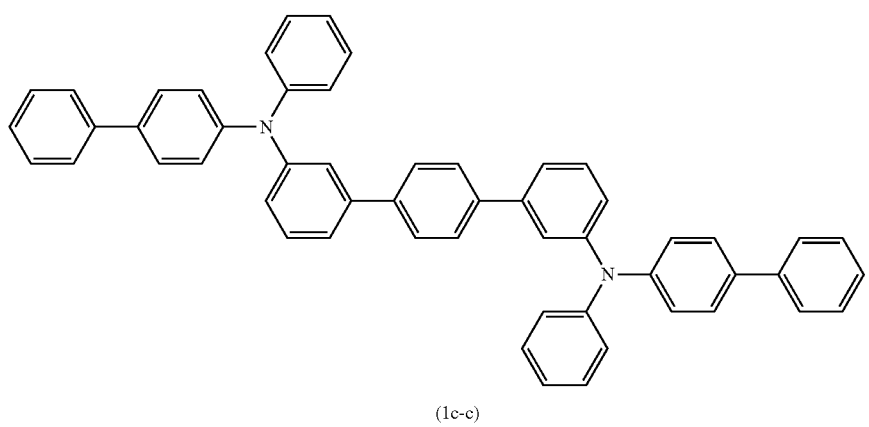

(1-21)

In connection with the resulting white powder, its structure was identified using NMR. In $^1$H-NMR (CDCl$_3$), the following signals of 40 hydrogens were detected:

$\delta$ (ppm) = 7.61 (2H)

7.56 – 6.83 (38H)

Synthesis Example 4: Compound 1-22

Synthesis of 2,2"-bis{(biphenyl-4-yl)-phenylamino}-1,1': 4',1"-terphenyl:

Reactions were performed under the same conditions as in Synthesis Example 3, except that
N-(biphenyl-4-yl)-N-{2-(4,4,5,5-tetramethyl-[1,3,2]dioxaboran-2-yl)phenyl}aniline
was used instead of
N-(biphenyl-4-yl)-N-{3-(4,4,5,5-tetramethyl-[1,3,2]dioxaboran-2-yl)phenyl}aniline.
As a result, 11.11 g (yield 58%) of 2,2"-bis{(biphenyl-4-yl)-phenylamino}-1,1':4',1"-terphenyl (Compound 1-22) was obtained as a white powder.

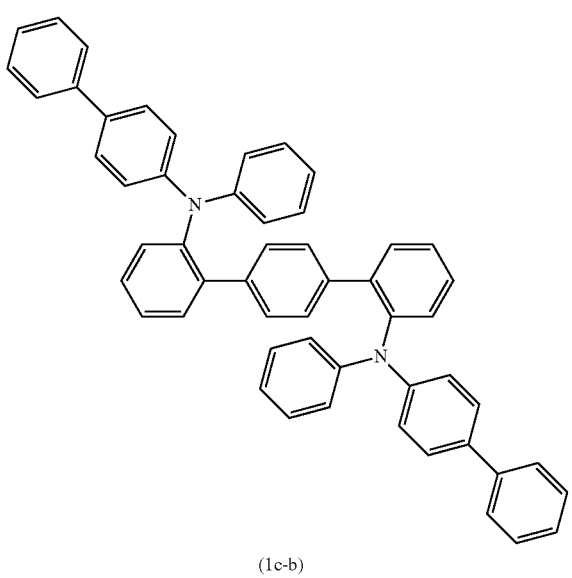

(1-22)

(1c-b)

In connection with the resulting white powder, its structure was identified using NMR. In $^1$H-NMR (THF-d$_8$), the following signals of 40 hydrogens were detected:

$\delta$ (ppm) = 7.52 (4H)

7.40 – 7.20 (18H)

7.03 (8H)

6.90 – 6.75 (10H)

Synthesis Example 5: Compound 1-32

Synthesis of 4-{(biphenyl-4-yl)-phenylamino}-2"-{(9,9-dimethyl-9H-fluoren-2-yl)-phenylamino}-1,1':4',1"-terphenyl:

| A nitrogen-purged reaction vessel was charged with | 10.0 g, |
| --- | --- |
| N-(biphenyl-4-yl)-N-(2"-bromo-1,1':4',1"-terphenyl-4-yl)aniline | |
| 2-(phenylamino)-9,9-dimethyl-9H-fluorene | 6.2 g, |
| palladium acetate | 0.081 g, |
| t-butoxysodium | 3.5 g, |
| a 50% (w/v) toluene solution of tri-t-butylphosphine | 0.146 g, |
| and | |
| toluene | 100 ml. |

The charge was heated, and stirred overnight at 100° C. to prepare a mixture. Insolubles were removed from the mixture by filtration, and the filtrate was concentrated. Then, the concentrate was purified using a column chromatograph (carrier: silica gel, eluent: heptane/dichloromethane). As a result, 4.77 g (yield 35%) of 4-{(biphenyl-4-yl)-phenylamino}-2"-{(9,9-dimethyl-9H-fluoren-2-yl)-phenylamino}-1,1':4',1"-terphenyl (Compound 1-32) was obtained as a white powder.

δ (ppm) = 7.61 – 7.48 (4H)

7.42 – 6.92 (32H)

6.81 (1H)

6.76 (1H)

1.28 (6H)

Synthesis Example 6: Compound 1-34

Synthesis of 4,4''-bis{(9,9-dimethyl-9H-fluoren-2-yl)-phenylamino}-1,1':3',1''-terphenyl:

| | |
|---|---|
| A nitrogen-purged reaction vessel was charged with | 8.81 g, |
| 4,4''-dibromo-1,1':3',1''-terphenyl | |
| 2-(phenylamino)-9,9-dimethyl-9H-fluorene | 13.6 g, |
| t-butoxysodium | 5.12 g, |

| | |
|---|---|
| tris(dibenzylideneacetone)dipalladium | 0.33 g, |
| and | |
| a 50% (w/v) toluene solution of tri-t-butylphosphine | 0.63 ml. |

The charge was heated and refluxed for 2 hours with stirring to prepare a mixture. The mixture was gradually cooled, then methanol was added, and the resulting precipitate was collected by filtration. The precipitate was dissolved with heating in chlorobenzene, and the solution was subjected to adsorption purification using silica gel. Then, adsorption purification using activated clay was performed, whereafter crystallization using a chlorobenzene/methanol mixed solvent was carried out. Then, reflux washing using methanol was performed. As a result, 16.25 g (yield 90%) of 4,4''-bis{(9,9-dimethyl-9H-fluoren-2-yl)-phenylamino}-1,1':3', 1''-terphenyl (Compound 1-34) was obtained as a white powder.

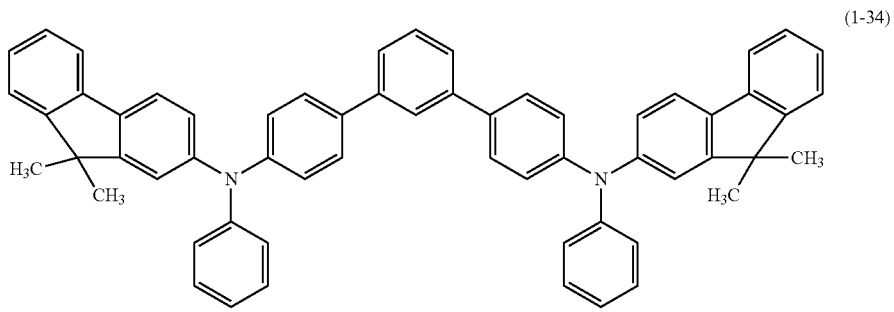

(1-34)

(1a-a)

In connection with the resulting white powder, its structure was identified using NMR. In $^1$H-NMR (CDCl$_3$), the following signals of 48 hydrogens were detected:

δ (ppm) = 7.84 (1H)

7.70 – 7.03 (35H)

1.48 (12H)

Synthesis Example 7: Compound 1-37

Synthesis of 2-{(biphenyl-4-yl)-phenylamino}-4''-{(9,9-dimethyl-9H-fluoren-2-yl)-phenylamino}-1,1':4',1''-terphenyl:

Reactions were performed under the same conditions as in Synthesis Example 5, except that N-(9,9-dimethyl-9H-fluoren-2-yl)-N-(2''-bromo-1,1':4',1''-terphenyl-4-yl)aniline was used instead of N-(biphenyl-4-yl)-N-(2''-bromo-1,1':4',1''-terphenyl-4-yl)aniline, and N-(biphenyl-4-yl)aniline was used instead of 2-(phenylamino)-9,9-dimethyl-9H-fluorene.

As a result, 11.7 g (yield 73%) of 2-{(biphenyl-4-yl)-phenylamino}-4''-{(9,9-dimethyl-9H-fluoren-2-yl)-phenylamino}-1,1':4',1''-terphenyl (Compound 1-37) was obtained as a white powder.

(1-37)

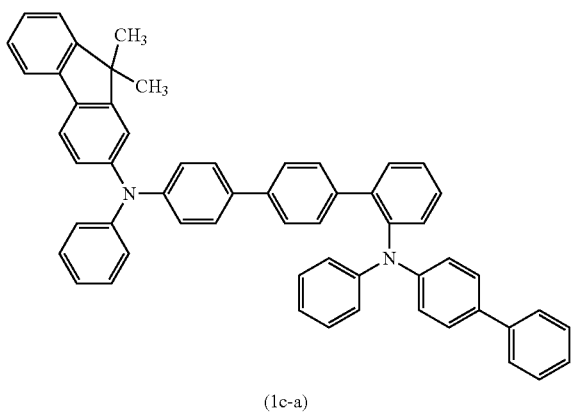

(1c-a)

In connection with the resulting white powder, its structure was identified using NMR. In $^1$H-NMR (CDCl$_3$), the following signals of 44 hydrogens were detected:

$\delta$ (ppm) = 7.68 (1H)

7.64 – 6.84 (37H)

1.48 (6H)

Synthesis Example 8: Compound 1-38

Synthesis of 4,4"-bis{(9,9-dimethyl-9H-fluoren-2-yl)-phenylamino}-1,1':2',1"-terphenyl:
Reactions were performed under the same conditions as in Synthesis Example 3, except that
1,2-diiodobenzene
was used instead of
1,4-dibromobenzene
and
4-{(9,9-dimethyl-9H-fluoren-2-yl)-phenylamino}-phenylboronic acid
was used instead of
N-(biphenyl-4-yl)-N-{3-(4,4,5,5-tetramethyl-[1,3,2]dioxaboran-2-yl)phenyl}aniline.
As a result, 6.6 g (yield 39%) of 4,4"-bis{(9,9-dimethyl-9H-fluoren-2-yl)-phenylamino}-1,1':2',1"-terphenyl (Compound 1-38) was obtained as a white powder.

(1-38)

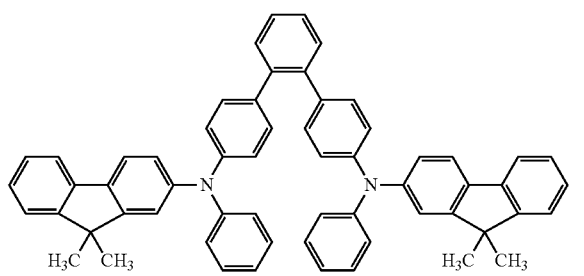

(1b-a)

In connection with the resulting white powder, its structure was identified using NMR. In $^1$H-NMR (CDCl$_3$), the following signals of 48 hydrogens were detected:

$\delta$ (ppm) = 7.64 (2H)

7.58 (2H)

7.45 – 6.99 (32H)

1.38 (12H)

Synthesis Example 9: Compound 1-39

Synthesis of 4,4"-bis{bis(biphenyl-4-yl)amino}-1,1':2',1"-terphenyl:
Reactions were performed under the same conditions as in Synthesis Example 3, except that
1,2-diiodobenzene
was used instead of
1,4-dibromobenzene
and
4-{bis(biphenyl-4-yl)amino}-phenylboronic acid
was used instead of
N-(biphenyl-4-yl)-N-{3-(4,4,5,5-tetramethyl-[1,3,2]dioxaboran-2-yl)phenyl}aniline.
As a result, 4.6 g (yield 24%) of 4,4"-bis{bis(biphenyl-4-yl)amino}-1,1':2',1"-terphenyl (Compound 1-39) was obtained as a white powder.

(1-39)

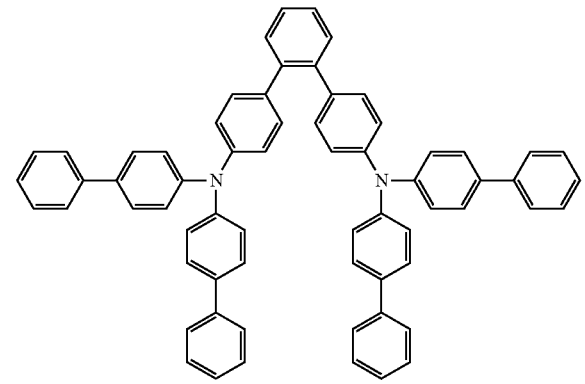

(1b-a)

In connection with the resulting white powder, its structure was identified using NMR. In $^1$H-NMR (CDCl$_3$), the following signals of 48 hydrogens were detected:

$\delta$ (ppm) = 7.57 – 7.28 (32H)

7.21 (8H)

7.11 (8H)

Synthesis Example 10: Compound 1-41

Synthesis of 4,4"-bis{(biphenyl-4-yl)-(naphthalen-1-yl)amino}-1,1':2',1"-terphenyl:

Reactions were performed under the same conditions as in Synthesis Example 6, except that
4,4"-dibromo-1,1':2',1"-terphenyl
was used instead of
4,4"-dibromo-1,1':3',1"-terphenyl
and
(biphenyl-4-yl)-(naphthalen-1-yl)amine
was used instead of
2-(phenylamino)-9,9-dimethyl-9H-fluorene.
As a result, 5.0 g (yield 30%) of 4,4"-bis{(biphenyl-4-yl)-(naphthalen-1-yl)amino}-1,1':2',1"-terphenyl (Compound 1-41) was obtained as a white powder.

(1-41)

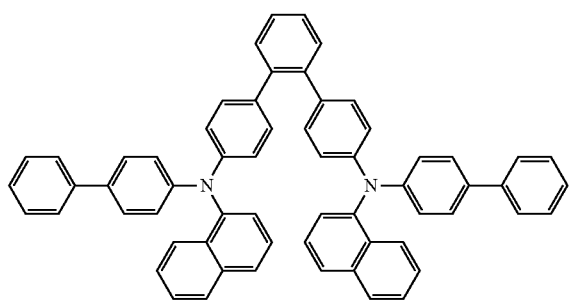

(1b-a)

In connection with the resulting white powder, its structure was identified using NMR. In $^1$H-NMR (CDCl$_3$), the following signals of 44 hydrogens were detected:

$\delta$ (ppm) = 7.93 – 7.84 (4H)

7.79 (2H)

7.60 – 7.26 (24H)

7.25 – 6.92 (14H)

Synthesis Example 11: Compound 1-42

Synthesis of 4,4"-bis[{4-(naphthalen-1-yl)phenyl}-phenylamino]-1,1':2',1"-terphenyl:

Reactions were performed under the same conditions as in Synthesis Example 6, except that
4,4"-dibromo-1,1':2',1"-terphenyl
was used instead of
4,4"-dibromo-1,1':3',1"-terphenyl
and
N-{4-(naphthalen-1-yl)phenyl}aniline
was used instead of
2-(phenylamino)-9,9-dimethyl-9H-fluorene.
As a result, 7.3 g (yield 43%) of 4,4"-bis[{4-(naphthalen-1-yl)phenyl}-phenylamino]-1,1':2',1"-terphenyl (Compound 1-42) was obtained as a white powder.

(1-42)

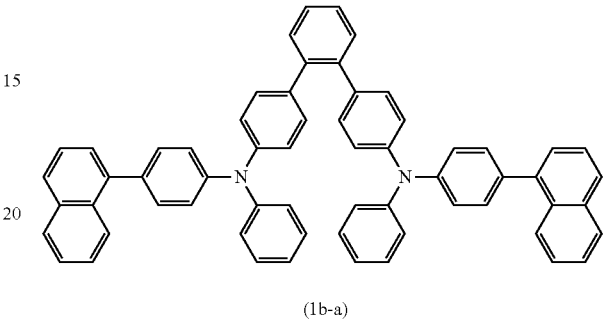

(1b-a)

In connection with the resulting white powder, its structure was identified using NMR. In $^1$H-NMR (CDCl$_3$), the following signals of 44 hydrogens were detected:

$\delta$ (ppm) = 8.01 (2H)

7.91 (2H)

7.84 (2H)

7.53 – 6.98 (38H)

Synthesis Example 12: Compound 1-45

Synthesis of 4,4"-bis[{4-(naphthalen-1-yl)phenyl}-phenylamino]-1,1':3',1"-terphenyl:

Reactions were performed under the same conditions as in Synthesis Example 6, except that
N-{4-(naphthalen-1-yl)phenyl}aniline
was used instead of
2-(phenylamino)-9,9-dimethyl-9H-fluorene.
As a result, 16.7 g (yield 79%) of 4,4"-bis[{4-(naphthalen-1-yl)phenyl}-phenylamino]-1,1':3',1"-terphenyl (Compound 1-45) was obtained as a white powder.

(1-45)

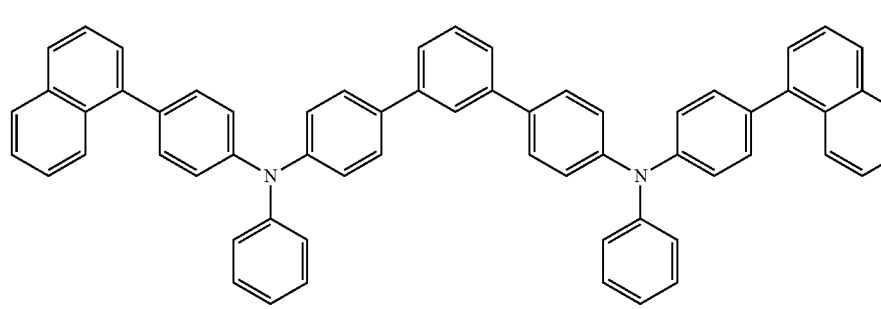

(1a-a)

In connection with the resulting white powder, its structure was identified using NMR. In $^1$H-NMR (CDCl$_3$), the following signals of 44 hydrogens were detected:

$\delta$ (ppm) = 8.08 (2H)

7.94 (2H)

7.90 – 7.80 (3H)

7.65 – 7.00 (37H)

Synthesis Example 13: Compound 1-47

Synthesis of 2,2"-bis{(9,9-dimethyl-9H-fluoren-2-yl)-phenylamino}-1,1':3',1"-terphenyl:
Reactions were performed under the same conditions as in Synthesis Example 3, except that
1,3-diiodobenzene
was used instead of
1,4-dibromobenzene,
and
2-{(9,9-dimethyl-9H-fluoren-2-yl)-phenylamino}-phenyl-boronic acid
was used instead of
N-(biphenyl-4-yl)-N-{3-(4,4,5,5-tetramethyl-[1,3,2]dioxaboran-2-yl)phenyl}aniline.
As a result, 4.2 g (yield 25%) of 2,2"-bis{(9,9-dimethyl-9H-fluoren-2-yl)-phenylamino}-1,1':3',1"-terphenyl (Compound 1-47) was obtained as a white powder.

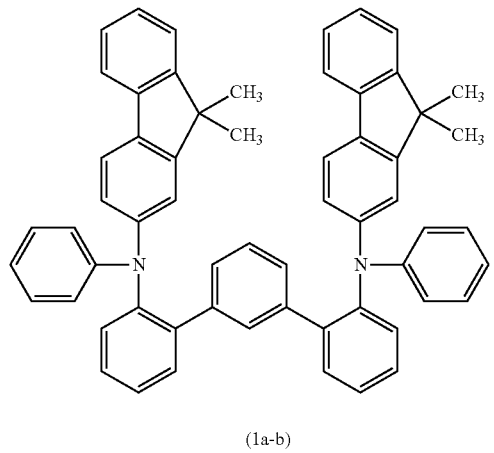

(1a-b)

In connection with the resulting white powder, its structure was identified using NMR. In $^1$H-NMR (CDCl$_3$), the following signals of 48 hydrogens were detected:

$\delta$ (ppm) = 7.60 (2H)

7.38 – 7.09 (14H)

6.95 – 6.71 (14H)

6.66 – 6.56 (4H)

6.35 (2H)

1.26 (12H)

Synthesis Example 14: Compound 1-49

Synthesis of 2,2"-bis{(9,9-dimethyl-9H-fluoren-2-yl)-phenylamino}-1,1':4',1"-terphenyl:
Reactions were performed under the same conditions as in Synthesis Example 3, except that
2-{(9,9-dimethyl-9H-fluoren-2-yl)-phenylamino}-phenyl-boronic acid
was used instead of
N-(biphenyl-4-yl)-N-{3-(4,4,5,5-tetramethyl-[1,3,2]dioxaboran-2-yl)phenyl}aniline.
As a result, 13.7 g (yield 76%) of 2,2"-bis{(9,9-dimethyl-9H-fluoren-2-yl)-phenylamino}-1,1':4',1"-terphenyl (Compound 1-49) was obtained as a white powder.

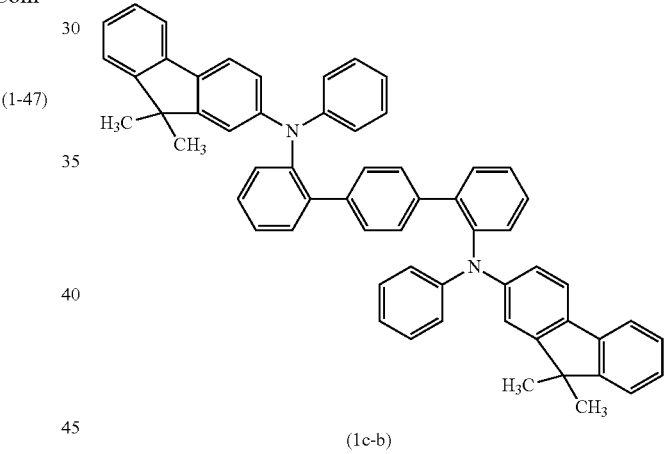

(1c-b)

In connection with the resulting white powder, its structure was identified using NMR. In $^1$H-NMR (THF-d$_8$), the following signals of 48 hydrogens were detected:

$\delta$ (ppm) = 7.53 (2H)

7.35 – 6.81 (30H)

6.76 (2H)

6.67 (2H)

1.29 (12H)

Synthesis Example 15: Compound 1-88

Synthesis of 4,4"-bis{(triphenylen-2-yl) phenylamino}-1,1':4',1"-terphenyl:

Reactions were performed under the same conditions as in Synthesis Example 6, except that
4,4"-diiodo-1,1':4',1"-terphenyl
was used instead of
4,4"-dibromo-1,1':3',1"-terphenyl
and
N-(triphenylen-2-yl)aniline
was used instead of
2-(phenylamino)-9,9-dimethyl-9H-fluorene.

As a result, 11.4 g (yield 74%) of 4,4"-bis{(triphenylen-2-yl)-phenylamino}-1,1':4',1"-terphenyl (Compound 1-88) was obtained as a white powder.

N-(4'-bromo-1,1'-biphenyl-4-yl)-{4-(1-phenyl-indol-4-yl)phenyl}aniline
was used instead of
N-(biphenyl-4-yl)-N-(4-bromophenyl)aniline,
and
N-{4-(4,4,5,5-tetramethyl-1,3,2-dioxaborolan-2-yl)phenyl}-(1,1'-biphenyl-4-yl)aniline
was used instead of
N-(9,9-dimethyl-9H-fluoren-2-yl)-N-{3'-(4,4,5,5-tetramethyl-[1,3,2]dioxaboran-2-yl)biphenyl-4-yl}aniline.

As a result, 6.80 g (yield 67%) of 4-{(biphenyl-4-yl)-phenylamino}-4"-[{4-(1-phenyl-indol-4-yl)phenyl}-phe-

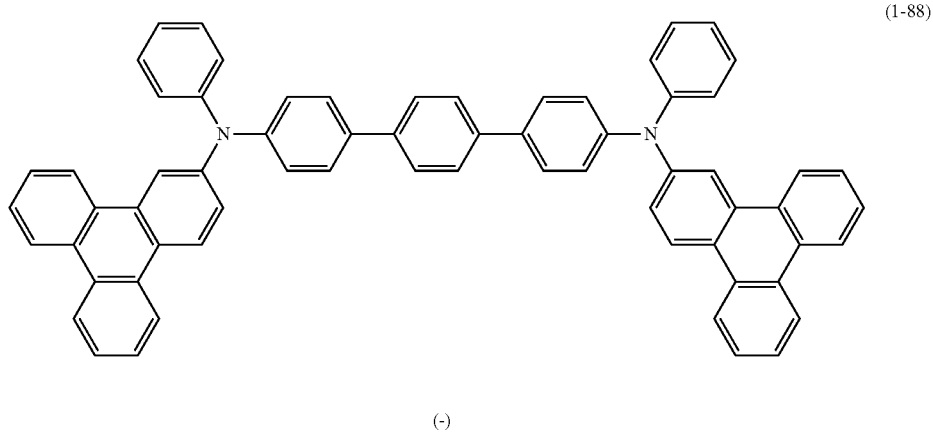 [SMILES: c1ccc(N(c2ccc(-c3ccc(-c4ccc(N(c5ccccc5)c5ccc6c7ccccc7c7ccccc7c6c5)cc4)cc3)cc2)c2ccc3c4ccccc4c4ccccc4c3c2)cc1]

(1-88)

In connection with the resulting white powder, its structure was identified using NMR. In $^1$H-NMR (THF-d$_8$), the following signals of 44 hydrogens were detected:

δ (ppm) = 8.72 – 8.62 (8H)
8.45 (2H)
8.36 (2H)
7.75 (4H)
7.70 – 7.21 (26H)
7.09 (2H)

Synthesis Example 16: Compound 1-91

Synthesis of 4-{(biphenyl-4-yl)-phenylamino}-4"-[{4-(1-phenyl-indol-4-yl)phenyl}-phenylamino]-1,1':4',1"-terphenyl:

Reactions were performed under the same conditions as in Synthesis Example 1, except that nylamino]-1,1':4',1"-terphenyl (Compound 1-91) was obtained as a light yellow powder.

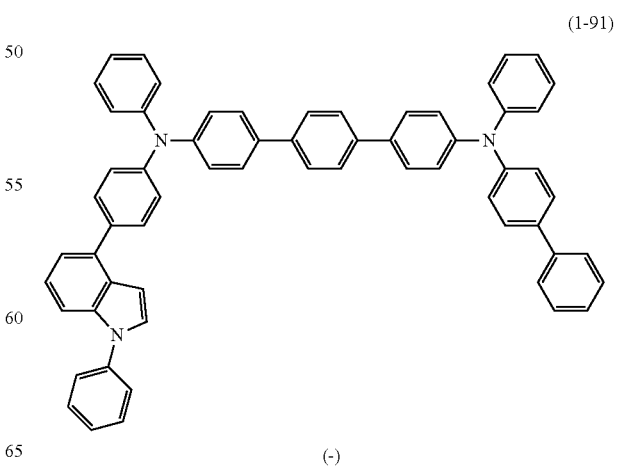

(1-91)

In connection with the resulting light yellow powder, its structure was identified using NMR. In $^1$H-NMR (THF-d$_8$), the following signals of 45 hydrogens were detected:

$$\delta \ (ppm) = 7.70 \ (4H)$$
$$7.68 - 7.50 \ (16H)$$
$$7.42 - 7.11 \ (23H)$$
$$7.05 \ (1H)$$
$$6.88 \ (1H)$$

Synthesis Example 17: Compound 1-101

Synthesis of 4,4''-bis{N-phenyl-N-(2-phenybiphenyl-4-yl)amino}-1,1':4',1''-terphenyl:

| | |
|---|---|
| A nitrogen-purged reaction vessel was charged with 4,4''-diiodo-1,1':4',1''-terphenyl | 13.0 g, |
| N-(2-phenylbiphenyl-4-yl)aniline | 20.0 g, |
| copper powder | 0.18 g, |
| potassium carbonate | 11.3 g, |
| 3,5-di-tert-butylsalicylic acid | 0.7 g, |
| sodium bisulfite | 0.86 g, |
| and | |
| dodecylbenzene | 30 ml. |

The charge was heated, and stirred for 24 hours at 210° C. to prepare a mixture. The mixture was cooled, and then 30 ml of xylene and 60 ml of methanol were added, whereafter the resulting precipitate was collected by filtration. To the precipitate, 250 ml of toluene and 20 g of silica were added, and the mixture was heated to 90° C. to prepare a precipitate solution. Then, insolubles were removed from the precipitate solution by hot filtration, and then the precipitate solution was concentrated. Then, ethyl acetate and methanol were added to the precipitate concentrate to precipitate a crude product, which was collected by filtration. Recrystallization of the crude product was performed using chlorobenzene, and then a reflux washing operation was performed using methanol. As a result, 16.9 g (yield 72%) of 4,4''-bis{N-phenyl-N-(2-phenybiphenyl-4-yl)amino}-1,1':4',1''-terphenyl (Compound 1-101) was obtained as a white powder.

In connection with the resulting white powder, its structure was identified using NMR. In $^1$H-NMR (CDCl$_3$), the following signals of 48 hydrogens were detected:

$$\delta \ (ppm) = 7.68 \ (4H)$$
$$7.62 - 7.55 \ (4H)$$
$$7.39 - 7.06 \ (40H)$$

Synthesis Example 18: Compound 1-103

Synthesis of 4,4''-bis{(2-phenylbiphenyl-4-yl)-phenylamino}-1,1':2',1''-terphenyl:

Reactions were performed under the same conditions as in Synthesis Example 6, except that
4,4''-dibromo-1,1':2',1''-terphenyl
was used instead of
4,4''-dibromo-1,1':3',1''-terphenyl
and
N-(2-phenylbiphenyl-4-yl)aniline
was used instead of
2-(phenylamino)-9,9-dimethyl-9H-fluorene.
As a result, 4.3 g (yield 42%) of 4,4''-bis{(2-phenylbiphenyl-4-yl)-phenylamino}-1,1':2',1''-terphenyl (Compound 1-103) was obtained as a white powder.

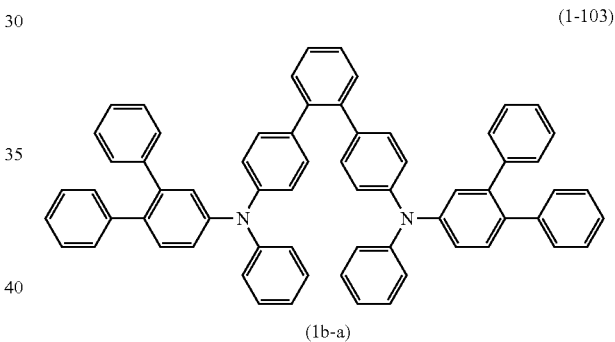

(1-103)

(1b-a)

In connection with the resulting white powder, its structure was identified using NMR. In $^1$H-NMR (CDCl$_3$), the following signals of 48 hydrogens were detected:

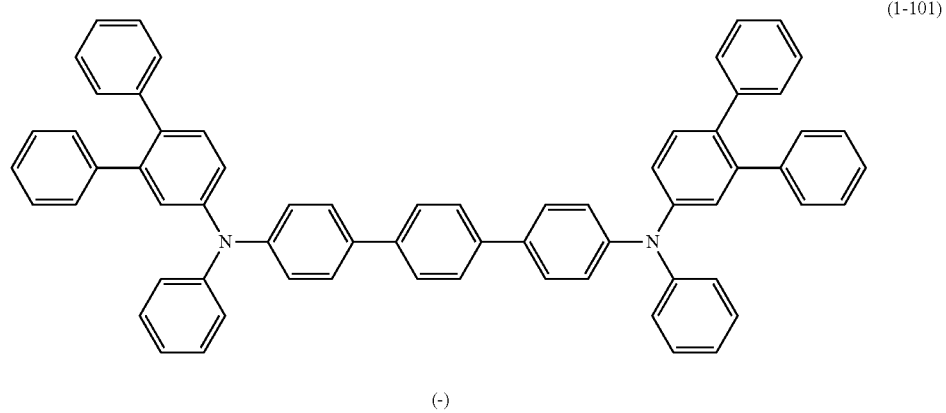 [SMILES: c1ccc(-c2ccc(N(c3ccccc3)c3ccc(-c4ccc(-c5ccc(N(c6ccccc6)c6ccc(-c7ccccc7)c(-c7ccccc7)c6)cc5)cc4)cc3)cc2-c2ccccc2)cc1]

(1-101)

$\delta\ (ppm) = 7.50 - 7.39\ (4H)$ $7.31 - 6.97\ (44H)$

Synthesis Example 19: Compound 1-104

Synthesis of 4,4"-bis{(2-phenylbiphenyl-4-yl)-phenylamino}-1,1':3',1"-terphenyl:

Reactions were performed under the same conditions as in Synthesis Example 6, except that
N-(2-phenylbiphenyl-4-yl)aniline
was used instead of
2-(phenylamino)-9,9-dimethyl-9H-fluorene.
As a result, 7.7 g (yield 53%) of 4,4"-bis{(2-phenylbiphenyl-4-yl)-phenylamino}-1,1':3',1"-terphenyl (Compound 1-104) was obtained as a white powder.

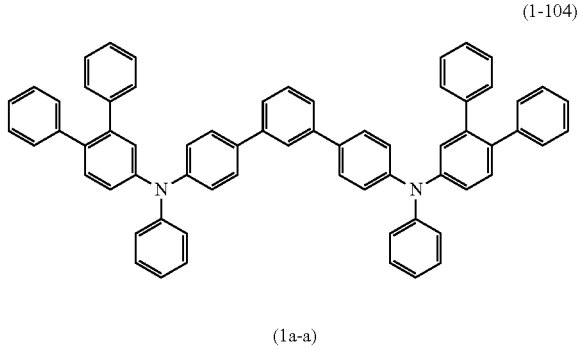 [SMILES: c1ccc(-c2ccc(N(c3ccccc3)c3ccc(-c4cccc(-c5ccc(N(c6ccccc6)c6ccc(-c7ccccc7)c(-c7ccccc7)c6)cc5)c4)cc3)cc2-c2ccccc2)cc1]

(1-104)

(1a-a)

In connection with the resulting white powder, its structure was identified using NMR. In $^1$H-NMR (CDCl$_3$), the following signals of 48 hydrogens were detected:

$\delta\ (ppm) = 7.81\ (2H)$ $7.61 - 7.48\ (14H)$ $7.39 - 7.06\ (32H)$

The various compounds obtained in the Synthesis Examples were measured for the glass transition temperature by a high-sensitivity differential scanning calorimeter (DSC3100SA, produced by Bruker AXS K.K.).

|  | Glass transition temperature |
|---|---|
| Compound of Synthesis Example 1 (Compound 1-5) | 117° C. |
| Compound of Synthesis Example 2 (Compound 1-6) | 117° C. |
| Compound of Synthesis Example 3 (Compound 1-21) | 103° C. |
| Compound of Synthesis Example 5 (Compound 1-32) | 115° C. |
| Compound of Synthesis Example 6 (Compound 1-34) | 124° C. |
| Compound of Synthesis Example 7 (Compound 1-37) | 114° C. |
| Compound of Synthesis Example 8 (Compound 1-38) | 119° C. |
| Compound of Synthesis Example 9 (Compound 1-39) | 106° C. |
| Compound of Synthesis Example 10 (Compound 1-41) | 127° C. |
| Compound of Synthesis Example 11 (Compound 1-42) | 111° C. |
| Compound of Synthesis Example 12 (Compound 1-45) | 122° C. |
| Compound of Synthesis Example 13 (Compound 1-47) | 116° C. |
| Compound of Synthesis Example 14 (Compound 1-49) | 117° C. |
| Compound of Synthesis Example 15 (Compound 1-88) | 163° C. |
| Compound of Synthesis Example 16 (Compound 1-91) | 125° C. |
| Compound of Synthesis Example 17 (Compound 1-101) | 124° C. |
| Compound of Synthesis Example 18 (Compound 1-103) | 115° C. |
| Compound of Synthesis Example 19 (Compound 1-104) | 122° C. |

The above results show that the arylamine compounds represented by the general formula (1) have a glass transition temperature of 100° C. or higher, demonstrating that they are stable in a thin film state.

Using each of the arylamine compounds obtained in the Synthesis Examples, a vapor deposited film with a film thickness of 100 nm was prepared on an ITO substrate, and its work function was measured using an ionization potential measuring device (PYS-202, produced by Sumitomo Heavy Industries, Ltd.).

|  | Work function |
|---|---|
| Compound of Synthesis Example 1 (Compound 1-5) | 5.68 eV |
| Compound of Synthesis Example 2 (Compound 1-6) | 5.65 eV |
| Compound of Synthesis Example 3 (Compound 1-21) | 5.79 eV |
| Compound of Synthesis Example 4 (Compound 1-22) | 5.83 eV |
| Compound of Synthesis Example 5 (Compound 1-32) | 5.69 eV |
| Compound of Synthesis Example 6 (Compound 1-34) | 5.65 eV |
| Compound of Synthesis Example 7 (Compound 1-37) | 5.67 eV |
| Compound of Synthesis Example 8 (Compound 1-38) | 5.64 eV |
| Compound of Synthesis Example 9 (Compound 1-39) | 5.66 eV |
| Compound of Synthesis Example 10 (Compound 1-41) | 5.69 eV |
| Compound of Synthesis Example 11 (Compound 1-42) | 5.75 eV |
| Compound of Synthesis Example 12 (Compound 1-45) | 5.76 eV |
| Compound of Synthesis Example 13 (Compound 1-47) | 5.72 eV |
| Compound of Synthesis Example 14 (Compound 1-49) | 5.72 eV |
| Compound of Synthesis Example 15 (Compound 1-88) | 5.62 eV |
| Compound of Synthesis Example 16 (Compound 1-91) | 5.67 eV |
| Compound of Synthesis Example 17 (Compound 1-101) | 5.67 eV |
| Compound of Synthesis Example 18 (Compound 1-103) | 5.75 eV |
| Compound of Synthesis Example 19 (Compound 1-104) | 5.76 eV |

The arylamine compounds represented by the general formula (1) were found to show a suitable energy level as compared with a work function of 5.4 eV which an ordinary hole transport material such as NPD or TPD has. Thus, these compounds are found to have satisfactory hole transport capability.

Synthesis Example 20: Compound 2-1

Synthesis of 7,7-dimethyl-12-(4-phenylquinazolin-2-yl)-7,12-dihydrobenzo[4,5]thieno[3,2-g]indeno[1,2-b]indole:

| A nitrogen-purged reaction vessel was charged with | |
|---|---|
| 7,7-dimethyl-7,12-dihydrobenzo[4,5]thieno[3,2-g]indeno[1,2-b]indole | 4.9 g, |
| 2-chloro-4-phenylquinazoline | 5.7 g, |
| tris(dibenzylideneacetone)dipalladium | 0.3 g, |
| tri-tert-butylphosphonium tetrafluoroborate | 0.4 g, |
| tert-butoxysodium | 4.0 g, |
| and | |
| xylene | 74 ml. |

The charge was heated, and stirred for 12 hours under reflux to prepare a mixture. The mixture was cooled to room temperature, and ethyl acetate and water were added, whereafter an organic layer was collected by liquid separation. The organic layer was concentrated, and then purified using a column chromatograph. As a result, 3.0 g (yield 38%) of 7,7-dimethyl-12-(4-phenylquinazolin-2-yl)-7,12-dihydrobenzo[4,5]thieno[3,2-g]indeno[1,2-b]indole (Compound 2-1) was obtained as a powder.

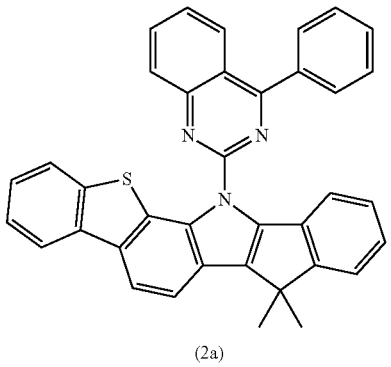

(2-1)

(2a)

Synthesis Example 21: Compound 2-2>

Synthesis of 7,7-dimethyl-12-(4-phenylbenzo[h]quinazolin-2-yl)-7,12-dihydrobenzo[4,5]thieno[3,2-g]indeno[1,2-b]indole:

Reactions were performed under the same conditions as in Synthesis Example 20, except that
2-chloro-4-phenylbenzo[h]quinazoline
was used instead of
2-chloro-4-phenylquinazoline.
As a result, 3.2 g (yield 38%) of 7,7-dimethyl-12-(4-phenylbenzo[h]quinazolin-2-yl)-7,12-dihydrobenzo[4,5]thieno[3,2-g]indeno[1,2-b]indole (Compound 2-2) was obtained as a powder.

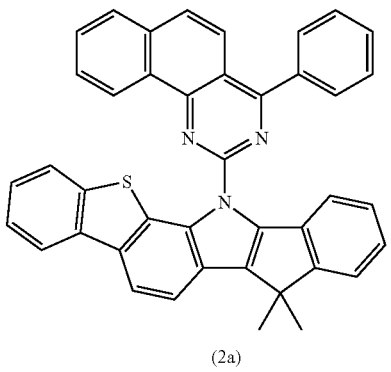

(2-2)

(2a)

Synthesis Example 22: Compound 2-3>

Synthesis of 12-(4,7-diphenylquinazolin-2-yl)-7,7-dimethyl-7,12-dihydrobenzo[4,5]thieno[3,2-g]indeno[1,2-b]indole:

Reactions were performed under the same conditions as in Synthesis Example 20, except that
2-chloro-4,7-diphenylquinazoline
was used instead of
2-chloro-4-phenylquinazoline.

As a result, 3.3 g (yield 38%) of 12-(4,7-diphenylquinazolin-2-yl)-7,7-dimethyl-7,12-dihydrobenzo[4,5]thieno[3,2-g]indeno[1,2-b]indole (Compound 2-3) was obtained as a powder.

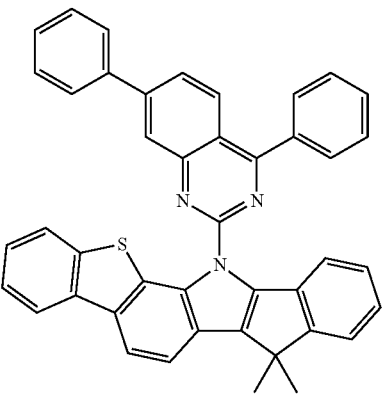

(2-3)

(2a)

Synthesis Example 23: Compound 2-4>

Synthesis of 12-(4,6-diphenylquinazolin-2-yl)-7,7-dimethyl-7,12-dihydrobenzo[4,5]thieno[3,2-g]indeno[1,2-b]indole:

Reactions were performed under the same conditions as in Synthesis Example 20, except that
2-chloro-4,6-diphenylquinazoline
was used instead of
2-chloro-4-phenylquinazoline.
As a result, 3.3 g (yield 38%) of 12-(4,6-diphenylquinazolin-2-yl)-7,7-dimethyl-7,12-dihydrobenzo[4,5]thieno[3,2-g]indeno[1,2-b]indole (Compound 2-4) was obtained as a powder.

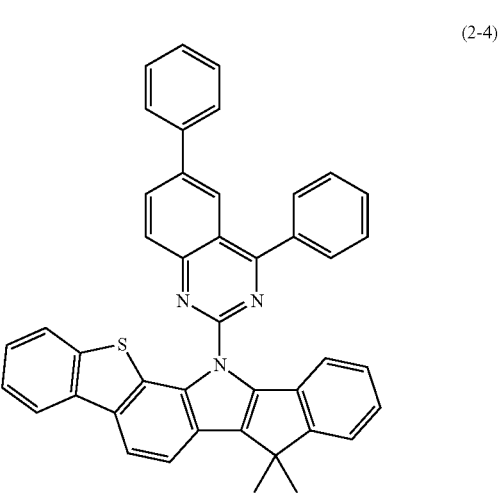

(2-4)

(2a)

Synthesis Example 24: Compound 2-5>

Synthesis of 13,13-dimethyl-8-(4-phenylquinazolin-2-yl)-8,13-dihydrobenzo[4,5]thieno[3,2-e]indeno[1, 2-b]indole:

Reactions were performed under the same conditions as in Synthesis Example 20, except that 13,13-dimethyl-8,13-dihydrobenzo[4,5]thieno[3,2-e]indeno[1,2-b]indole was used instead of 7,7-dimethyl-7,12-dihydrobenzo[4,5]thieno[3,2-g]indeno[1,2-b]indole.

As a result, 3.0 g (yield 38%) of 13,13-dimethyl-8-(4-phenylquinazolin-2-yl)-8,13-dihydrobenzo[4,5]thieno[3,2-e]indeno[1,2-b]indole (Compound 2-5) was obtained as a powder.

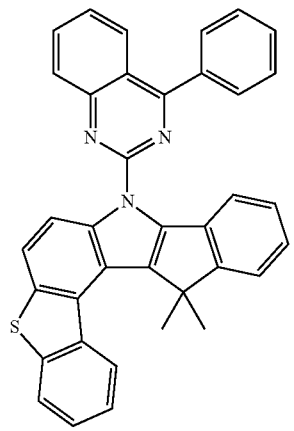

(2-5)

(2b)

Synthesis Example 25: Compound 2-6

Synthesis of 8-(4,6-diphenylquinazolin-2-yl)-13,13-dimethyl-8,13-dihydrobenzo[4,5]thieno[3,2-e]indeno[1,2-b]indole:

Reactions were performed under the same conditions as in Synthesis Example 24, except that 2-chloro-4,6-diphenylquinazoline
was used instead of
2-chloro-4-phenylquinazoline.

As a result, 3.3 g (yield 38%) of 8-(4,6-diphenylquinazolin-2-yl)-13,13-dimethyl-8,13-dihydrobenzo[4,5]thieno[3,2-e]indeno[1,2-b]indole (Compound 2-6) was obtained as a powder.

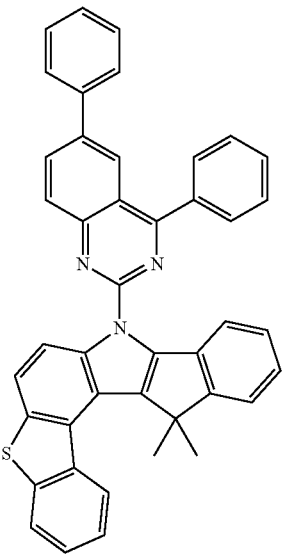

(2-6)

(2b)

Synthesis Example 26: Compound 2-7

Synthesis of 7,7,13,13-tetramethyl-5-(4-phenylquinazolin-2-yl)-7,13-dihydro-5H-diindeno[1,2-b:1',2'-f]indole:
Reactions were performed under the same conditions as in Synthesis Example 20, except that
7,7,13,13-tetramethyl-7,13-dihydro-5H-diindeno[1,2-b:1',2'-f]indole
was used instead of
7,7-dimethyl-7,12-dihydrobenzo[4,5]thieno[3,2-g]indeno[1,2-b]indole.
As a result, 3.0 g (yield 38%) of 7,7,13,13-tetramethyl-5-(4-phenylquinazolin-2-yl)-7,13-dihydro-5H-diindeno[1,2-b:1',2'-f]indole (Compound 2-7) was obtained as a powder.

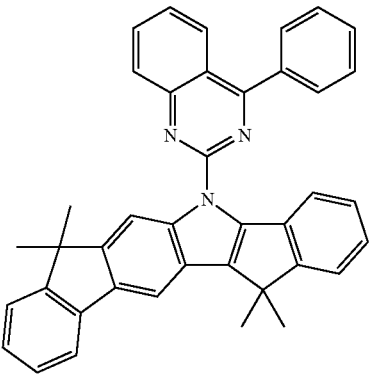

(2-7)

(2c)

Synthesis Example 27: Compound 2-8

Synthesis of 7,7,13,13-tetramethyl-5-[3-(4-phenylquinazolin-2-yl)phenyl]-7,13-dihydro-5H-diindeno[1,2-b:1',2'-f]indole:

Reactions were performed under the same conditions as in Synthesis Example 26, except that
2-(3-bromophenyl)-4-phenylquinazoline
was used instead of
2-chloro-4-phenylquinazoline.
As a result, 3.4 g (yield 38%) of 7,7,13,13-tetramethyl-5-[3-(4-phenylquinazolin-2-yl)phenyl]-7,13-dihydro-5H-diindeno[1,2-b:1',2'-f]indole (Compound 2-8) was obtained as a powder.

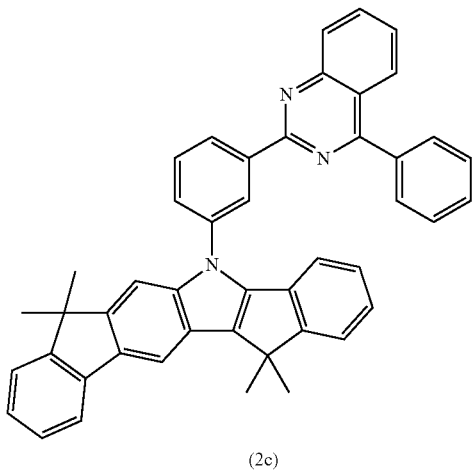

(2c)

Synthesis Example 28: Compound 2-9>

Synthesis of 7,7-dimethyl-12-(4-phenylbenzo[h]quinazolin-2-yl)-7,12-dihydrobenzofuro[3,2-g]indeno[1,2-b]indole:
Reactions were performed under the same conditions as in Synthesis Example 21, except that
7,7-dimethyl-7,12-dihydrobenzofuro[3,2-g]indeno[1,2-b]indole
was used instead of
7,7-dimethyl-7,12-dihydrobenzo[4,5]thieno[3,2-g]indeno[1,2-b]indole.
As a result, 3.0 g (yield 38%) of 7,7-dimethyl-12-(4-phenylbenzo[h]quinazolin-2-yl)-7,12-dihydrobenzofuro[3,2-g]indeno[1,2-b]indole (Compound 2-9) was obtained as a powder.

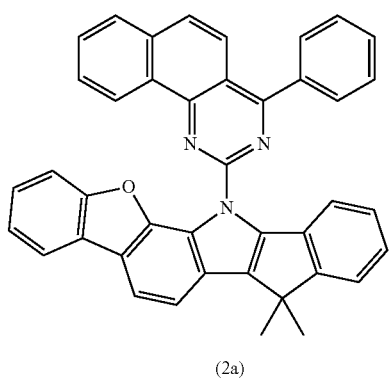

(2a)

Synthesis Example 29: Compound 2-10>

Synthesis of 12-(4,6-diphenylbenzo[h]quinazolin-2-yl)-7,7-dimethyl-7,12-dihydrobenzofuro[3,2-g]indeno[1,2-b]indole:
Reactions were performed under the same conditions as in Synthesis Example 28, except that
2-chloro-4,6-diphenylbenzo[h]quinazoline
was used instead of
2-chloro-4-phenylbenzo[h]quinazoline.
As a result, 3.5 g (yield 38%) of 12-(4,6-diphenylbenzo[h]quinazolin-2-yl)-7,7-dimethyl-7,12-dihydrobenzofuro[3,2-g]indeno[1,2-b]indole (Compound 2-10) was obtained as a powder.

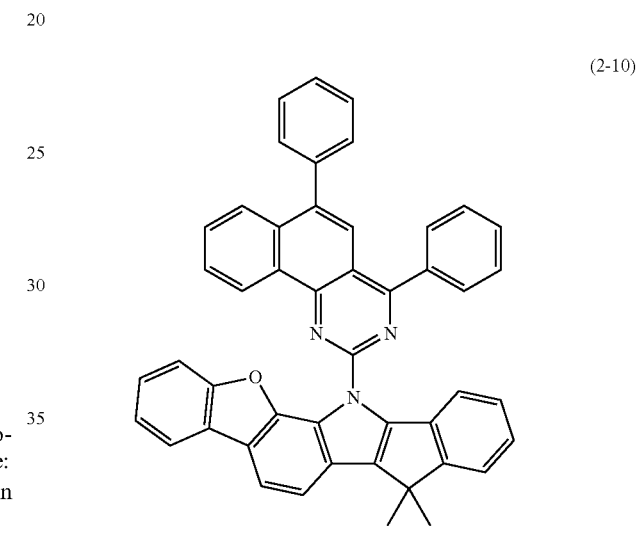

(2a)

Synthesis Example 30: Compound 2-11>

Synthesis of 13,13-dimethyl-8-(4-phenylquinazolin-2-yl)-8,13-dihydrobenzofuro[3,2-e]indeno[1,2-b]indole:

Reactions were performed under the same conditions as in Synthesis Example 20, except that 13,13-dimethyl-8,13-dihydrobenzofuro[3,2-e]indeno[1,2-b]indole was used instead of 7,7-dimethyl-7,12-dihydrobenzo[4,5]thieno[3,2-g]indeno[1,2-b]indole.

As a result, 3.0 g (yield 38%) of 13,13-dimethyl-8-(4-phenylquinazolin-2-yl)-8,13-dihydrobenzofuro[3,2-e]indeno[1,2-b]indole (Compound 2-11) was obtained as a powder.

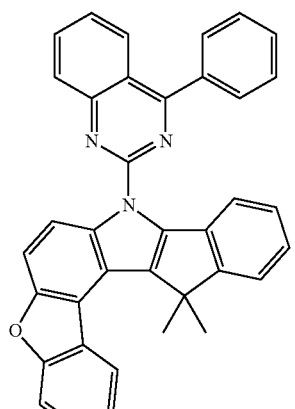

(2-11)

Synthesis Example 31: Compound 2-12

Synthesis of 13,13-dimethyl-8-(4,6-diphenylquinazolin-2-yl)-8,13-dihydrobenzofuro[3,2-e]indeno[1,2-b]indole:

Reactions were performed under the same conditions as in Synthesis Example 30, except that 2-chloro-4,6-diphenylquinazoline was used instead of 2-chloro-4-phenylquinazoline.

As a result, 3.2 g (yield 38%) of 13,13-dimethyl-8-(4,6-diphenylquinazolin-2-yl)-8,13-dihydrobenzofuro[3,2-e]indeno[1,2-b]indole (Compound 2-12) was obtained as a powder.

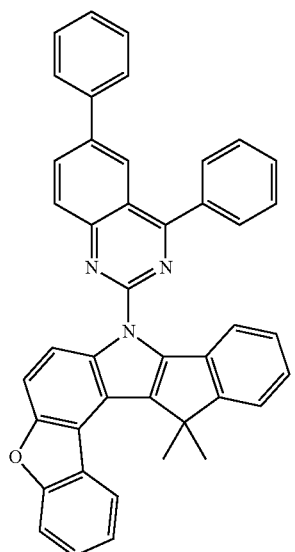

(2-12)

Synthesis Example 32: Compound 3-1>

Synthesis of 13-(4,6-diphenylquinazolin-2-yl)-7,7-dimethyl-7,13-dihydroindeno[2',1':4,5]thieno[2,3-a]carbazole:

Reactions were performed under the same conditions as in Synthesis Example 31, except that 7,7-dimethyl-7,13-dihydroindeno[2',1':4,5]thieno[2,3-a]carbazole was used instead of 13,13-dimethyl-8,13-dihydrobenzofuro[3,2-e]indeno[1,2-b]indole.

As a result, 7.0 g (yield 38%) of 13-(4,6-diphenylquinazolin-2-yl)-7,7-dimethyl-7,13-dihydroindeno[2',1':4,5]thieno[2,3-a]carbazole (Compound 3-1) was obtained as a powder.

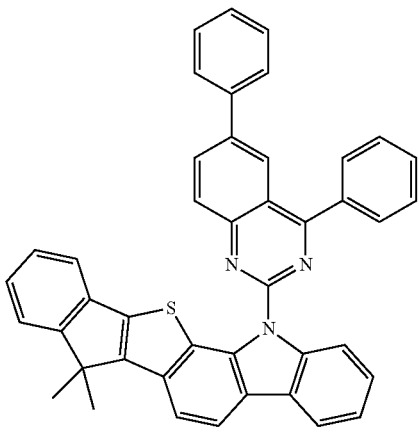

(3-1)

Synthesis Example 33: Compound 3-2>

Synthesis of 13-[4-(biphenyl-4-yl)quinazolin-2-yl)-7,7-dimethyl-7,13-dihydroindeno[2',1':4,5]thieno[2,3-a]carbazole:

Reactions were performed under the same conditions as in Synthesis Example 32, except that 4-(biphenyl-4-yl)-2-chloroquinazoline was used instead of 2-chloro-4,6-diphenylquinazoline.

As a result, 6.7 g (yield 37%) of 13-[4-(biphenyl-4-yl)quinazolin-2-yl)-7,7-dimethyl-7,13-dihydroindeno[2',1':4,5]thieno[2,3-a]carbazole (Compound 3-2) was obtained as a powder.

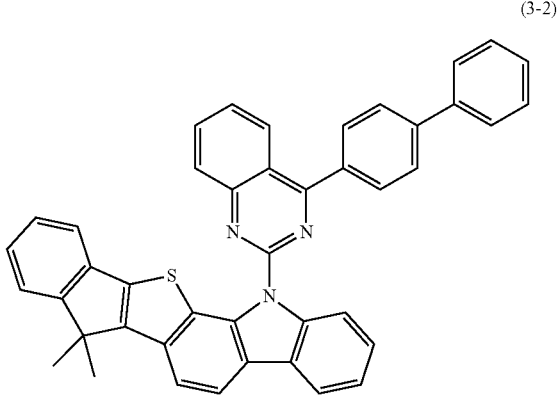

(3-2)

Synthesis Example 34: Compound 3-3>

Synthesis of 7,7-dimethyl-13-[4-(phenyl-d$_5$) quinazolin-2-yl]-7,13-dihydroindeno[2',1':4,5]thieno[2,3-a]carbazole:

Reactions were performed under the same conditions as in Synthesis Example 32, except that 2-chloro-4-(phenyl-d$_5$) quinazoline was used instead of 2-chloro-4,6-diphenylquinazoline.

As a result, 8.4 g (yield 32%) of 7,7-dimethyl-13-[4-(phenyl-d$_5$) quinazolin-2-yl]-7,13-dihydroindeno[2',1':4,5]thieno[2,3-a]carbazole (Compound 3-3) was obtained as a powder.

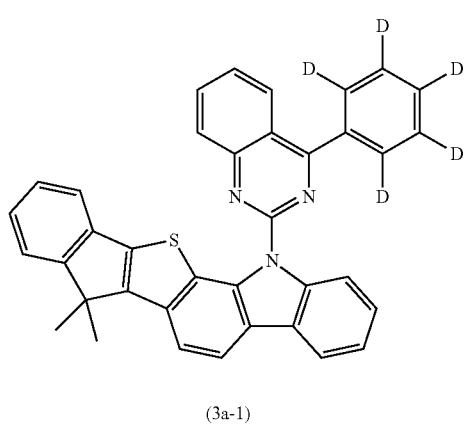

(3-3)

(3a-1)

Synthesis Example 35: Compound 3-4>

Synthesis of 7,7-dimethyl-13-[4-(4-phenylquinazolin-2-yl)phenyl]-7,13-dihydroindeno[2',1':4,5]thieno[2,3-a]carbazole:

Reactions were performed under the same conditions as in Synthesis Example 32, except that 2-(4-bromophenyl)-4-phenylquinazoline was used instead of 2-chloro-4,6-diphenylquinazoline.

As a result, 5.2 g (yield 28%) of 7,7-dimethyl-13-[4-(4-phenylquinazolin-2-yl)phenyl]-7,13-dihydroindeno[2',1':4,5]thieno[2,3-a]carbazole (Compound 3-4) was obtained as a powder.

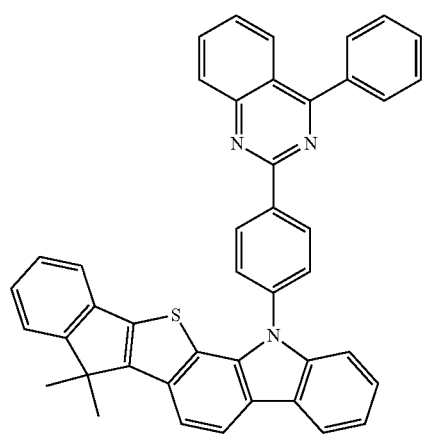

(3-4)

(3a-1)

Synthesis Example 36: Compound 3-5>

Synthesis of 7,7-dimethyl-13-[3-(4-phenylquinazolin-2-yl)phenyl]-7,13-dihydroindeno[2',1':4,5]thieno[2,3-a]carbazole:

Reactions were performed under the same conditions as in Synthesis Example 32, except that 2-(3-bromophenyl)-4-phenylquinazoline was used instead of 2-chloro-4,6-diphenylquinazoline.

As a result, 8.4 g (yield 32%) of 7,7-dimethyl-13-[3-(4-phenylquinazolin-2-yl)phenyl]-7,13-dihydroindeno[2',1':4,5]thieno[2,3-a]carbazole (Compound 3-5) was obtained as a powder.

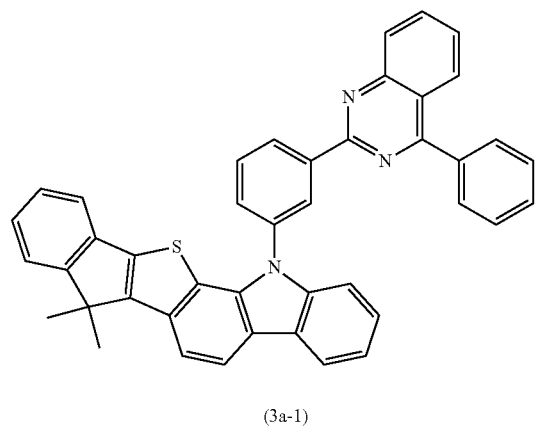

(3-5)

(3a-1)

Synthesis Example 37: Compound 3-6>

Synthesis of 7,7-dimethyl-13-(4-phenylbenzo[h]quinazolin-2-yl)-7,13-dihydroindeno[2',1':4,5]thieno[2,3-a]carbazole:

Reactions were performed under the same conditions as in Synthesis Example 32, except that 2-chloro-4-phenylbenzo[h]quinazoline was used instead of 2-chloro-4,6-diphenylquinazoline.

As a result, 8.4 g (yield 32%) of 7,7-dimethyl-13-(4-phenylbenzo[h]quinazolin-2-yl)-7,13-dihydroindeno[2',1':4,5]thieno[2,3-a]carbazole (Compound 3-6) was obtained as a powder.

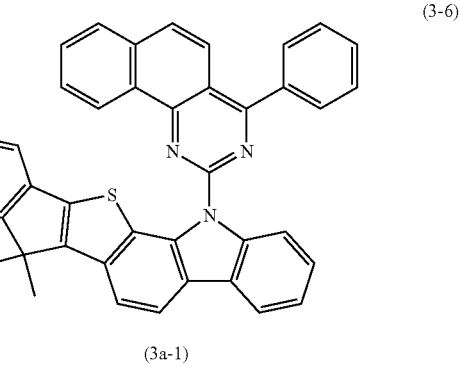

(3-6)

(3a-1)

Synthesis Example 38: Compound 3-7>

Synthesis of 8,8-dimethyl-5-(4-phenylbenzo[h]quinazolin-2-yl)-5,8-dihydroindeno[2',1':4,5]thieno[3,2-c]carbazole:

Reactions were performed under the same conditions as in Synthesis Example 37, except that 8,8-dimethyl-5,8-dihydroindeno[2',1':4,5]thieno[3,2-c]carbazole was used instead of 7,7-dimethyl-7,13-dihydroindeno[2',1':4,5]thieno[2,3-a]carbazole.

As a result, 9.3 g (yield 35%) of 8,8-dimethyl-5-(4-phenylbenzo[h]quinazolin-2-yl)-5,8-dihydroindeno[2',1':4,5]thieno[3,2-c]carbazole (Compound 3-7) was obtained as a powder.

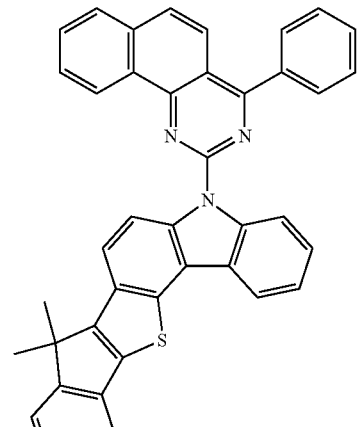

(3-7)

Synthesis Example 39: Compound 3-8>

Synthesis of 7,7-dimethyl-13-(4-phenylquinazolin-2-yl)-7,13-dihydroindeno[2',1':4,5]furo[2,3-a]carbazole:

Reactions were performed under the same conditions as in Synthesis Example 20, except that 7,7-dimethyl-7,13-dihydroindeno[2',1':4,5]furo[2,3-a]carbazole was used instead of 7,7-dimethyl-7,12-dihydrobenzo[4,5]thieno[3,2-g]indeno[1,2-b]indole.

As a result, 6.2 g (yield 32%) of 7,7-dimethyl-13-(4-phenylquinazolin-2-yl)-7,13-dihydroindeno[2',1':4,5]furo[2,3-a]carbazole (Compound 3-8) was obtained as a powder.

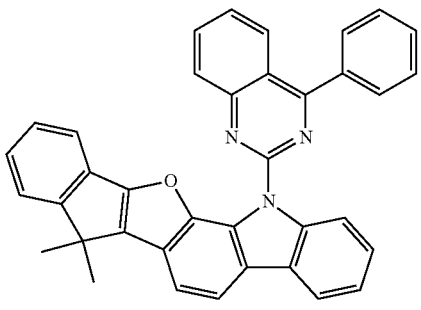

(3-8)

(3a-1)

Synthesis Example 40: Compound 3-9>

Synthesis of 7,7-dimethyl-13-(4-phenylbenzo[h]quinazolin-2-yl)-7,13-dihydroindeno[2',1':4,5]furo[2,3-a]carbazole:

Reactions were performed under the same conditions as in Synthesis Example 39, except that 2-chloro-4-phenylbenzo[h]quinazoline was used instead of 2-chloro-4-phenylquinazoline.

As a result, 8.6 g (yield 30%) of 7,7-dimethyl-13-(4-phenylbenzo[h]quinazolin-2-yl)-7,13-dihydroindeno[2',1':4,5]furo[2,3-a]carbazole (Compound 3-9) was obtained as a powder.

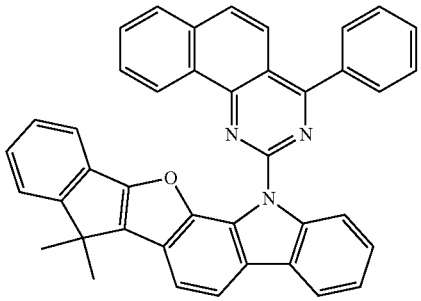

(3-9)

(3a-1)

Synthesis Example 41: Compound 3-10>

Synthesis of 13-(4,6-diphenylquinazolin-2-yl)-7,7-dimethyl-7,13-dihydroindeno[2',1':4,5]furo[2,3-a]carbazole:

Reactions were performed under the same conditions as in Synthesis Example 39, except that 2-chloro-4,6-diphenylquinazoline was used instead of 2-chloro-4-phenylquinazoline.

As a result, 7.2 g (yield 29%) of 13-(4,6-diphenylquinazolin-2-yl)-7,7-dimethyl-7,13-dihydroindeno[2',1':4,5]furo[2,3-a]carbazole (Compound 3-10) was obtained as a powder.

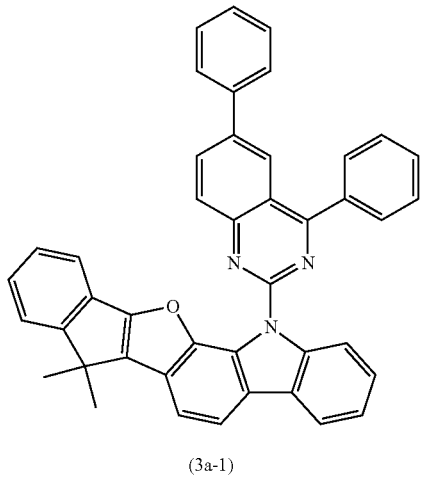

(3-10)

(3a-1)

<Synthesis Example 42: Compound 3-11>

Synthesis of 7,7-diphenyl-13-(4-phenylquinazolin-2-yl)-7,13-dihydroindeno[2',1':4,5]thieno[2,3-a]carbazole:

Reactions were performed under the same conditions as in Synthesis Example 20, except that
7,7-diphenyl-7,13-dihydroindeno[2',1':4,5]thieno[3,2-a]carbazole
was used instead of
7,7-dimethyl-7,12-dihydrobenzo[4,5]thieno[3,2-g]indeno[1,2-b]indole.
As a result, 6.7 g (yield 37%) of 7,7-diphenyl-13-(4-phenylquinazolin-2-yl)-7,13-dihydroindeno[2',1':4,5]thieno[2,3-a]carbazole (Compound 3-11) was obtained as a powder.

(3-11)

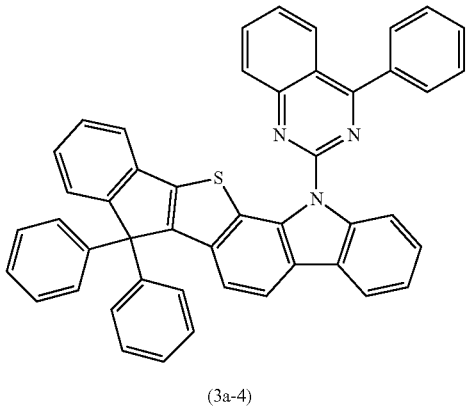

(3a-4)

<Synthesis Example 43: Compound 3-12>

Synthesis of 9,9-dimethyl-15-(4-phenylquinazolin-2-yl)-9,15-dihydrobenzo[a]indeno[2',1':4,5]thieno[3,2-i]carbazole:

Reactions were performed under the same conditions as in Synthesis Example 20, except that
9,9-dimethyl-9,15-dihydrobenzo[a]indeno[2',1':4,5]thieno[3,2-i]carbazole
was used instead of
7,7-dimethyl-7,12-dihydrobenzo[4,5]thieno[3,2-g]indeno[1,2-b]indole.
As a result, 4.8 g (yield 42%) of 9,9-dimethyl-15-(4-phenylquinazolin-2-yl)-9,15-dihydrobenzo[a]indeno[2',1':4,5]thieno[3,2-i]carbazole (Compound 3-12) was obtained as a powder.

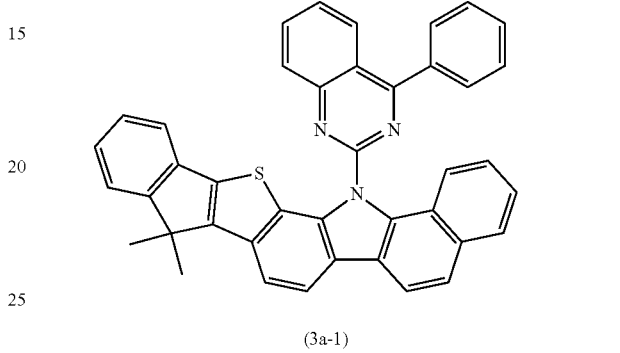

(3-12)

(3a-1)

<Synthesis Example 44: Compound 3-13>

Synthesis of 7-phenyl-13-(4-phenylquinazolin-2-yl)-7,13-dihydroindolo[2',3':4,5]thieno[2,3-a]carbazole:

Reactions were performed under the same conditions as in Synthesis Example 20, except that
7-phenyl-7,13-dihydroindolo[2',3':4,5]thieno[2,3-a]carbazole
was used instead of
7,7-dimethyl-7,12-dihydrobenzo[4,5]thieno[3,2-g]indeno[1,2-b]indole.
As a result, 4.3 g (yield 43%) of 7-phenyl-13-(4-phenylquinazolin-2-yl)-7,13-dihydroindolo[2',3':4,5]thieno[2,3-a]carbazole (Compound 3-13) was obtained as a powder.

(3-13)

(3b-1)

<Synthesis Example 45: Compound 3-14>

Synthesis of 12,12-dimethyl-1-(4-phenylquinazolin-2-yl)-1,12-dihydroindeno[1',2':4,5]thieno[2,3-a]carbazole:

Reactions were performed under the same conditions as in Synthesis Example 20, except that
12,12-dimethyl-1,12-dihydroindeno[1',2':4,5]thieno[2,3-a]carbazole
was used instead of
7,7-dimethyl-7,12-dihydrobenzo[4,5]thieno[3,2-g]indeno[1,2-b]indole.
As a result, 6.3 g (yield 44%) of 12,12-dimethyl-1-(4-phenylquinazolin-2-yl)-1,12-dihydroindeno[1',2':4,5]thieno[2,3-a]carbazole (Compound 3-14) was obtained as a powder.

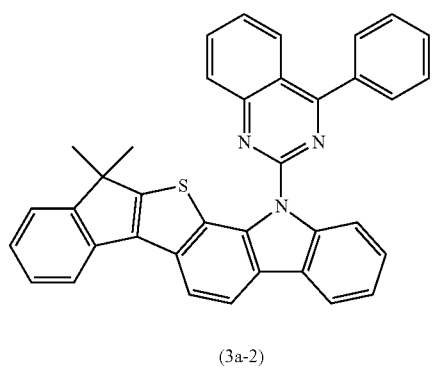

(3-14)

(3a-2)

Synthesis Example 46: Compound 3-15

Synthesis of 7,7-dimethyl-13-(naphthalen-2-yl)-7,13-dihydroindeno[2',1':4,5]thieno[2,3-a]carbazole:
Reactions were performed under the same conditions as in Synthesis Example 32, except that
2-bromonaphthalene
was used instead of
2-chloro-4,6-diphenylquinazoline.
As a result, 5.4 g (yield 47%) of 7,7-dimethyl-13-(naphthalen-2-yl)-7,13-dihydroindeno[2',1':4,5]thieno[2,3-a]carbazole (Compound 3-15) was obtained as a powder.

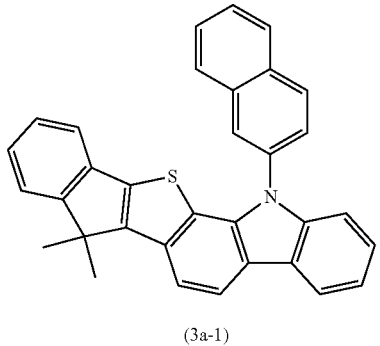

(3-15)

(3a-1)

Example 1

As shown in FIG. 1, the hole injection layer 3, the first hole transport layer 5a, the second hole transport layer 5b, the luminous layer 6, the electron transport layer 7, the electron injection layer 8, and the cathode (aluminum electrode) 9 were vapor-deposited in this order on an ITO electrode formed beforehand as the transparent anode 2 on the glass substrate 1 to prepare the organic EL device.

Concretely, the glass substrate 1 having a 150 nm thick ITO film formed thereon was ultrasonically cleaned for 20 minutes in isopropyl alcohol, and then dried for 10 minutes on a hot plate heated to 200° C. Then, the glass substrate with ITO was subjected to UV/ozone treatment for 15 minutes. Then, the ITO-equipped glass substrate was attached inside a vacuum vapor deposition device, and the pressure was reduced to 0.001 Pa or lower.

Then, the hole injection layer 3 was formed. Concretely, HIM-1 represented by the following structural formula was vapor-deposited so as to cover the transparent anode 2, thereby forming the hole injection layer 3 in a film thickness of 5 nm.

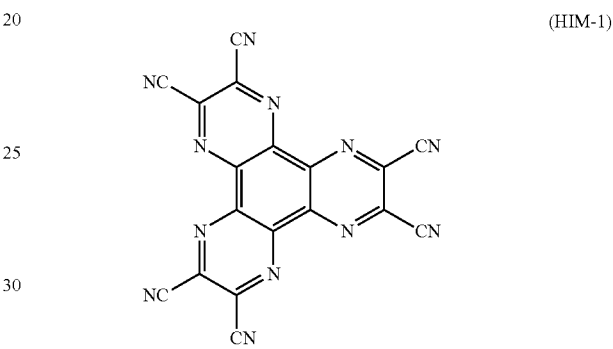

(HIM-1)

Then, the first hole transport layer 5a was formed. Concretely, a triarylamine compound 6-1 represented by the following structural formula was vapor-deposited on the hole injection layer 3 to form the first hole transport layer 5a with a film thickness of 60 nm.

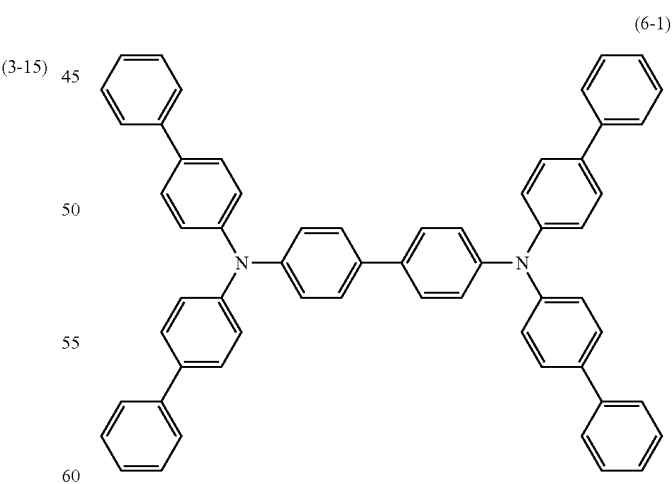

(6-1)

Then, the second hole transport layer 5b was formed. Concretely, Compound 1-5 of Synthesis Example 1 was vapor-deposited on the first hole transport layer 5a to form the second hole transport layer 5b with a film thickness of 5 nm.

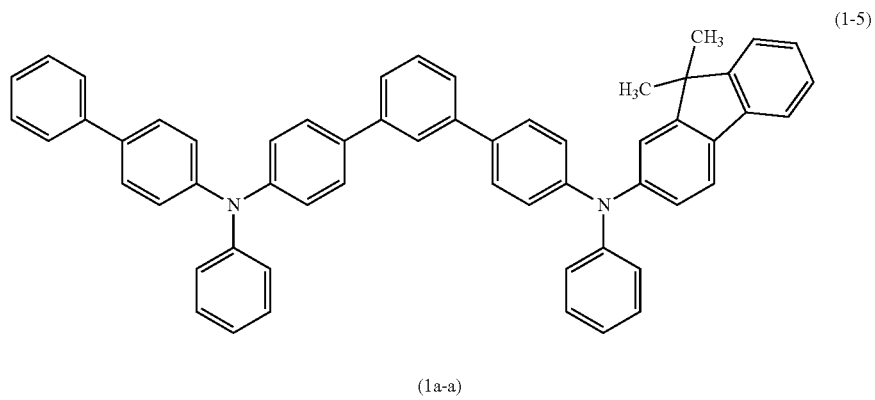 [SMILES: CC1(C)c2ccccc2-c2ccc(N(c3ccccc3)c3ccc(-c4cccc(-c5ccc(N(c6ccccc6)c6ccc(-c7ccccc7)cc6)cc5)c4)cc3)cc21]

(1a-a)

Then, the luminous layer 6 was formed. Concretely, a compound EMD-1 of the following structural formula and Compound 2-4 of Synthesis Example 23 were binary vapor deposited on the second hole transport layer 5b at such vapor deposition rates that the vapor deposition rate ratio was EMD-1:Compound 2-4=5:95, whereby the luminous layer 6 was formed in a film thickness of 20 nm.

Then, the electron transport layer 7 was formed. Concretely, a pyrimidine derivative 4-123 of the following structural formula and a compound ETM-1 of the following structural formula were binary vapor deposited on the luminous layer 6 at such vapor deposition rates that the vapor deposition rate ratio was pyrimidine derivative 4-123:ETM-1=50:50, whereby the electron transport layer 7 was formed in a film thickness of 30 nm.

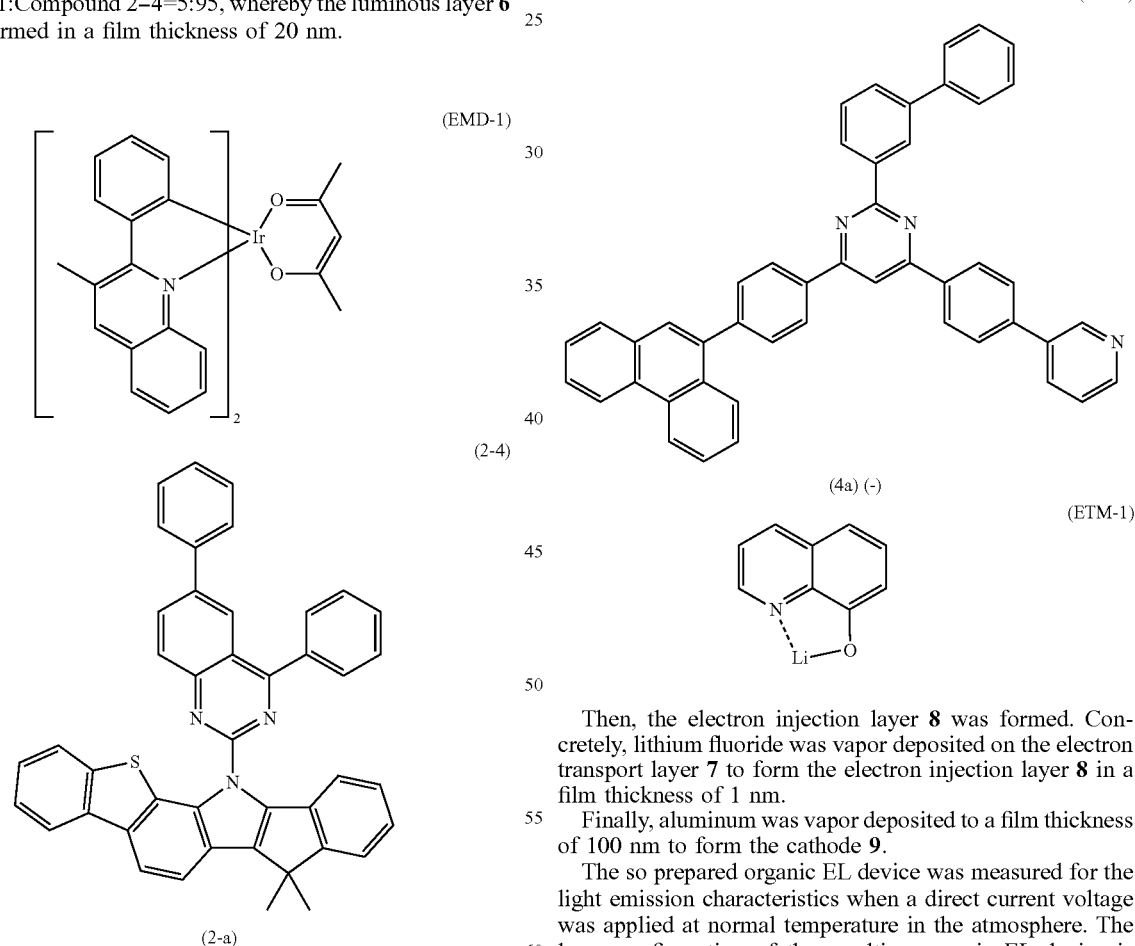

Then, the electron injection layer 8 was formed. Concretely, lithium fluoride was vapor deposited on the electron transport layer 7 to form the electron injection layer 8 in a film thickness of 1 nm.

Finally, aluminum was vapor deposited to a film thickness of 100 nm to form the cathode 9.

The so prepared organic EL device was measured for the light emission characteristics when a direct current voltage was applied at normal temperature in the atmosphere. The layer configuration of the resulting organic EL device is shown in Table 1, and the results of the measurements are shown in Table 2.

Example 2

An organic EL device was prepared under the same conditions as in Example 1, except that Compound 1-34 of Synthesis Example 6 was used instead of Compound 1-5 of Synthesis Example 1, as the material for the second hole transport layer 5b. The resulting organic EL device was measured for the light emission characteristics when a direct current voltage was applied at normal temperature in the atmosphere. The layer configuration is shown in Table 1, and the results of the measurements are shown in Table 2.

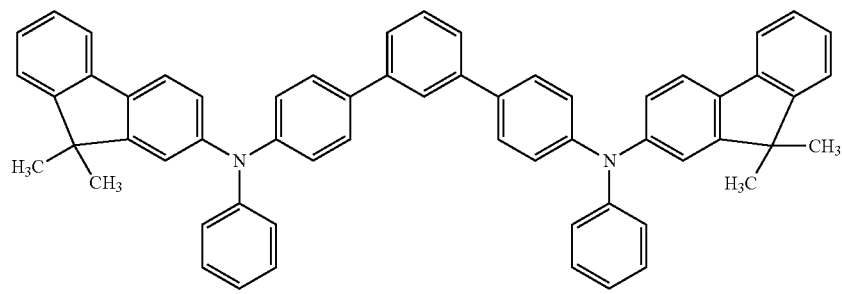

(1-34)

(1a-a)

Example 3

An organic EL device was prepared under the same conditions as in Example 1, except that a pyrimidine derivative 4-125 of the following structural formula was used, instead of the pyrimidine derivative 4-123, as the material for the electron transport layer 7. The resulting organic EL device was measured for the light emission characteristics when a direct current voltage was applied at normal temperature in the atmosphere. The layer configuration is shown in Table 1, and the results of the measurements are shown in Table 2.

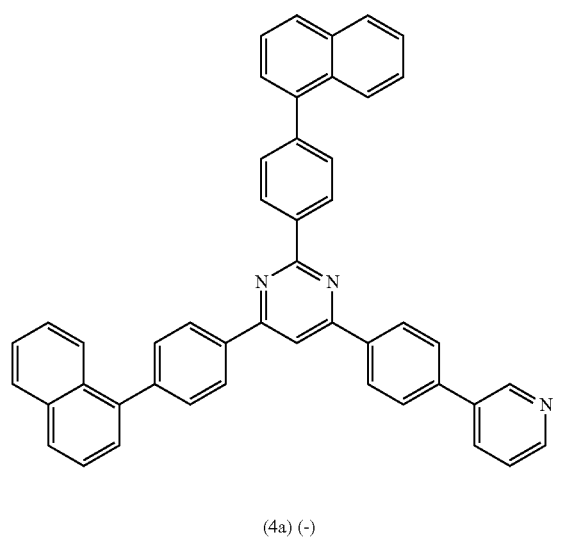

(4-125)

(4a) (-)

Example 4

An organic EL device was prepared under the same conditions as in Example 3, except that Compound 1-34 of Synthesis Example 6 was used instead of Compound 1-5 of Synthesis Example 1, as the material for the second hole transport layer 5b. The resulting organic EL device was measured for the light emission characteristics when a direct current voltage was applied at normal temperature in the atmosphere. The layer configuration is shown in Table 1, and the results of the measurements are shown in Table 2.

Example 5

An organic EL device was prepared under the same conditions as in Example 1, except that Compound 3-14 of Synthesis Example 45 was used instead of Compound 2-4 of Synthesis Example 23, as the material for the luminous layer 6. The resulting organic EL device was measured for the light emission characteristics when a direct current voltage was applied at normal temperature in the atmosphere. The layer configuration is shown in Table 1, and the results of the measurements are shown in Table 2.

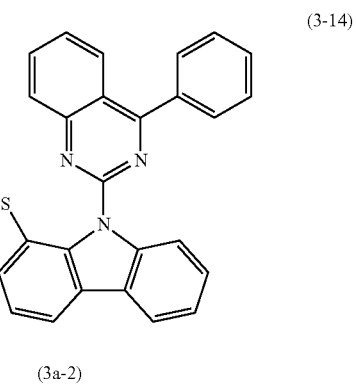

(3-14)

(3a-2)

Example 6

An organic EL device was prepared under the same conditions as in Example 5, except that Compound 1-34 of Synthesis Example 6 was used, instead of Compound 1-5 of Synthesis Example 1, as the material for the second hole transport layer 5b. The resulting organic EL device was measured for the light emission characteristics when a direct current voltage was applied at normal temperature in the atmosphere. The layer configuration is shown in Table 1, and the results of the measurements are shown in Table 2.

Example 7

An organic EL device was prepared under the same conditions as in Example 5, except that the pyrimidine derivative 4-125 was used, instead of the pyrimidine derivative 4-123, as the material for the electron transport layer 7. The resulting organic EL device was measured for the light emission characteristics when a direct current voltage was applied at normal temperature in the atmosphere. The layer configuration is shown in Table 1, and the results of the measurements are shown in Table 2.

Example 8

An organic EL device was prepared under the same conditions as in Example 7, except that Compound 1-34 of Synthesis Example 6 was used, instead of Compound 1-5 of Synthesis Example 1, as the material for the second hole transport layer 5b. The resulting organic EL device was measured for the light emission characteristics when a direct current voltage was applied at normal temperature in the atmosphere. The layer configuration is shown in Table 1, and the results of the measurements are shown in Table 2.

Example 9

An organic EL device was prepared under the same conditions as in Example 1, except that a carbazole derivative 3-16 of the following structural formula was used, instead of Compound 2-4 of Synthesis Example 23, as the material for the luminous layer 6. The resulting organic EL device was measured for the light emission characteristics when a direct current voltage was applied at normal temperature in the atmosphere. The layer configuration is shown in Table 1, and the results of the measurements are shown in Table 2.

(3-16)

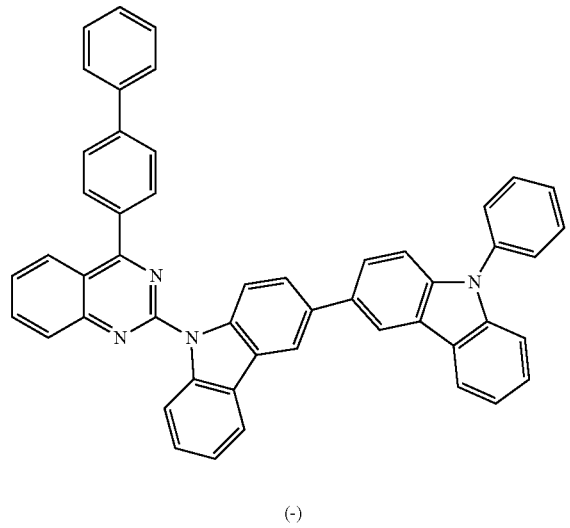

(-)

Example 10

An organic EL device was prepared under the same conditions as in Example 9, except that Compound 1-34 of Synthesis Example 6 was used, instead of Compound 1-5 of Synthesis Example 1, as the material for the second hole transport layer 5b. The resulting organic EL device was measured for the light emission characteristics when a direct current voltage was applied at normal temperature in the atmosphere. The layer configuration is shown in Table 1, and the results of the measurements are shown in Table 2.

Example 11

An organic EL device was prepared under the same conditions as in Example 9, except that the pyrimidine derivative 4-125 was used, instead of the pyrimidine derivative 4-123, as the material for the electron transport layer 7. The resulting organic EL device was measured for the light emission characteristics when a direct current voltage was applied at normal temperature in the atmosphere. The layer configuration is shown in Table 1, and the results of the measurements are shown in Table 2.

Example 12

An organic EL device was prepared under the same conditions as in Example 11, except that Compound 1-34 of Synthesis Example 6 was used, instead of Compound 1-5 of Synthesis Example 1, as the material for the second hole transport layer 5b. The resulting organic EL device was measured for the light emission characteristics when a direct current voltage was applied at normal temperature in the atmosphere. The layer configuration is shown in Table 1, and the results of the measurements are shown in Table 2.

Comparative Example 1

An organic EL device was prepared under the same conditions as in Example 3, except that a triarylamine compound 6'-2 represented by the following structural formula was used, instead of Compound 6-1, as the material for the first hole transport layer 5a, and the triarylamine compound 6'-2 represented by the following structural formula was used, instead of Compound 1-5 of Synthesis Example 1, as the material for the second hole transport layer 5b. In this case, the first hole transport layer 5a and the second hole transport layer 5b functioned as an integrated hole transport layer (film thickness 65 nm). As clear from the structural formula, Compound (6'-2) was a triarylamine compound having two triarylamine structures in the molecule. The resulting organic EL device was measured for the light emission characteristics when a direct current voltage was applied at normal temperature in the atmosphere. The layer configuration is shown in Table 1, and the results of the measurements are shown in Table 2.

(6'-2)

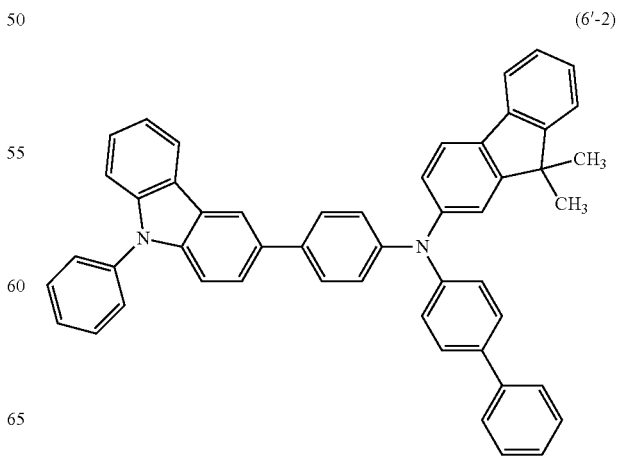

Comparative Example 2

An organic EL device was prepared under the same conditions as in Example 7, except that the triarylamine compound 6'-2 represented by the above structural formula was used, instead of Compound 6-1, as the material for the first hole transport layer 5a, and the triarylamine compound 6'-2 represented by the above structural formula was used, instead of Compound 1-5 of Synthesis Example 1, as the material for the second hole transport layer 5b. In this case, the first hole transport layer 5a and the second hole transport layer 5b functioned as an integrated hole transport layer (film thickness 65 nm). The resulting organic EL device was measured for the light emission characteristics when a direct current voltage was applied at normal temperature in the atmosphere. The layer configuration is shown in Table 1, and the results of the measurements are shown in Table 2.

Comparative Example 3

An organic EL device was prepared under the same conditions as in Example 11, except that the triarylamine compound 6'-2 represented by the above structural formula was used, instead of Compound 6-1, as the material for the first hole transport layer 5a, and the triarylamine compound 6'-2 represented by the above structural formula was used, instead of Compound 1-5 of Synthesis Example 1, as the material for the second hole transport layer 5b. The resulting organic EL device was measured for the light emission characteristics when a direct current voltage was applied at normal temperature in the atmosphere. The layer configuration is shown in Table 1, and the results of the measurements are shown in Table 2.

In Table 2, the device life in each of the organic EL devices of the Examples and the Comparative Examples was measured as the period of time until the emission luminance attenuated to 6790 cd/m$^2$ (corresponding to 97%, with the initial luminance taken as 100%: 97% attenuation) when constant current driving was performed, with the emission luminance at the start of light emission (initial luminance) being set at 7000 cd/m$^2$.

TABLE 1

| | First hole transport layer | Second hole transport layer | Luminous layer | Electron transport layer |
|---|---|---|---|---|
| Ex. 1 | Compound 6-1 | Compound 1-5 | Compound 2-4/ EMD-1 | Compound 4-123/ ETM-1 |
| Ex. 2 | | Compound 1-34 | | |
| Ex. 3 | | Compound 1-5 | | Compound 4-125/ ETM-1 |
| Ex. 4 | | Compound 1-34 | | |
| Ex. 5 | | Compound 1-5 | Compound 3-14/EMD-1 | Compound 4-123/ ETM-1 |
| Ex. 6 | | Compound 1-34 | | |
| Ex. 7 | | Compound 1-5 | | Compound 4-125/ ETM-1 |
| Ex. 8 | | Compound 1-34 | | |
| Ex. 9 | | Compound 1-5 | Compound 3-16/EMD-1 | Compound 4-123/ ETM-1 |
| Ex. 10 | | Compound 1-34 | | |
| Ex. 11 | | Compound 1-5 | | Compound 4-125/ ETM-1 |
| Ex. 12 | | Compound 1-34 | | |
| Comp. Ex. 1 | Compound 6'-2 | Compound 6'-2 | Compound 2-4/ EMD-1 | Compound 4-125/ ETM-1 |
| Comp. Ex. 2 | | | Compound 3-14/EMD-1 | ETM-1 |
| Comp. Ex. 3 | | | Compound 3-16/EMD-1 | |

TABLE 2

| | Voltage (@10 mA/ cm$^2$) [V] | Luminance (@10 mA/ cm$^2$) [cd/m$^2$] | Luminous efficiency (@10 mA/ cm$^2$) [cd/A] | Power efficiency (@10 mA/ cm$^2$) [lm/W] | Device life 97% attenuation (hrs) |
|---|---|---|---|---|---|
| Ex. 1 | 4.26 | 2704 | 27.01 | 19.95 | 277 |
| Ex. 2 | 4.20 | 2660 | 26.56 | 19.85 | 255 |
| Ex. 3 | 4.17 | 2635 | 26.31 | 19.85 | 255 |
| Ex. 4 | 4.09 | 2575 | 25.72 | 19.77 | 320 |
| Ex. 5 | 3.51 | 2574 | 25.78 | 23.17 | 361 |
| Ex. 6 | 3.40 | 2530 | 25.30 | 23.46 | 388 |
| Ex. 7 | 3.39 | 2529 | 25.30 | 23.47 | 298 |
| Ex. 8 | 3.30 | 2513 | 25.13 | 23.99 | 369 |
| Ex. 9 | 3.87 | 2492 | 24.95 | 20.28 | 200 |
| Ex. 10 | 3.80 | 2521 | 25.23 | 20.69 | 241 |
| Ex. 11 | 3.82 | 2514 | 25.15 | 20.68 | 283 |
| Ex. 12 | 3.75 | 2500 | 25.03 | 20.80 | 358 |
| Comp. Ex. 1 | 4.12 | 2230 | 22.33 | 17.04 | 96 |
| Comp. Ex. 2 | 3.42 | 1984 | 19.85 | 18.24 | 79 |
| Comp. Ex. 3 | 3.83 | 2015 | 20.16 | 16.55 | 68 |

Examples 1 to 4 and Comparative Example 1, using the same combination of the materials for the luminous layer, were compared by reference to Tables 1 and 2. The luminous efficiency was 22.33 cd/A in Comparative Example 1, while it was as high as 25.72 to 27.01 cd/A in all of Examples 1 to 4. The power efficiency was 17.04 lm/W in Comparative Example 1, while it was as high as 19.77 to 19.95 lm/W in all of Examples 1 to 4. The device life was 96 hours in Comparative Example 1, but was 255 to 320 hours in Examples 1 to 4, showing much longer life.

Examples 5 to 8 and Comparative Example 2, using the same combination of the materials for the luminous layer, were compared by reference to Tables 1 and 2. The luminous efficiency was 19.85 cd/A in Comparative Example 2, while it was as high as 25.13 to 25.78 cd/A in all of Examples 5 to 8. The power efficiency was 18.24 lm/W in Comparative Example 2, while it was as high as 23.17 to 23.99 lm/W in all of Examples 5 to 8. The device life was 79 hours in Comparative Example 2, but was 298 to 388 hours in Examples 5 to 8, showing much longer life.

Examples 9 to 12 and Comparative Example 3, using the same combination of the materials for the luminous layer, were compared by reference to Tables 1 and 2. The luminous efficiency was 20.16 cd/A in Comparative Example 3, while it was as high as 24.95 to 25.23 cd/A in all of Examples 9 to 12. The power efficiency was 16.55 lm/W in Comparative Example 3, while it was as high as 20.28 to 20.80 lm/W in all of Examples 9 to 12. The device life was 68 hours in Comparative Example 3, but was 200 to 358 hours in Examples 9 to 12, showing much longer life.

With the organic EL device of the present invention, an arylamine compound having a specific structure and a heterocyclic compound having a specific condensed ring structure (and a specific pyrimidine derivative) are combined so as to improve the carrier balance within the organic EL device and to achieve a carrier balance suited to the characteristics of a luminous material. Hence, an organic EL device with a high luminous efficiency and a long life in comparison with conventional organic EL devices can be realized.

INDUSTRIAL APPLICABILITY

The organic EL device of the present invention using the arylamine compound having the specific structure and the heterocyclic compound having the specific condensed ring structure (and the specific pyrimidine derivative) in combination is increased in luminous efficiency, and improved in durability. Hence, the organic EL device of the present invention can be put to uses such as domestic electrical appliances and illumination.

DESCRIPTION OF REFERENCE NUMERALS

1 Glass substrate
2 Transparent anode
3 Hole injection layer
5 Hole transport layer
5a First hole transport layer
5b Second hole transport layer
6 Luminous layer
7 Electron transport layer
8 Electron injection layer
9 Cathode.

The invention claimed is:
1. An organic electroluminescent device having at least an anode, a hole transport layer, a luminous layer, an electron transport layer, and a cathode in this order, wherein
the hole transport layer contains an arylamine compound represented by the following general formula (1), and
the luminous layer contains an indenoindole derivative represented by the following general formula (2) or a carbazole derivative represented by the following general formula (3):

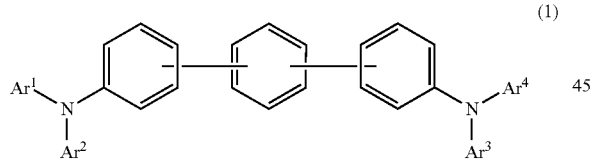

where
$Ar^1$ to $Ar^4$ each represent an aromatic hydrocarbon group, an aromatic heterocyclic group, or a condensed polycyclic aromatic group,

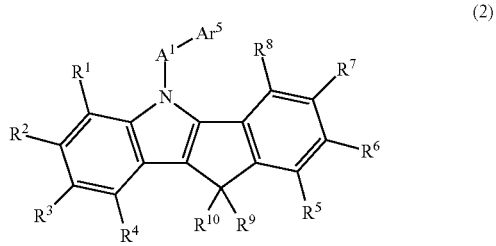

where
$A^1$ represents a divalent group of an aromatic hydrocarbon, a divalent group of an aromatic heterocycle, a divalent group of a condensed polycyclic aromatic ring, or a single bond,
$Ar^5$ represents an aromatic hydrocarbon group, an aromatic heterocyclic group, or a condensed polycyclic aromatic group,
$R^1$ to $R^8$ each represent a hydrogen atom; a deuterium atom; a fluorine atom; a chlorine atom; a cyano group; a nitro group; an alkyl group having 1 to 6 carbon atoms; a cycloalkyl group having 5 to 10 carbon atoms; an alkenyl group having 2 to 6 carbon atoms; an alkyloxy group having 1 to 6 carbon atoms; a cycloalkyloxy group having 5 to 10 carbon atoms; an aromatic hydrocarbon group; an aromatic heterocyclic group; a condensed polycyclic aromatic group; an aryloxyl group; or a di-substituted amino group having an aromatic hydrocarbon group, an aromatic heterocyclic group, or a condensed polycyclic aromatic group as a substituent,
$R^1$ to $R^4$ may be bonded to each other via a single bond, a substituted or unsubstituted methylene group, an oxygen atom, or a sulfur atom to form a ring,
$R^5$ to $R^8$ may be bonded to each other via a single bond, a substituted or unsubstituted methylene group, an oxygen atom, or a sulfur atom to form a ring,
part of $R^1$ to $R^4$ may be detached, and remaining group of $R^1$ to $R^4$ may be bonded to a vacancy, which has been produced by detachment, via a substituted or unsubstituted methylene group, an oxygen atom, a sulfur atom, or a monoarylamino group to form a ring,
part of $R^5$ to $R^8$ may be detached, and remaining group of $R^5$ to $R^8$ may be bonded to a vacancy, which has been produced by detachment, via a substituted or unsubstituted methylene group, an oxygen atom, a sulfur atom, or a monoarylamino group to form a ring, and
$R^9$ and $R^{10}$ each represent an alkyl group having 1 to 6 carbon atoms, an aromatic hydrocarbon group, an aromatic heterocyclic group, or a condensed polycyclic aromatic group, and $R^9$ and $R^{10}$ may be bonded to each other via a single bond, a substituted or unsubstituted methylene group, an oxygen atom, or a sulfur atom to form a ring,

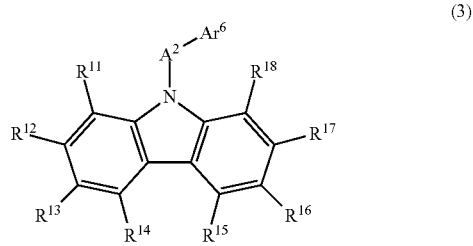

where
$A^2$ represents a divalent group of an aromatic hydrocarbon, a divalent group of an aromatic heterocycle, a divalent group of a condensed polycyclic aromatic ring, or a single bond,
$Ar^6$ represents an aromatic hydrocarbon group, an aromatic heterocyclic group, or a condensed polycyclic aromatic group,
$R^{11}$ to $R^{18}$ each represent a hydrogen atom; a deuterium atom; a fluorine atom; a chlorine atom; a cyano group;

a nitro group; an alkyl group having 1 to 6 carbon atoms; a cycloalkyl group having 5 to 10 carbon atoms; an alkenyl group having 2 to 6 carbon atoms; an alkyloxy group having 1 to 6 carbon atoms; a cycloalkyloxy group having 5 to 10 carbon atoms; an aromatic hydrocarbon group; an aromatic heterocyclic group; a condensed polycyclic aromatic group; an aryloxyl group; or a di-substituted amino group having an aromatic hydrocarbon group, an aromatic heterocyclic group, or a condensed polycyclic aromatic group as a substituent, $R^{11}$ to $R^{14}$ may be bonded to each other via a single bond, a substituted or unsubstituted methylene group, an oxygen atom, or a sulfur atom to form a ring, $R^{15}$ to $R^{18}$ may be bonded to each other via a single bond, a substituted or unsubstituted methylene group, an oxygen atom, or a sulfur atom to form a ring, part of $R^{11}$ to $R^{14}$ may be detached, and remaining group of $R^{11}$ to $R^{14}$ may be bonded to a vacancy, which has been produced by detachment, via a substituted or unsubstituted methylene group, an oxygen atom, a sulfur atom, or a monoarylamino group to form a ring, and part of $R^{15}$ to $R^{18}$ may be detached, and remaining group of $R^{15}$ to $R^{18}$ may be bonded to a vacancy, which has been produced by detachment, via a substituted or unsubstituted methylene group, an oxygen atom, a sulfur atom, or a monoarylamino group to form a ring.

2. The organic electroluminescent device according to claim 1, wherein
the electron transport layer contains a pyrimidine derivative represented by the following general formula (4):

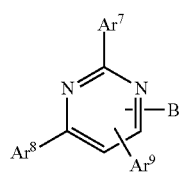

(4)

where
$Ar^7$ represents an aromatic hydrocarbon group, an aromatic heterocyclic group, or a condensed polycyclic aromatic group,
$Ar^8$ and $Ar^9$ each represent a hydrogen atom, an aromatic hydrocarbon group, an aromatic heterocyclic group, or a condensed polycyclic aromatic group, and $Ar^8$ and $Ar^9$ are each not a hydrogen atom simultaneously, and
B represents a monovalent group represented by the following structural formula (5):

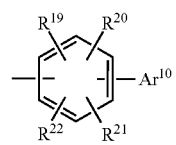

(5)

where
$Ar^{10}$ represents an aromatic heterocyclic group,
$R^{19}$ to $R^{22}$ each represent a hydrogen atom, a deuterium atom, a fluorine atom, a chlorine atom, a cyano group, a trifluoromethyl group, an alkyl group having 1 to 6 carbon atoms, an aromatic hydrocarbon group, an aromatic heterocyclic group, or a condensed polycyclic aromatic group, and $R^{19}$ to $R^{22}$ and $Ar^{10}$ may be bonded to each other via a single bond, a substituted or unsubstituted methylene group, an oxygen atom, or a sulfur atom to form a ring.

3. The organic electroluminescent device according to claim 2, wherein
the pyrimidine derivative is represented by the following general formula (4a):

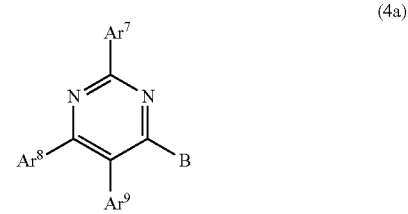

(4a)

where
$Ar^7$ to $Ar^9$ and B are as defined in the general formula (4).

4. The organic electroluminescent device according to claim 2, wherein
the pyrimidine derivative is represented by the following general formula (4b):

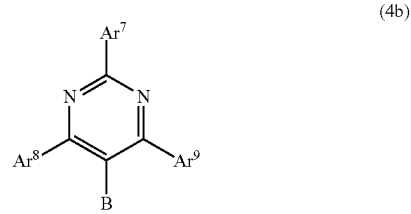

(4b)

where
$Ar^7$ to $Ar^9$ and B are as defined in the general formula (4).

5. The organic electroluminescent device according to claim 2, wherein
in the general formula (4), B is a monovalent group represented by the following structural formula (5a):

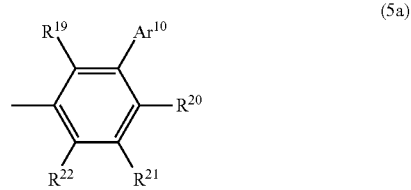

(5a)

where
$Ar^{10}$ and $R^{19}$ to $R^{22}$ are as defined in the structural formula (5).

6. The organic electroluminescent device according to claim 1, wherein
the hole transport layer has a two-layer structure composed of a first hole transport layer and a second hole transport layer, and the second hole transport layer is located on a side of the luminous layer and contains the arylamine compound represented by the general formula (1).

7. The organic electroluminescent device according to claim 1, wherein
the luminous layer contains a red luminous material.

8. The organic electroluminescent device according to claim 1, wherein
the luminous layer contains a phosphorescent luminous material.

9. The organic electroluminescent device according to claim 8, wherein
the phosphorescent luminous material is a metal complex containing iridium or platinum.

* * * * *